(12) United States Patent
Simon et al.

(10) Patent No.: US 12,329,964 B2
(45) Date of Patent: *Jun. 17, 2025

(54) TREATMENT PARADIGMS FOR NERVE STIMULATION

(71) Applicant: ElectroCore, Inc., Rockaway, NJ (US)

(72) Inventors: Bruce J. Simon, Santa Fe, NM (US); Joseph P. Errico, Palm Beach Gardens, FL (US)

(73) Assignee: ElectroCore, Inc., Rockaway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/228,918

(22) Filed: Aug. 1, 2023

(65) Prior Publication Data

US 2023/0381499 A1 Nov. 30, 2023

Related U.S. Application Data

(63) Continuation of application No. 17/843,736, filed on Jun. 17, 2022, now Pat. No. 11,779,756, which is a
(Continued)

(51) Int. Cl.
*A61N 1/36* (2006.01)
*A61N 1/00* (2006.01)
(Continued)

(52) U.S. Cl.
CPC .............. *A61N 1/0551* (2013.01); *A61N 1/00* (2013.01); *A61N 1/0456* (2013.01);
(Continued)

(58) Field of Classification Search
CPC ..... A61N 1/00; A61N 1/0456; A61N 1/36014
See application file for complete search history.

(56) References Cited

U.S. PATENT DOCUMENTS

| 3,590,810 A | 7/1971 | Kopecky |
| 4,196,737 A | 4/1980 | Bevilacqua |

(Continued)

FOREIGN PATENT DOCUMENTS

| EP | 1967226 | 9/2008 |
| EP | 2777764 | 8/2015 |

(Continued)

OTHER PUBLICATIONS

Greicius et al., Functional connectivity in the resting brain: A network analysis of the default mode hypothesis, PNAS, Jan. 2003, vol. 100, No. 1, pp. 253-258.
(Continued)

*Primary Examiner* — Catherine M Voorhees
(74) *Attorney, Agent, or Firm* — Farber LLC

(57) ABSTRACT

Methods are disclosed for electrical stimulation of nerves to treat one or more symptoms in a user. The methods comprise transcutaneously transmitting electrical impulses to the nerve according to a treatment paradigm. The treatment paradigm may include generating and transmitting the electrical impulse as a single dose from about 30 seconds to about 5 minutes. The treatment paradigm may comprise a treatment session of 2 to 4 times within an hour time period and/or as a single dose from 2 to 5 times during a day.

11 Claims, 13 Drawing Sheets

Related U.S. Application Data continuation of application No. 17/402,690, filed on Aug. 16, 2021, now Pat. No. 11,389,646, which is a continuation of application No. 16/542,818, filed on Aug. 16, 2019, now Pat. No. 11,191,953, which is a continuation of application No. 13/952,916, filed on Jul. 29, 2013, now Pat. No. 10,441,780, which is a continuation-in-part of application No. 13/603,781, filed on Sep. 5, 2012, now Pat. No. 8,983,628, which is a continuation-in-part of application No. 13/222,087, filed on Aug. 31, 2011, now Pat. No. 9,174,066, said application No. 13/183,765 is a continuation-in-part of application No. 13/183,721, filed on Jul. 15, 2011, now Pat. No. 8,676,324, said application No. 13/222,087 is a continuation-in-part of application No. 13/183,765, filed on Jul. 15, 2011, now Pat. No. 8,874,227, said application No. 13/952,916 is a continuation-in-part of application No. 13/109,250, filed on May 17, 2011, now Pat. No. 8,676,330, and a continuation-in-part of application No. 13/075,746, filed on Mar. 30, 2011, now Pat. No. 8,874,205, and a continuation-in-part of application No. 13/005,005, filed on Jan. 12, 2011, now Pat. No. 8,868,177, which is a continuation-in-part of application No. 12/964,050, filed on Dec. 9, 2010, now abandoned, said application No. 13/952,916 is a continuation-in-part of application No. 12/859,568, filed on Aug. 19, 2010, now Pat. No. 9,037,247.

(60) Provisional application No. 61/488,208, filed on May 20, 2011, provisional application No. 61/487,439, filed on May 18, 2011, provisional application No. 61/471,405, filed on Apr. 4, 2011, provisional application No. 61/451,259, filed on Mar. 10, 2011, provisional application No. 61/415,469, filed on Nov. 19, 2010.

(51) Int. Cl.
*A61N 1/04* (2006.01)
*A61N 1/05* (2006.01)
*A61N 2/00* (2006.01)
*A61B 5/00* (2006.01)
*A61B 5/369* (2021.01)
*A61N 2/02* (2006.01)

(52) U.S. Cl.
CPC ..... *A61N 1/36014* (2013.01); *A61N 1/36021* (2013.01); *A61N 1/36025* (2013.01); *A61N 2/006* (2013.01); *A61B 5/369* (2021.01); *A61B 5/4836* (2013.01); *A61N 1/0408* (2013.01); *A61N 1/36053* (2013.01); *A61N 2/008* (2013.01); *A61N 2/02* (2013.01)

(56) References Cited

U.S. PATENT DOCUMENTS

| | | | |
|---|---|---|---|
| 4,989,605 A | 2/1991 | Rossen | |
| 5,109,847 A | 5/1992 | Liss et al. | |
| 5,458,141 A | 10/1995 | Neil | |
| 5,487,759 A | 1/1996 | Bastyr et al. | |
| 5,782,874 A | 7/1998 | Loos | |
| 5,899,922 A | 5/1999 | Loos | |
| 5,983,131 A | 11/1999 | Weaver et al. | |
| 6,104,956 A | 8/2000 | Naritoku et al. | |
| 6,341,236 B1 | 1/2002 | Osorio et al. | |
| 6,366,814 B1 | 4/2002 | Boveja et al. | |
| 6,463,327 B1 | 10/2002 | Lurie et al. | |
| 6,587,719 B1 | 7/2003 | Barrett et al. | |
| 6,610,713 B2 | 8/2003 | Tracey | |
| 6,631,297 B1 | 10/2003 | Mo | |
| 7,254,444 B2 | 8/2007 | Moore | |
| 7,734,340 B2 | 6/2010 | De Ridder | |
| 7,797,041 B2 | 9/2010 | Libbus et al. | |
| 8,849,407 B1* | 9/2014 | Danilov | A61N 1/0548 607/45 |
| 8,965,535 B2* | 2/2015 | Dunlay | A61N 1/3601 607/149 |
| 10,441,780 B2* | 10/2019 | Simon | A61N 2/006 |
| 11,389,646 B2* | 7/2022 | Simon | A61N 2/006 |
| 11,779,756 B2* | 10/2023 | Simon | A61N 2/006 607/42 |
| 2002/0099417 A1 | 7/2002 | Naritoku et al. | |
| 2002/0183237 A1 | 12/2002 | Puskas | |
| 2002/0183804 A1 | 12/2002 | Malaney et al. | |
| 2003/0212311 A1 | 11/2003 | Nova et al. | |
| 2004/0073271 A1 | 4/2004 | Harry et al. | |
| 2004/0243182 A1 | 12/2004 | Cohen et al. | |
| 2004/0249416 A1 | 12/2004 | Yun et al. | |
| 2005/0021092 A1 | 1/2005 | Yun et al. | |
| 2005/0065574 A1 | 3/2005 | Rezai | |
| 2005/0113630 A1 | 5/2005 | Fox et al. | |
| 2005/0137644 A1 | 6/2005 | Boveja et al. | |
| 2005/0165458 A1 | 7/2005 | Boveja | |
| 2005/0187590 A1 | 8/2005 | Boveja et al. | |
| 2005/0216062 A1 | 9/2005 | Herbst | |
| 2005/0267544 A1 | 12/2005 | Lee et al. | |
| 2005/0278001 A1 | 12/2005 | Qin et al. | |
| 2006/0015153 A1 | 1/2006 | Gliner et al. | |
| 2006/0074284 A1 | 4/2006 | Juola et al. | |
| 2006/0074450 A1 | 4/2006 | Boveja et al. | |
| 2006/0100668 A1 | 5/2006 | Ben-David et al. | |
| 2006/0100671 A1 | 5/2006 | Ridder | |
| 2006/0173510 A1* | 8/2006 | Besio | A61B 5/375 607/45 |
| 2006/0178703 A1 | 8/2006 | Huston et al. | |
| 2007/0027496 A1 | 2/2007 | Parnis et al. | |
| 2007/0038264 A1 | 2/2007 | Jaax et al. | |
| 2007/0106337 A1 | 5/2007 | Errico et al. | |
| 2007/0123952 A1* | 5/2007 | Strother | A61N 1/36021 607/48 |
| 2007/0142886 A1 | 6/2007 | Fischell et al. | |
| 2007/0150006 A1 | 6/2007 | Libbus et al. | |
| 2007/0156182 A1 | 7/2007 | Castel et al. | |
| 2007/0250145 A1 | 10/2007 | Kraus et al. | |
| 2007/0276449 A1 | 11/2007 | Gunter et al. | |
| 2008/0021512 A1 | 1/2008 | Knudson et al. | |
| 2008/0027513 A1 | 1/2008 | Carbunaru | |
| 2008/0045776 A1 | 2/2008 | Fischell et al. | |
| 2008/0077192 A1 | 3/2008 | Harry et al. | |
| 2008/0114199 A1 | 5/2008 | Riehl et al. | |
| 2008/0132964 A1 | 6/2008 | Cohen et al. | |
| 2008/0177190 A1 | 7/2008 | Libbus et al. | |
| 2008/0208266 A1 | 8/2008 | Lesser et al. | |
| 2008/0306325 A1 | 12/2008 | Burnett et al. | |
| 2009/0036945 A1 | 2/2009 | Chancellor | |
| 2009/0099622 A1 | 4/2009 | Fowler | |
| 2009/0112283 A1 | 4/2009 | Kriksunov et al. | |
| 2009/0132018 A1 | 5/2009 | DiUbaldi et al. | |
| 2009/0157149 A1 | 6/2009 | Wahlgren et al. | |
| 2009/0182393 A1 | 7/2009 | Bachinski | |
| 2009/0234417 A1 | 9/2009 | Pastena et al. | |
| 2009/0234419 A1 | 9/2009 | Maschino et al. | |
| 2009/0240297 A1 | 9/2009 | Shavit et al. | |
| 2009/0287035 A1 | 11/2009 | Dietrich et al. | |
| 2010/0030299 A1 | 2/2010 | Covalin | |
| 2010/0057154 A1* | 3/2010 | Dietrich | A61N 1/36017 607/45 |
| 2010/0152794 A1 | 6/2010 | Radivojevic et al. | |
| 2010/0152811 A1 | 6/2010 | Flaherty | |
| 2010/0286553 A1 | 11/2010 | Feler et al. | |
| 2011/0046432 A1 | 2/2011 | Simon et al. | |
| 2011/0152967 A1 | 6/2011 | Simon et al. | |
| 2011/0213295 A1 | 9/2011 | Henley et al. | |
| 2011/0224749 A1 | 9/2011 | Ben-David et al. | |
| 2011/0230701 A1* | 9/2011 | Simon | A61N 1/0456 607/46 |

(56) References Cited

U.S. PATENT DOCUMENTS

| | | | |
|---|---|---|---|
| 2012/0029591 A1* | 2/2012 | Simon | A61N 1/40 |
| | | | 607/42 |
| 2012/0029601 A1 | 2/2012 | Simon et al. | |
| 2012/0283697 A1 | 11/2012 | Kim et al. | |
| 2012/0303080 A1 | 11/2012 | Ben-David et al. | |
| 2013/0006322 A1 | 1/2013 | Tai | |
| 2013/0060304 A1 | 3/2013 | LaTendresse et al. | |
| 2013/0245486 A1 | 9/2013 | Simon et al. | |
| 2014/0005743 A1 | 1/2014 | Giuffrida et al. | |
| 2014/0172041 A1 | 6/2014 | Draghici | |
| 2014/0222102 A1 | 8/2014 | Lemus | |
| 2014/0236040 A1 | 8/2014 | Moon | |
| 2014/0031895 A1 | 10/2014 | Rahimi | |
| 2015/0165226 A1 | 6/2015 | Simon et al. | |
| 2015/0190637 A1 | 7/2015 | Simon et al. | |

FOREIGN PATENT DOCUMENTS

| | | |
|---|---|---|
| JP | 2006-515192 | 11/2006 |
| JP | 2009-125263 | 6/2009 |
| JP | 2012-52385 | 9/2013 |
| JP | 2014-510586 | 5/2014 |
| KR | 101242190 | 3/2013 |
| WO | WO1993/01862 | 2/1993 |
| WO | WO2005/007120 | 1/2005 |
| WO | WO2007/092062 | 8/2007 |
| WO | WO2007/149811 | 12/2007 |
| WO | WO2008/042902 | 4/2008 |
| WO | WO2007/058780 | 5/2008 |
| WO | WO2009/021080 | 2/2009 |
| WO | WO2009/064641 | 5/2009 |
| WO | WO2009/135693 | 11/2009 |
| WO | WO2012/121750 | 9/2012 |
| WO | WO 2012/174330 | 12/2012 |
| WO | WO2013/066135 | 5/2013 |

OTHER PUBLICATIONS

Heneka et al., Locus ceruleus controls Alzheimer's disease pathology by modulating microglial functions through norepinephrine, PNAS, Mar. 2010, vol. 107, No. 13, pp. 6058-6063.
Lee et al., Clustering of Resting State Networks, PLoS One, Jul. 2012, vol. 7, Issue 7, pp. 1-12.
Miyoshi, K. and Morimura, Y. "Clinical Manifestations of Neuropsychiatric Disorders," 2010, Neuropsychiatric Disorders, Springer, XIV, pp. 1-15.
International Search Report and Written Opinion dated Aug. 25, 2015 in related Application No. PCT/US15/31847 filed May 20, 2015 (10 pages).
International Search Report and Written Opinion dated May 8, 2007 in related PCT Application No. PCT/US2006/042823 filed Nov. 2, 2006 (5 pages).
International Search Report and Written Opinion dated Sep. 17, 2007 in related PCT Application No. PCT/US2006/042828 filed Nov. 2, 2006 (5 pages).
International Search Report and Written Opinion dated Mar. 26, 2008 in related PCT Application No. PCT/US2006/042752 filed Nov. 1, 2006 (7 pages).
International Search Report and Written Opinion dated Dec. 22, 2011 in related PCT Application No. PCT/US2011/049844 filed Aug. 31, 2011 (9 pages).
International Search Report and Written Opinion dated Apr. 30, 2013 in related PCT Application No. PCT/US2013/023014 filed Jan. 24, 2013 (7 pages).
International Search Report and Written Opinion dated Dec. 11, 2013 in related PCT Application No. PCT/US2013/058079 filed Sep. 4, 2013 (8 pages).
International Search Report and Written Opinion dated Jan. 29, 2014 in related PCT Application No. PCT/US2013/068804 filed Nov. 6, 2013 (10 pages).
Europe Office Action dated Apr. 24, 2018 in related Application No. 15796247.3 filed May 20, 2015 (6 pages).
Europe Office Action dated Jul. 26, 2018 in related Application No. 11818591.7 filed Aug. 12, 2011 (8 pages).

* cited by examiner

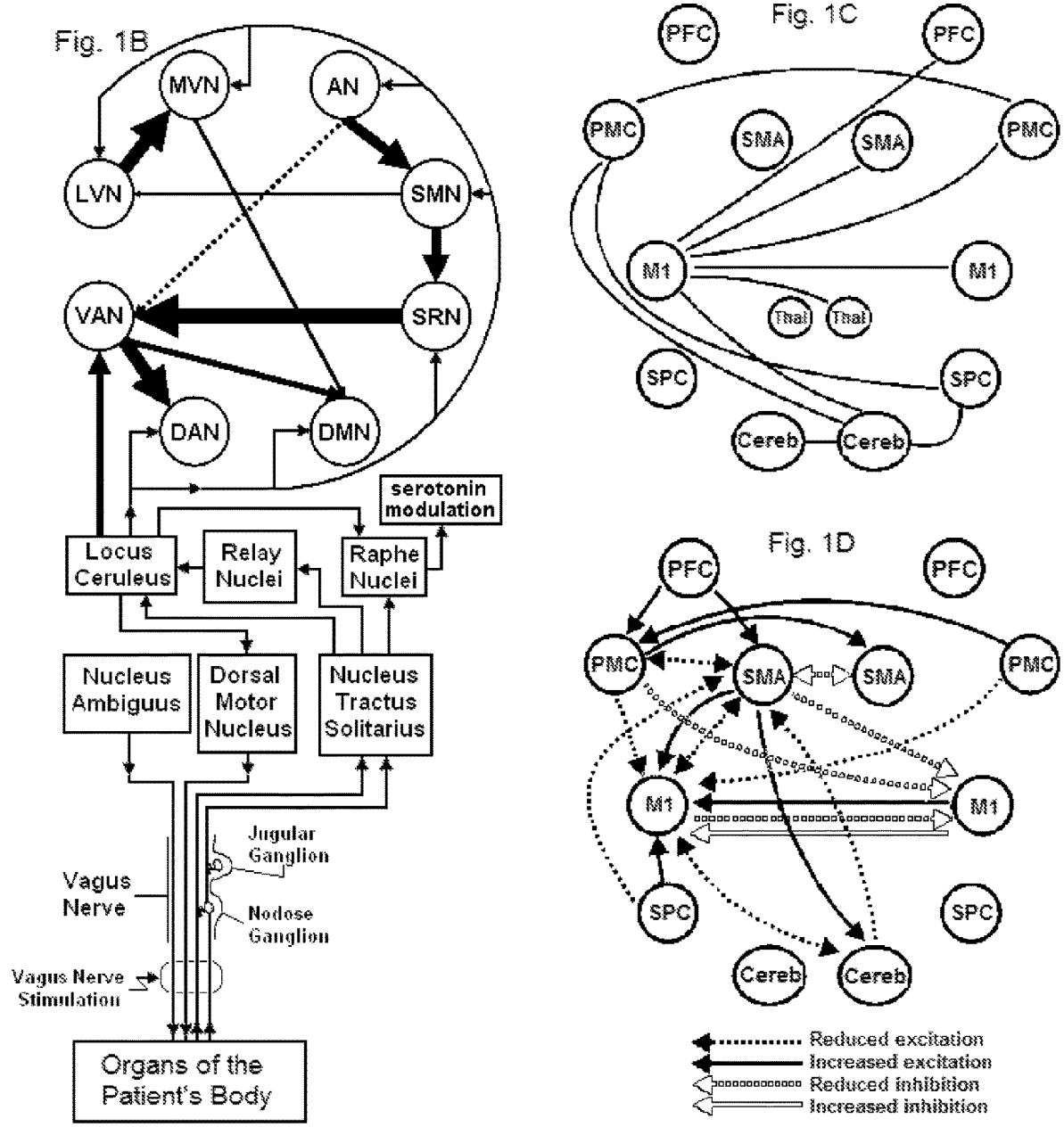

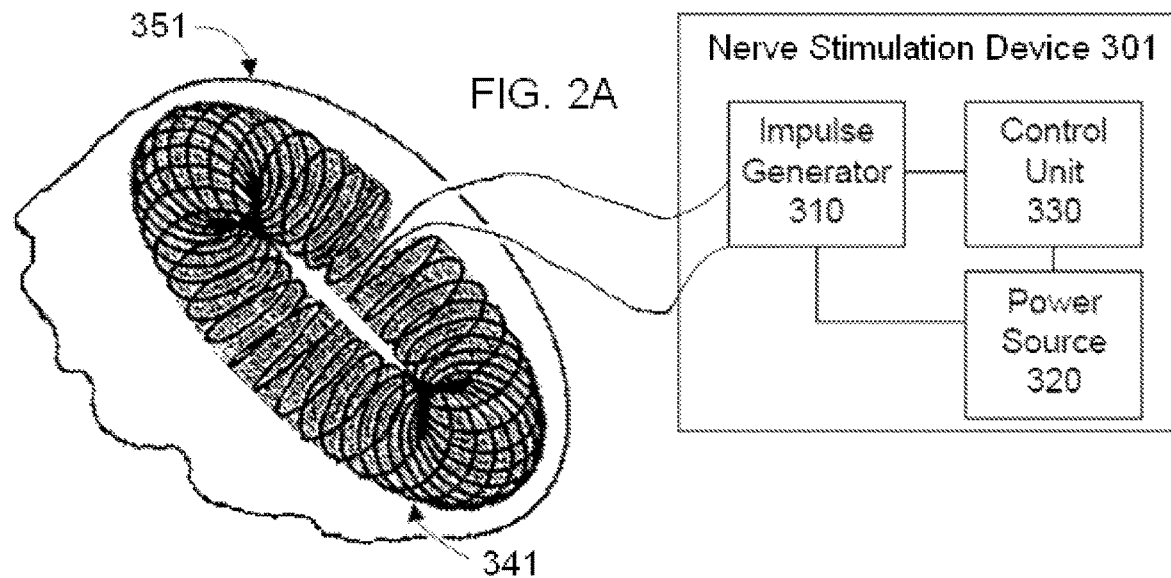
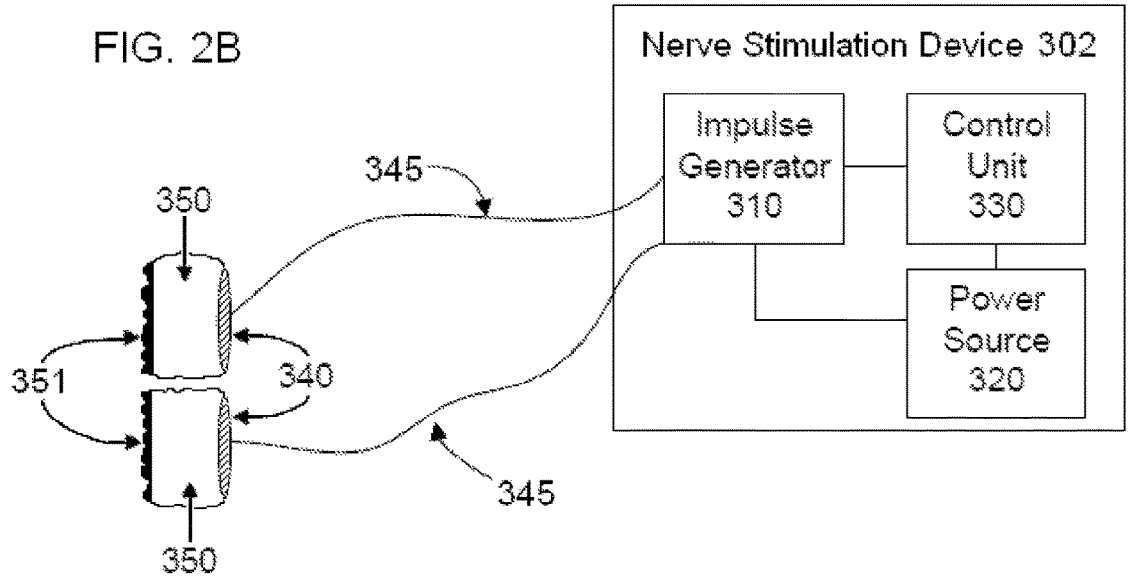

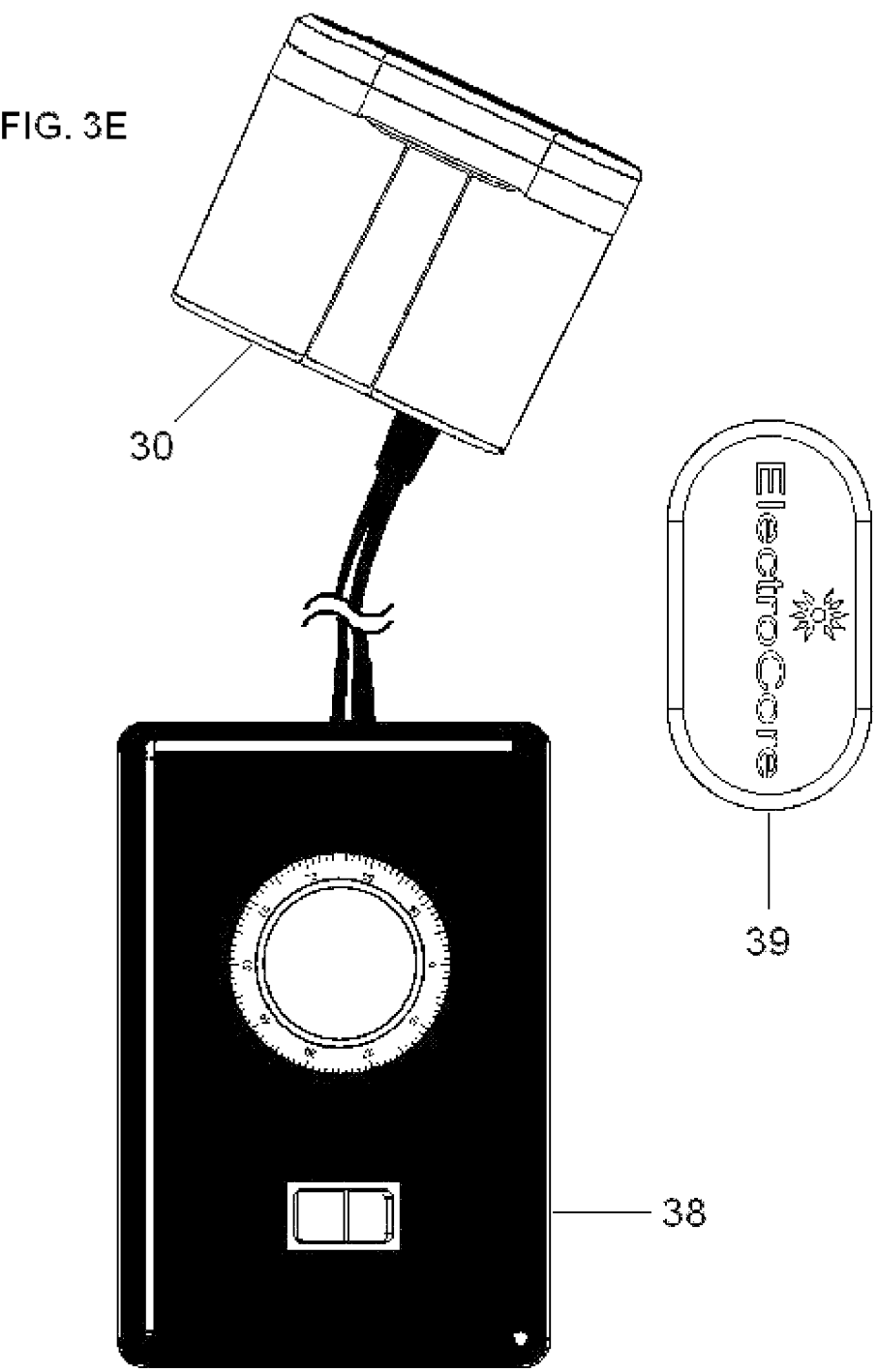

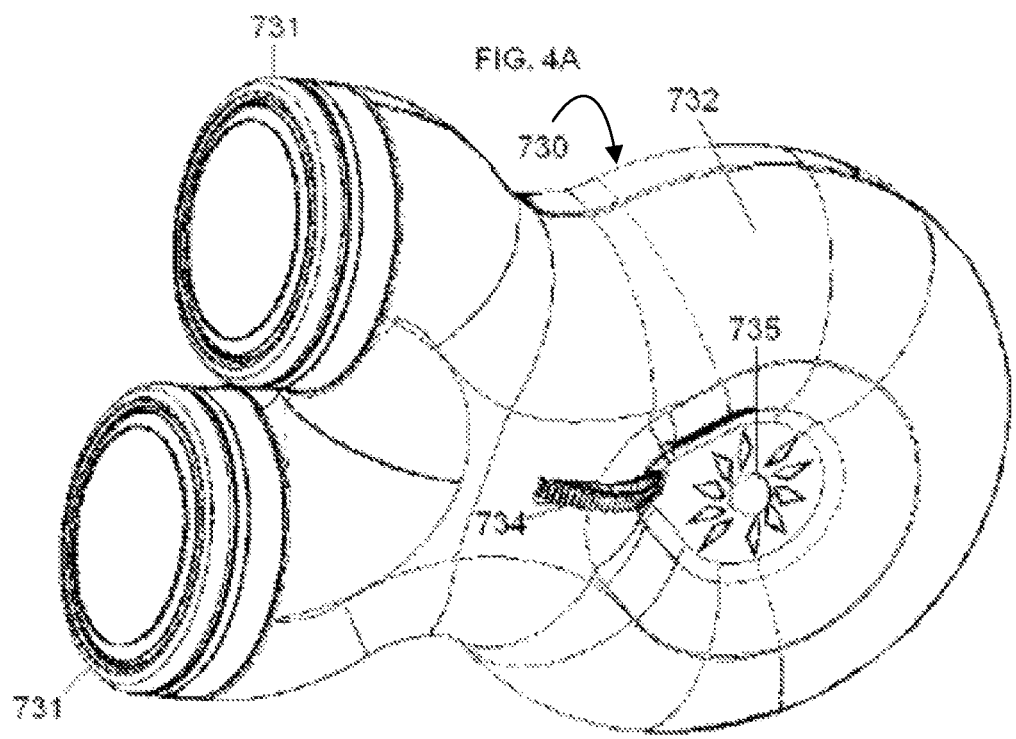
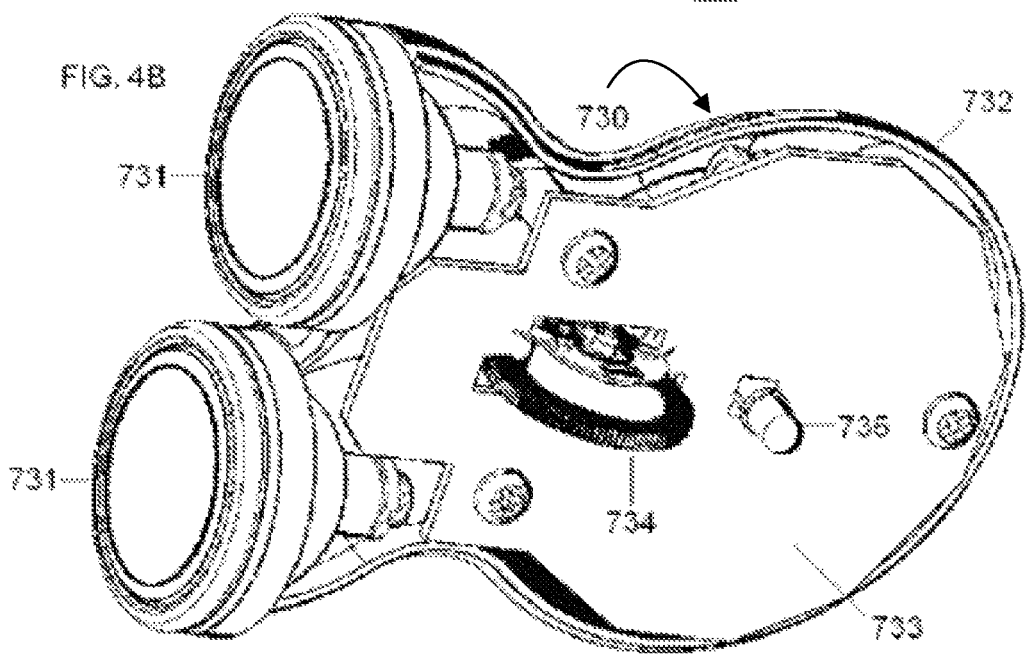

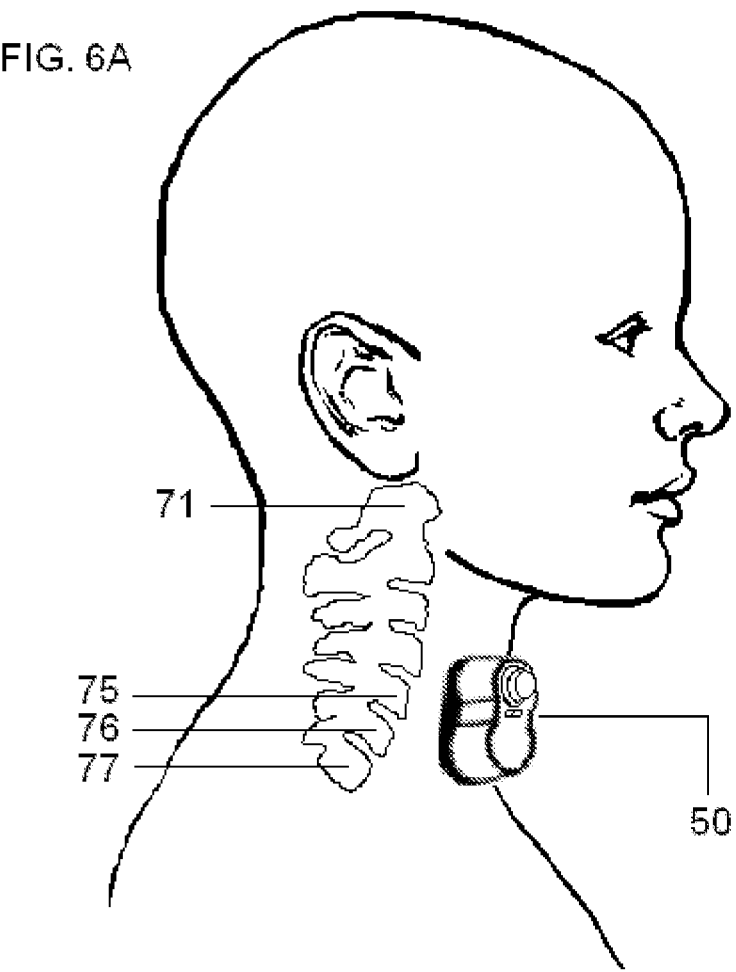

TREATMENT PARADIGMS FOR NERVE STIMULATION

CROSS REFERENCE TO RELATED APPLICATIONS

This application is a Continuation of U.S. Pat. No. 17,843,736, filed Jun. 17, 2022, which is a Continuation of U.S. Pat. No. 17,402,690, filed Aug. 16, 2021 (now U.S. Pat. No. 11,389,6460), which is a Continuation of U.S. patent application Ser. No. 16/542,818, filed Aug. 16, 2019 (now U.S. Pat. No. 11,191,953), which is a Continuation of U.S. patent application Ser. No. 13/952,916 filed Jul. 29, 2013 (now U.S. Pat. No. 10,441,780), which is a Continuation in Part of U.S. patent application Ser. No. 13/603,781 filed Sep. 5, 2012 (now U.S. Pat. No. 8,983,628); which is a Continuation in Part of U.S. patent application Ser. No. 13/222,087 filed Aug. 31, 2011 (now U.S. Pat. No. 9,174,066); which is a Continuation in Part of U.S. patent application Ser. No. 13/183,765 filed Jul. 15, 2011 (now U.S. Pat. No. 8,874,227); which is a Continuation in Part of U.S. patent application Ser. No. 13/183,721 filed Jul. 15, 2011 (now U.S. Pat. No. 8,676,324); which claims the benefit of priority to U.S. Provisional Application No. 61/488,208 filed May 20, 2011 and U.S. Provisional Application No. 61/487,439 filed May 18, 2011. This application also is a Continuation in Part of U.S. patent application Ser. No. 13/109,250 filed May 17, 2011 (now U.S. Pat. No. 8,676,330); which claims the benefit of priority to U.S. Provisional Application No. 61/471,405 filed Apr. 4, 2011. This application is also a Continuation in Part of U.S. patent application Ser. No. 13/024,727, filed Feb. 10, 2011 (now U.S. Pat. No. 9,089,719). This application also is a Continuation in Part of U.S. patent application Ser. No. 13/075,746 filed Mar. 30, 2011 (now U.S. Pat. No. 8,874,205); which claims the benefit of priority to U.S. Provisional Application No. 61/451,259 filed Mar. 10, 2011. This application also is a Continuation in Part of U.S. patent application Ser. No. 13/005,005 filed Jan. 12, 2011; which is a Continuation in Part of U.S. patent application Ser. No. 12/964,050 filed Dec. 9, 2010; which claims the benefit of priority to U.S. Provisional Application No. 61/415,469 filed Nov. 19, 2010. The complete disclosure of all of these patents and applications are incorporated herein by reference in their entirety for all purposes.

BACKGROUND

The field of the present description relates to the delivery of energy impulses (and/or fields) to bodily tissues for therapeutic purposes. The description relates more specifically to devices and methods for treating conditions associated with stroke and/or transient ischemic attacks. The energy impulses (and/or fields) that are used to treat those conditions comprise electrical and/or electromagnetic energy, delivered non-invasively to the patient The use of electrical stimulation for treatment of medical conditions is well known. For example, electrical stimulation of the brain with implanted electrodes (deep brain stimulation) has been approved for use in the treatment of various conditions, including pain and movement disorders such as essential tremor and Parkinson's disease [Joel S. PERLMUTTER and Jonathan W. Mink. Deep brain stimulation. Annu. Rev. Neurosci 29 (2006):229-257].

Another application of electrical stimulation of nerves is the treatment of radiating pain in the lower extremities by stimulating the sacral nerve roots at the bottom of the spinal cord [Paul F. WHITE, Shitong Li and Jen W. Chiu. Electroanalgesia: Its Role in Acute and Chronic Pain Management. Anesth Analg 92(2001):505-513; patent U.S. Pat. No. 6,871,099, entitled Fully implantable microstimulator for spinal cord stimulation as a therapy for chronic pain, to WHITEHURST, et al].

Many other forms of nerve stimulation exist [HATZIS A, Stranjalis G, Megapanos C, Sdrolias P G, Panourias I G, Sakas D E. The current range of neuromodulatory devices and related technologies. Acta Neurochir Suppl 97(Pt 1,2007):21-29]. The type of electrical stimulation that is most relevant to the present description is vagus nerve stimulation (VNS, also known as vagal nerve stimulation). It was developed initially for the treatment of partial onset epilepsy and was subsequently developed for the treatment of depression and other disorders. The left vagus nerve is ordinarily stimulated at a location within the neck by first implanting an electrode about the vagus nerve during open neck surgery and by then connecting the electrode to an electrical stimulator circuit (a pulse generator). The pulse generator is ordinarily implanted subcutaneously within a pocket that is created at some distance from the electrode, which is usually in the left infraclavicular region of the chest. A lead is then tunneled subcutaneously to connect the electrode assembly and pulse generator. The patient's stimulation protocol is then programmed using a device (a programmer) that communicates with the pulse generator, with the objective of selecting electrical stimulation parameters that best treat the patient's condition (pulse frequency, stimulation amplitude, pulse width, etc.) [U.S. Pat. No. 4,702,254 entitled Neurocybernetic prosthesis, to ZABARA; U.S. Pat. No. 6,341,236 entitled Vagal nerve stimulation techniques for treatment of epileptic seizures, to OSORIO et al; U.S. Pat. No. 5,299,569 entitled Treatment of neuropsychiatric disorders by nerve stimulation, to WERNICKE et al; G. C. ALBERT, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009):1042-1060; GROVES D A, Brown V J. Vagal nerve stimulation: a review of its applications and potential mechanisms that mediate its clinical effects. Neurosci Biobehav Rev 29(2005):493-500; Reese TERRY, Jr. Vagus nerve stimulation: a proven therapy for treatment of epilepsy strives to improve efficacy and expand applications. Conf Proc IEEE Eng Med Biol Soc. 2009; 2009:4631-4634; Timothy B. MAPSTONE. Vagus nerve stimulation: current concepts. Neurosurg Focus 25 (3,2008):E9, pp. 1-4; ANDREWS, R. J. Neuromodulation. I. Techniques-deep brain stimulation, vagus nerve stimulation, and transcranial magnetic stimulation. Ann. N. Y. Acad. Sci. 993(2003):1-13; LABINER, D. M., Ahern, G. L. Vagus nerve stimulation therapy in depression and epilepsy: therapeutic parameter settings. Acta. Neurol. Scand. 115(2007): 23-33; AMAR, A. P., Levy, M. L., Liu, C. Y., Apuzzo, M. L. J. Vagus nerve stimulation. Proceedings of the IEEE 96(7, 2008):1142-1151; CLANCY JA, Deuchars S A, Deuchars J. The wonders of the Wanderer. Exp Physiol 98(1,2013):38-45].

Prior art vagal nerve stimulators typically have treatment paradigms that require continuous stimulation of the vagus nerve. The term "continuous stimulate" as defined herein means stimulation that either literally remains ON for 24 hours/day and seven days/week or follows a certain ON/Off pattern continuously for 24 hours/day and seven days/week. For example, existing implantable vagal nerve stimulators "continuously stimulate" the vagus nerve with a typical pattern of 30 seconds ON/5 minutes OFF (or the like) for 24 hours/day and seven days/week. Unfortunately, this not only involves a continuous drain on the power supply of the vagal nerve stimulator, but it makes it very difficult, if not impossible, to provide treatment with a vagal nerve stimulator that is not implanted on the nerve.

SUMMARY

The present description provides systems, apparatus and methods for selectively applying electrical energy to body tissue, particularly to a vagus nerve at a location in a patient's neck. Methods are provided to apply an electrical impulse to modulate, stimulate, inhibit or block electrical signals in nerves within or around the carotid sheath, to prevent or treat a condition or symptom of a patient. The electrical signal may be adapted to reduce, stimulate, inhibit or block electrical signals in a vagus nerve to treat many conditions, such as bronchoconstriction associated with asthma, COPD or the like, hypotension associated with sepsis or anaphylaxis, allergic rhinitis, chronic sinusitis, stroke, hypertension, diabetes, hypovolemic shock, sepsis, epilepsy, depression, obesity, anxiety disorders, migraine, cluster headache, tension headache, post-concussion headache, post-traumatic stress disorder, GI disorders, autism, stroke, modulation of liver function to alter cholesterol production, neurodegenerative disorders, such Alzheimer's disease and the like, and any other ailment affected by vagus nerve transmissions.

Methods are also disclosed for using the induced euphoria in individuals needing relief from mental and physical stress, depression, premenstrual syndromes, substance abuse and withdrawal including overeating, and behavioral addictions including gambling. Furthermore, it is disclosed herein that the induction of euphoria may be used for purposes of anesthesia or as a sleep aid for insomnia.

In certain aspects of the description, a device or system comprises an energy source of magnetic and/or electrical energy that is transmitted to, or in close proximity to, the vagus nerve temporarily stimulate and/or modulate the signals in the nerve.

A method of treating or preventing a disorder in a patient according to the present description includes positioning a contact surface of a device in contact with an outer skin surface of a neck of the patient and applying, via the device, when the contact surface is in contact with the outer skin surface of the neck of the patient, an electrical impulse transcutaneously and non-invasively via the contact surface through the outer skin surface of the neck of the patient to a vagus nerve of the patient according to a treatment paradigm. In certain embodiments, the treatment paradigm is based at least in part on an application of the electrical impulse as a single dose every 4 to 5 hours during the day. In other embodiments, the treatment paradigm is based at least in part on an application of the electrical impulse as a single dose 2 to 5 times every day.

A vagus nerve stimulation treatment according to the present description is conducted for thirty seconds to five minutes, preferably about 90 seconds to about three minutes and more preferably about two minutes (each defined as a single dose). For prophylactic treatments, such as a treatment to avert a stroke or transient ischemic attack, the therapy preferably comprises multiple doses/day over a period of time that may last from one week to a number of years. In certain embodiments, the treatment will comprise multiple doses at predetermined times during the day and/or at predetermined intervals throughout the day. In exemplary embodiments, the treatment comprises one of the following: (1) 3 single doses/day at predetermined intervals or times; (2) two doses, either consecutively, or separated by 5 min at predetermined intervals or times, preferably two or three times/day; (3) 3 doses, either consecutively or separated by 5 min again at predetermined intervals or times, such as 2 or 3 times/day; or (4) 1-3 doses, either consecutively or separated by 5 min, 4-6 times per day. Initiation of a treatment may begin when an imminent stroke or TIA is forecasted, or in a risk-factor reduction program it may be performed throughout the day beginning after the patient arises in the morning.

For an acute treatment, such as treatment of acute stroke, the therapy may consist of: (1) 1 treatment at the onset of symptoms; (2) 1 treatment at the onset of symptoms, followed by another treatment at 5-15 min; or (3) 1 treatment every hour.

For long term treatment of an acute insult such as one that occurs during the rehabilitation of a stroke patient, the therapy may consist of: (1) 3 treatments/day; (2) 2 treatments, either consecutively or separated by 5 min, 3×/day; (3) 3 treatments, either consecutively or separated by 5 min, 2×/day; (4) 2 or 3 treatments, either consecutively or separated by 5 min, up to 10×/day; or (5) 1, 2 or 3 treatments, either consecutively or separated by 5 min, every 15, 30, 60 or 120 min. In an exemplary embodiment, each treatment session comprises 1-3 doses administered to the patient either consecutively or separated by 5 minutes. The treatment sessions are administered every 15, 30, 60 or 120 minutes during the day such that the patient could receive 2 doses every hour throughout a 24 hour day.

For all of the treatments listed above, one may alternate treatment between left and right sides, or in the case of stroke or migraine that occur in particular brain hemispheres, one may treat ipsilateral or contralateral to the stroke-hemisphere or headache side, respectively. Or for a single treatment, one may treat one minute on one side followed by one minute on the opposite side. Variations of these treatment paradigms may be chosen on a patient-by-patient basis. However, it is understood that parameters of the stimulation protocol may be varied in response to heterogeneity in the symptoms of patients. Different stimulation parameters may also be selected as the course of the patient's condition changes. In preferred embodiments, the disclosed methods and devices do not produce clinically significant side effects, such as agitation or anxiety, or changes in heart rate or blood pressure.

In certain embodiments, the vagal nerve stimulator of the present description is non-invasive. In one preferred embodiment, a method of treatment includes positioning the coil of a magnetic stimulator non-invasively on or above a patient's neck and applying a magnetically-induced electrical impulse non-invasively to the target region within the neck to stimulate or otherwise modulate selected nerve fibers. In another embodiment, surface electrodes are used to apply electrical impulses non-invasively to the target region within the neck to likewise stimulate or otherwise modulate selected nerve fibers. Preferably, the target region is adjacent to, or in close proximity with, the carotid sheath that contains a vagus nerve.

The non-invasive magnetic stimulator device is used to modulate electrical activity of a vagus nerve, without actually introducing a magnetic field into the patient. The preferred stimulator comprises two toroidal windings that lie side-by-side within separate stimulator heads, wherein the toroidal windings are separated by electrically insulating material. Each toroid is in continuous contact with an electrically conducting medium that extends from the patient's skin to the toroid. The currents passing through the coils of the magnetic stimulator will saturate its core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses, as described below, shaping an elongated electrical field of effect.

In another embodiment of the description, the stimulator comprises a source of electrical power and two or more remote electrodes that are configured to stimulate a deep nerve. The stimulator may comprise two electrodes that lie side-by-side within a hand-held enclosure, wherein the electrodes are separated by electrically insulating material. Each electrode is in continuous contact with an electrically conducting medium that extends from the interface element of the stimulator to the electrode. The interface element also contacts the patient's skin when the device is in operation.

Current passing through an electrode may be about 0 to about 40 mA, with voltage across the electrodes of about 0 to about 30 volts. The current is passed through the electrodes in bursts of pulses. There may be 1 to 20 pulses per burst, preferably five pulses. Each pulse within a burst has a duration of about 20 to about 1000 microseconds, preferably about 200 microseconds. A burst followed by a silent inter-burst interval repeats at 1 to 5000 bursts per second (bps, similar to Hz), preferably at 15-50 bps, and even more preferably at 25 bps. The preferred shape of each pulse is a full sinusoidal wave.

A source of power supplies a pulse of electric charge to the electrodes or magnetic stimulator coil, such that the electrodes or magnetic stimulator produce an electric current and/or an electric field within the patient. The electrical or magnetic stimulator is configured to induce a peak pulse voltage sufficient to produce an electric field in the vicinity of a nerve such as a vagus nerve, to cause the nerve to depolarize and reach a threshold for action potential propagation. By way of example, the threshold electric field for stimulation of the nerve may be about 8 V/m at 1000 Hz. For example, the device may produce an electric field within the patient of about 10 to about 600 V/m (preferably less than about 100 V/m) and an electrical field gradient of greater than about 2 V/m/mm. Electric fields that are produced at the vagus nerve are generally sufficient to excite all myelinated A and B fibers, but not necessarily the unmyelinated C fibers. However, by using a reduced amplitude of stimulation, excitation of A-delta and B fibers may also be avoided.

The preferred stimulator shapes an elongated electric field of effect that can be oriented parallel to a long nerve, such as a vagus. By selecting a suitable waveform to stimulate the nerve, along with suitable parameters such as current, voltage, pulse width, pulses per burst, inter-burst interval, etc., the stimulator produces a correspondingly selective physiological response in an individual patient. Such a suitable waveform and parameters are simultaneously selected to avoid substantially stimulating nerves and tissue other than the target nerve, particularly avoiding the stimulation of nerves in the skin that produce pain.

The novel systems, devices and methods for treating stroke and/or transient ischemic attacks are more completely described in the following detailed description of the description, with reference to the drawings provided herewith, and in claims appended hereto. Other aspects, features, advantages, etc. will become apparent to one skilled in the art when the description of the description herein is taken in conjunction with the accompanying drawings.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

BRIEF DESCRIPTION OF THE DRAWINGS

For the purposes of illustrating the various aspects of the description, there are shown in the drawings forms that are presently preferred, it being understood, however, that the description is not limited by or to the precise data, methodologies, arrangements and instrumentalities shown, but rather only by the claims.

FIG. 1B shows functional networks within the brain (resting state networks) that may be modulated by electrical stimulation of a vagus nerve.

FIG. 1C shows subcomponents of a resting state network that is responsible for movements of a stroke patient, as well as interconnections between those components.

FIG. 1D shows how interconnections between the subcomponents shown in FIG. 1C have changed in the stroke patient, relative to the interconnections prior to the stroke.

FIG. 2A is a schematic view of an exemplary nerve modulating device according to the present description which supplies controlled pulses of electrical current to a magnetic stimulator coil.

FIG. 2B is a schematic view of another embodiment of a nerve modulating device according to the present description which supplies electrical current to surface electrodes.

FIG. 3E illustrates the magnetic stimulator coil of FIGS. 3A-3D attached via cable to a box containing the device's impulse generator, control unit, and power source.

FIG. 4A is a perspective view of a dual-electrode stimulator according to another embodiment of the present description.

FIG. 4B is a cut-a-way view of the dual-electrode stimulator of FIG. 4A.

FIG. 6A illustrates the approximate position of the housing of the stimulator according one embodiment of the present description, when used to stimulate the right vagus nerve in the neck of an adult patient.

DETAILED DESCRIPTION OF THE PREFERRED EMBODIMENTS

Figure 1A:
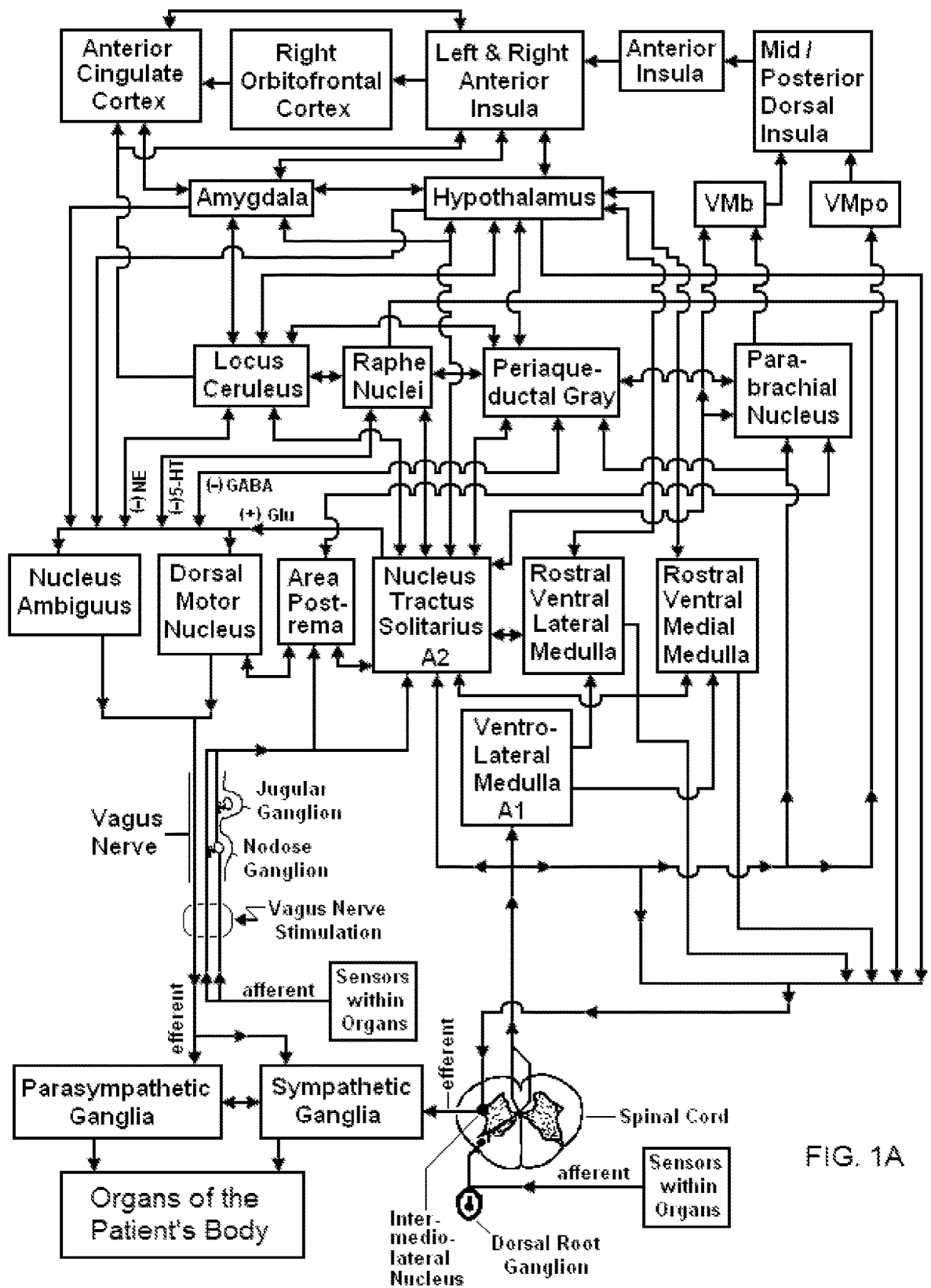
FIG. 1A shows structures within a patient's nervous system that may be modulated by electrical stimulation of a vagus nerve.

In some embodiments, numbers expressing frequencies, periods of time, or quantities or levels of current, voltage, energy, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In one or more embodiments of the present description, electrical energy is applied in a patient to a target region within or around the carotid sheath (also called the carotid neurovascular bundle) to treat a patient's ailment. The description is particularly useful for applying electrical impulses that ultimately interact with the signals of a vagus nerve, which lies within the carotid sheath, to achieve a therapeutic result. The nerve stimulation may result in benefits to the patient such as: relaxation of the smooth muscle of the bronchia for treatment of bronchoconstriction associated with asthma, COPD and/or exercised-induced bronchoconstriction, increase in blood pressure associated with orthostatic hypotension, reduction in blood pressure, treatment of epilepsy, treating ileus conditions, depression, anxiety, anaphylaxis, obesity, a neurodegenerative disorder such as Alzheimer's disease, migraine, tension-type, cluster, MOH and other types of headache, rhinitis, sinusitis, stroke, atrial fibrillation, autism, modulation of liver function, gastroparesis and other functional gastrointestinal disorders, and/or any other ailment that may be affected by nerve transmissions of a vagus nerve. Such treatments for different disorders are disclosed in the following US patent applications assigned to ElectroCore, LLC (the complete disclosures of which are incorporated by reference in their entirety for all purposes): U.S. patent application Ser. No. 13/858, 114, filed Apr. 8, 2013, U.S. patent application Ser. No. 13/783,391, filed Mar. 3, 2013, U.S. patent application Ser. No. 13/736,096, filed Jan. 8, 2013, U.S. patent application Ser. No. 13/731,035, filed Dec. 30, 2012, U.S. patent application Ser. No. 13/603,799 filed Sep. 5, 2012, U.S. patent application Ser. No. 13/357,010, filed Jan. 24, 2012, U.S. patent application Ser. No. 13/279,437 filed Oct. 24, 2011, U.S. patent application Ser. No. 13/222,087 filed Aug. 31, 2011, U.S. patent application Ser. No. 13/183,765 filed Jul. 15, 2011, U.S. patent application Ser. No. 13/183,721 filed Jul. 15, 2011, U.S. patent application Ser. No. 13/109,250 filed May 17, 2011, U.S. patent application Ser. No. 13/075, 746 filed Mar. 30, 2011, U.S. patent application Ser. No. 13/024,727, filed Feb. 10, 2011 (now U.S. Pat. No. 9,089, 719), U.S. patent application Ser. No. 13/005,005 filed Jan. 12, 2011, U.S. patent application Ser. No. 12/964,050 filed Dec. 9, 2010, U.S. patent application Ser. No. 12/859,568 filed Aug. 9, 2010, U.S. patent application Ser. No. 12/408, 131 filed Mar. 20, 2009 and U.S. patent application Ser. No. 12/612,177 filed Nov. 9, 2009 now U.S. Pat. No. 8,041,428 issued Oct. 18, 2011.

Methods are also disclosed for using the induced euphoria in individuals needing relief from mental and physical stress, depression, premenstrual syndromes, substance abuse and withdrawal including overeating, and behavioral addictions including gambling. Furthermore, it is disclosed herein that the induction of euphoria may be used for purposes of anesthesia or as a sleep aid for insomnia.

As discussed in U.S. Pat. No. 9,089,719, previously incorporated herein by reference, the term euphoria is used in multiple related senses, as evidenced by the definitions of the word "euphoria" that are given by different medical dictionaries: 1. a feeling or state of well-being or elation. 2. an exaggerated or abnormal sense of physical and emotional well-being not based on reality or truth, disproportionate to its cause, and inappropriate to the situation, as commonly seen in the manic stage of bipolar disorder, some forms of Schizophrenia, organic mental disorders, and toxic and drug-induced states. (Mosby's Medical Dictionary, 8th edition).

Elevated mood. Euphoria is a desirable and natural occurrence when it results from happy or exciting events. An excessive degree of euphoria that is not linked to events is characteristic of hypomania or mania, abnormal mood states associated with bipolar disorders. (MedTerms™ Medical Dictionary). A feeling of great happiness or well-being. Euphoria may be a side effect of certain drugs. (National Cancer Institute Dictionary of Cancer Terms).

An intense feeling of elation or well-being. Many marijuana users experience temporary euphoria. (Gale Encyclopedia of Medicine, 2008). A feeling of well-being or elation; especially: one that is groundless, disproportionate to its cause, or inappropriate to one's life situation. (Merriam-Webster's Medical Dictionary and Medline Plus of the U.S. National Library of Medicine). More nuanced definitions of the word euphoria may be made, by referring to particular populations of euphoric individuals, such as drug users who achieve euphoric states through use of drugs such as cocaine, cannabis, methamphetamines and their derivatives such as MDMA (ecstasy), as well as opioids and morphine derivatives Such as heroin. For drug users, different usages of the term may refer to a prolonged "high euphoric feeling, or alternatively to an acute euphoric feeling of "rush" William E. McAULIFFE and Robert A. Gordon. A Test of Lindesmith's Theory of Addiction: The Frequency of Euphoria Among Long-Term Addicts. The American Journal of Sociology 79 (4, 1974): 795-840. See pp. 800-803).

Estimation of the degree of euphoria may also be made by a trained observer using a standard Scale. Such as the following, which was used in experiments in which stimulating electrodes were implanted in various sites of subjects' brains: 1. The patient becomes relaxed, at ease, has a feeling of well-being, and/or may be a little sleepy (Positive I). 2. The patient is definitely changed, is in a good mood, and feels good. He is relaxed, at ease, and enjoying himself. He frequently smiles. There is slight euphoria, but the behavior is within normal limits. He may want more stimulations (Positive II). 3. The euphoria is definitely beyond normal limits. The patient laughs out loud, enjoys himself, positively likes the stimulation and wants more (Positive III). Alan E. Fuchs. The Production of Pleasure by Stimulation of the Brain: An Alleged Conflict Between Science and Philosophy. Philosophy and Phenomenological Research, 36 (4, 1976): 494-505.

Another method of ascertaining the degree of pleasure that is induced by a particular form of stimulation is the delphi method in which experts, experienced with many forms of pleasurable stimulation, are asked to rank or otherwise quantify the different forms of stimulation Nutt D. King L. A. Saulsbury W. Blakemore C. Development of a rational scale to assess the harm of drugs of potential misuse. Lancet 369 (2007): 1047-1053).

Ascertaining the euphoric individual's emotional state may also be made by the individual himself through the use of questionnaires such as the Addiction Research Center Inventory. The questionnaires may be used to distinguish different states of euphoria that are produced by different drugs, as well as by alcohol consumption C. A. HAERTZEN and J. E. Hickey (1987). Addiction Research Center Inventory (ARCI): Measurement of euphoria and other drug effects. In M. A. Bozarth (Ed.), Methods of assessing the reinforcing properties of abused drugs (pp. 489-524). New York: Springer-Verlag. The ARCI answer sheet is in true-false format, wherein the respondent answers many questions such as "I feel as if I would be more popular with people today' and "I feel drowsy. The totality of answers to those questions by an individual may be used to Sub-classify drug-induced euphoria according to drug types. Those Sub-classifications are presumably a reflection of the different neuronal circuits that are activated or inhibited by different drugs. Such circuits are described below in connection with the neurophysiology of euphoria. Scoring high on the "MBG' scale of the ARCI would be indicative of euphoria. Although it was designed for an evaluation of the effects of different drugs, the ARCI may be used for other forms of stimulation as well. For example, acupuncture has been found to increase MBG scores, although not to the extent that is associated with drugs in the MBG group (morphine, Benzedrine) Sheng-Xing Ma. Neurobiology of Acupuncture: Toward CAM. eCAM 2004; 1(1)41-47.

Hypomania may also be induced as a side effect of drugs. In particular, amphetamines that promote dopamine release and inhibit its reuptake have been shown to either precipitate hypomania in patients with bipolar disease or induce a "hypomanic-like' state in otherwise healthy subjects Wayne C. Drevets, Clara Gautier, Julie C. Price, David J. Kupfer, Paul E. Kinahan, Anthony A. Grace, Joseph L. Price, and Chester A. Mathis. Amphetamine-induced dopamine release in human ventralstriatum correlates with euphoria. Biol Psychiatry 49(2, 2001):81-96. If an individual has hypomanic symptoms without accompanying periods of depression or drug side effects, the individual may simply have a hypomania-like temperament or personality (e.g., an enthusiastic and outgoing workaholic, or an ENTJ personality according to the Myers-Briggs classification) Jules Angst. The emerging epidemiology of hypomania and bipolar II disorder. Journal of Affective Disorders 50 (1998) 143-151; Thomas Hugh Richardson. Hypomania: A brief review of conceptual and diagnostic issues. The New Zealand Medical Student Journal Number 10 (2009): 25-28.

The fact that electrical stimulation of a vagus nerve can be used to treat so many disorders may be understood as follows. The vagus nerve is composed of motor and sensory fibers. The vagus nerve leaves the cranium, passes down the neck within the carotid sheath to the root of the neck, then passes to the chest and abdomen, where it contributes to the innervation of the viscera. A human vagus nerve (tenth cranial nerve, paired left and right) consists of over 100,000 nerve fibers (axons), mostly organized into groups. The groups are contained within fascicles of varying sizes, which branch and converge along the nerve. Under normal physiological conditions, each fiber conducts electrical impulses only in one direction, which is defined to be the orthodromic direction, and which is opposite the antidromic direction. However, external electrical stimulation of the nerve may produce action potentials that propagate in orthodromic and antidromic directions. Besides efferent output fibers that convey signals to the various organs in the body from the central nervous system, the vagus nerve conveys sensory (afferent) information about the state of the body's organs back to the central nervous system. Some 80-90% of the nerve fibers in the vagus nerve are afferent (sensory) nerves, communicating the state of the viscera to the central nervous system.

The largest nerve fibers within a left or right vagus nerve are approximately 20 µm in diameter and are heavily myelinated, whereas only the smallest nerve fibers of less than about 1 µm in diameter are completely unmyelinated. When the distal part of a nerve is electrically stimulated, a compound action potential may be recorded by an electrode located more proximally. A compound action potential contains several peaks or waves of activity that represent the summated response of multiple fibers having similar conduction velocities. The waves in a compound action potential represent different types of nerve fibers that are classified into corresponding functional categories, with approximate diameters as follows: A-alpha fibers (afferent or efferent fibers, 12-20 µm diameter), A-beta fibers (afferent or efferent fibers, 5-12 µm), A-gamma fibers (efferent fibers, 3-7 µm), A-delta fibers (afferent fibers, 2-5 µm), B fibers (1-3 µm) and C fibers (unmyelinated, 0.4-1.2 µm). The diameters of group A and group B fibers include the thickness of the myelin sheaths.

The vagus (or vagal) afferent nerve fibers arise from cell bodies located in the vagal sensory ganglia, which take the form of swellings near the base of the skull. Vagal afferents traverse the brainstem in the solitary tract, with some eighty percent of the terminating synapses being located in the nucleus of the tractus solitarius (or nucleus tractus solitarii, nucleus tractus solitarius, or NTS). The NTS projects to a wide variety of structures in the central nervous system, such as the amygdala, raphe nuclei, periaqueductal gray, nucleus paragigantocellurlais, olfactory tubercule, locus ceruleus, nucleus ambiguus and the hypothalamus. The NTS also projects to the parabrachial nucleus, which in turn projects to the hypothalamus, the thalamus, the amygdala, the anterior insula, and infralimbic cortex, lateral prefrontal cortex, and other cortical regions [JEAN A. The nucleus tractus solitarius: neuroanatomic, neurochemical and functional aspects. Arch Int Physiol Biochim Biophys 99(5,1991):A3-A52]. Thus, stimulation of vagal afferents can modulate the activity of many structures of the brain and brainstem through these projections.

With regard to vagal efferent nerve fibers, two vagal components have evolved in the brainstem to regulate peripheral parasympathetic functions. The dorsal vagal complex, consisting of the dorsal motor nucleus and its connections controls parasympathetic function primarily below the level of the diaphragm, while the ventral vagal complex, comprised of nucleus ambiguus and nucleus retrofacial, controls functions primarily above the diaphragm in organs such as the heart, thymus and lungs, as well as other glands and tissues of the neck and upper chest, and specialized muscles such as those of the esophageal complex. For example, the cell bodies for the preganglionic parasympathetic vagal neurons that innervate the heart reside in the nucleus ambiguus, which is relevant to potential cardiovascular side effects that may be produced by vagus nerve stimulation.

The vagus efferent fibers innervate parasympathetic ganglionic neurons that are located in or adjacent to each target organ. The vagal parasympathetic tone resulting from the activity of these fibers is balanced reflexly in part by sympathetic innervations. Consequently, electrical stimulation of a vagus nerve may result not only in modulation of parasympathetic activity in postganglionic nerve fibers, but also a reflex modulation of sympathetic activity. The ability of a vagus nerve to bring about widespread changes in autonomic activity, either directly through modulation of vagal efferent nerves, or indirectly via activation of brainstem and brain functions that are brought about by electrical stimulation of vagal afferent nerves, accounts for the fact that vagus nerve stimulation can treat many different medical conditions in many end organs. Selective treatment of particular conditions is possible because the parameters of the electrical stimulation (frequency, amplitude, pulse width, etc.) may selectively activate or modulate the activity of particular afferent or efferent A, B, and/or C fibers that result in a particular physiological response in each individual.

As ordinarily practiced, the electrodes used to stimulate a vagus nerve are implanted about the nerve during open neck surgery. For many patients, this may be done with the objective of implanting permanent electrodes to treat epilepsy, depression, or other conditions [Arun Paul AMAR, Michael L. Levy, Charles Y. Liu and Michael L. J. Apuzzo. Chapter 50. Vagus nerve stimulation. pp. 625-638, particularly 634-635. In: Elliot S. Krames, P. Hunber Peckham, Ali R. Rezai, eds. Neuromodulation. London: Academic Press, 2009; KIRSE DJ, Werle A H, Murphy J V, Eyen T P, Bruegger D E, Hornig G W, Torkelson R D. Vagus nerve stimulator implantation in children. Arch Otolaryngol Head Neck Surg 128(11,2002):1263-1268]. In that case, the electrode is often a spiral electrode, although other designs may be used as well [U.S. Pat. No. 4,979,511, entitled Strain relief tether for implantable electrode, to TERRY, Jr.; U.S. Pat. No. 5,095,905, entitled Implantable neural electrode, to KLEPINSKI]. In other patients, a vagus nerve is electrically stimulated during open-neck thyroid surgery in order to confirm that the nerve has not been accidentally damaged during the surgery. In that case, a vagus nerve in the neck is surgically exposed, and a temporary stimulation electrode is clipped about the nerve [SCHNEIDER R, Randolph G W, Sekulla C, Phelan E, Thanh P N, Bucher M, Machens A, Dralle H, Lorenz K. Continuous intraoperative vagus nerve stimulation for identification of imminent recurrent laryngeal nerve injury. Head Neck. 2012 Nov. 20. doi: 10.1002/hed.23187 (Epub ahead of print, pp. 1-8)].

It is also possible to electrically stimulate a vagus nerve using a minimally invasive surgical approach, namely percutaneous nerve stimulation. In that procedure, a pair of electrodes (an active and a return electrode) are introduced through the skin of a patient's neck to the vicinity of a vagus nerve, and wires connected to the electrodes extend out of the patient's skin to a pulse generator [Publication number US20100241188, entitled Percutaneous electrical treatment of tissue, to J. P. ERRICO et al.; SEPULVEDA P, Bohill G, Hoffmann T J. Treatment of asthmatic bronchoconstriction by percutaneous low voltage vagal nerve stimulation: case report. Internet J Asthma Allergy Immunol 7(2009):e1 (pp 1-6); MINER, J. R., Lewis, L. M., Mosnaim, G. S., Varon, J., Theodoro, D. Hoffman, T. J. Feasibility of percutaneous vagus nerve stimulation for the treatment of acute asthma exacerbations. Acad Emerg Med 2012; 19: 421-429], the complete disclosures of which are incorporated herein by reference in their entirety for all purposes.

Percutaneous nerve stimulation procedures had previously been described primarily for the treatment of pain, but not for a vagus nerve, which is ordinarily not considered to produce pain and which presents special challenges [HUNTOON MA, Hoelzer B C, Burgher A H, Hurdle M F, Huntoon E A. Feasibility of ultrasound-guided percutaneous placement of peripheral nerve stimulation electrodes and anchoring during simulated movement: part two, upper extremity. Reg Anesth Pain Med 33(6,2008):558-565; CHAN I, Brown A R, Park K, Winfree C J. Ultrasound-guided, percutaneous peripheral nerve stimulation: technical note. Neurosurgery 67(3 Suppl Operative, 2010):ons136-139; MONTI E. Peripheral nerve stimulation: a percutaneous minimally invasive approach. Neuromodulation 7(3, 2004):193-196; Konstantin V SLAVIN. Peripheral nerve stimulation for neuropathic pain. US Neurology 7(2,2011): 144-148].

In one embodiment, the stimulation device is introduced through a percutaneous penetration in the patient to a target location within, adjacent to, or in close proximity with, the carotid sheath that contains the vagus nerve. Once in position, electrical impulses are applied through the electrodes of the stimulation device to one or more selected nerves (e.g., vagus nerve or one of its branches) to stimulate, block or otherwise modulate the nerve(s) and treat the patient's condition or a symptom of that condition. For some conditions, the treatment may be acute, meaning that the electrical impulse immediately begins to interact with one or more nerves to produce a response in the patient. In some cases, the electrical impulse will produce a response in the nerve(s) to improve the patient's condition or symptom in less than 3 hours, preferably less than 1 hour and more preferably less than 15 minutes. For other conditions, intermittently scheduled or as-needed stimulation of the nerve may produce improvements in the patient over the course of several days, weeks, months or years. A more complete description of a suitable percutaneous procedure for vagal nerve stimulation can be found in commonly assigned, co-pending US patent application titled "Percutaneous Electrical Treatment of Tissue", filed Apr. 13, 2009 (Ser. No. 12/422,483), the complete disclosure of which is hereby incorporated by reference in its entirety for all purposes.

In another embodiment of the description, a time-varying magnetic field, originating and confined to the outside of a patient, generates an electromagnetic field and/or induces eddy currents within tissue of the patient. In another embodiment, electrodes applied to the skin of the patient generate currents within the tissue of the patient. An objective of the description is to produce and apply the electrical impulses so as to interact with the signals of one or more nerves, in order to prevent or avert a stroke and/or transient ischemic attack, to ameliorate or limit the effects of an acute stroke or transient ischemic attack, and/or to rehabilitate a stroke patient.

Much of the disclosure will be directed specifically to treatment of a patient by electromagnetic stimulation in or around a vagus nerve, with devices positioned non-invasively on or near a patient's neck. However, it will also be appreciated that the devices and methods of the present description can be applied to other tissues and nerves of the body, including but not limited to other parasympathetic nerves, sympathetic nerves, spinal or cranial nerves. As recognized by those having skill in the art, the methods should be carefully evaluated prior to use in patients known to have preexisting cardiac issues. In addition, it will be recognized that the treatment paradigms of the present description can be used with a variety of different vagal nerve stimulators, including implantable and/or percutaneous stimulation devices, such as the ones described above.

FIG. 1A shows the location of the stimulation as "Vagus Nerve Stimulation," relative to its connections with other anatomical structures that are potentially affected by the stimulation. In different embodiments of the description, various brain and brainstem structures are preferentially modulated by the stimulation. These structures will be described in sections of the disclosure that follow, along with the rationale for modulating their activity as a prophylaxis or treatment for stroke or transient ischemic attack. As a preliminary matter, we first describe the vagus nerve itself and its most proximal connections, which are particularly relevant to the disclosure below of the electrical waveforms that are used to perform the stimulation.

The vagus nerve (tenth cranial nerve, paired left and right) is composed of motor and sensory fibers. The vagus nerve leaves the cranium, passes down the neck within the carotid sheath to the root of the neck, then passes to the chest and abdomen, where it contributes to the innervation of the viscera.

A vagus nerve in man consists of over 100,000 nerve fibers (axons), mostly organized into groups. The groups are contained within fascicles of varying sizes, which branch and converge along the nerve. Under normal physiological conditions, each fiber conducts electrical impulses only in one direction, which is defined to be the orthodromic direction, and which is opposite the antidromic direction. However, external electrical stimulation of the nerve may produce action potentials that propagate in orthodromic and antidromic directions. Besides efferent output fibers that convey signals to the various organs in the body from the central nervous system, the vagus nerve conveys sensory (afferent) information about the state of the body's organs back to the central nervous system. Some 80-90% of the nerve fibers in the vagus nerve are afferent (sensory) nerves, communicating the state of the viscera to the central nervous system. Propagation of electrical signals in efferent and afferent directions are indicated by arrows in FIG. 1A. If communication between structures is bidirectional, this is shown in FIG. 1A as a single connection with two arrows, rather than showing the efferent and afferent nerve fibers separately.

The largest nerve fibers within a left or right vagus nerve are approximately 20 μm in diameter and are heavily myelinated, whereas only the smallest nerve fibers of less than about 1 μm in diameter are completely unmyelinated. When the distal part of a nerve is electrically stimulated, a compound action potential may be recorded by an electrode located more proximally. A compound action potential contains several peaks or waves of activity that represent the summated response of multiple fibers having similar conduction velocities. The waves in a compound action potential represent different types of nerve fibers that are classified into corresponding functional categories, with approximate diameters as follows: A-alpha fibers (afferent or efferent fibers, 12-20 μm diameter), A-beta fibers (afferent or efferent fibers, 5-12 μm), A-gamma fibers (efferent fibers, 3-7 μm), A-delta fibers (afferent fibers, 2-5 μm), B fibers (1-3 μm) and C fibers (unmyelinated, 0.4-1.2 μm). The diameters of group A and group B fibers include the thickness of the myelin sheaths. It is understood that the anatomy of the vagus nerve is developing in newborns and infants, which accounts in part for the maturation of autonomic reflexes. Accordingly, it is also understood that the parameters of vagus nerve stimulation in the present description are chosen in such a way as to account for this age-related maturation [PEREYRA P M, Zhang W, Schmidt M, Becker L E. Development of myelinated and unmyelinated fibers of human vagus nerve during the first year of life. J Neurol Sci 110(1-2, 1992):107-113; SCHECHTMAN VL, Harper R M, Kluge K A. Development of heart rate variation over the first 6 months of life in normal infants. Pediatr Res 26(4,1989): 343-346].

The vagus (or vagal) afferent nerve fibers arise from cell bodies located in the vagal sensory ganglia. These ganglia take the form of swellings found in the cervical aspect of the vagus nerve just caudal to the skull. There are two such ganglia, termed the inferior and superior vagal ganglia. They are also called the nodose and jugular ganglia, respectively (See FIG. 1A). The jugular (superior) ganglion is a small ganglion on the vagus nerve just as it passes through the jugular foramen at the base of the skull. The nodose (inferior) ganglion is a ganglion on the vagus nerve located in the height of the transverse process of the first cervical vertebra.

Vagal afferents traverse the brainstem in the solitary tract, with some eighty percent of the terminating synapses being located in the nucleus of the tractus solitarius (or nucleus tractus solitarii, nucleus tractus solitarius, or NTS, see FIG. 1A). The NTS projects to a wide variety of structures in the central nervous system, such as the amygdala, raphe nuclei, periaqueductal gray, nucleus paragigantocellurlais, olfactory tubercule, locus ceruleus, nucleus ambiguus and the hypothalamus. The NTS also projects to the parabrachial nucleus, which in turn projects to the hypothalamus, the thalamus, the amygdala, the anterior insula, and infralimbic cortex, lateral prefrontal cortex, and other cortical regions [JEAN A. The nucleus tractus solitarius: neuroanatomic, neurochemical and functional aspects. Arch Int Physiol Biochim Biophys 99(5,1991):A3-A52]. Such central projections are discussed below in connection with the interoception and resting state neural networks.

With regard to vagal efferent nerve fibers, two vagal components have evolved in the brainstem to regulate peripheral parasympathetic functions. The dorsal vagal complex, consisting of the dorsal motor nucleus and its connections (see FIG. 1A), controls parasympathetic function primarily below the level of the diaphragm (e.g. gut and its enterochromaffin cells), while the ventral vagal complex, comprised of nucleus ambiguus and nucleus retrofacial, controls functions primarily above the diaphragm in organs such as the heart, thymus and lungs, as well as other glands and tissues of the neck and upper chest, and specialized muscles such as those of the esophageal complex. For example, the cell bodies for the preganglionic parasympathetic vagal neurons that innervate the heart reside in the nucleus ambiguus, which is relevant to potential cardiovascular side effects that may be produced by vagus nerve stimulation.

With the foregoing as preliminary information about the vagus nerve, the topics that are presented below in connection with the disclosure of the description include the following: (1) Overview of physiological mechanisms through which the disclosed vagus nerve stimulation methods may be used to modulate the neuronal circuitry of individuals at risk for, or who have experienced, a stroke and/or transient ischemic attack; (2) Description of Applicant's magnetic and electrode-based nerve stimulating devices, describing in particular the electrical waveform used to stimulate a vagus nerve; (3) Preferred embodiments of the magnetic stimulator; (4) Preferred embodiments of the electrode-based stimulator; (5) Application of the stimulators to the neck of the patient; (6) Use of the devices with feedback and feedforward to improve treatment of individual patients.

Overview of physiological mechanisms through which the disclosed vagus nerve stimulation methods may be used to modulate the neuronal circuitry of individuals individuals at risk for, or who have suffered, a stroke and/or transient ischemic attack We now disclose methods and devices for electrically stimulating a vagus nerve noninvasively, in order to provide medical treatment to an individual at risk for, or who has suffered, a stroke and/or transient ischemic attack. The disclosed methods and devices are an extension of methods and devices that have been developed for the treatment of other conditions, as follows. Non-invasive stimulation of the cervical vagus nerve (nVNS) is a novel technology for treating various central nervous system disorders, primarily by stimulating specific afferent fibers of the vagus nerve to modulate brain function. This technology has been demonstrated in animal and human studies to treat a wide range of central nervous system disorders including headache (chronic and acute cluster and migraine), epilepsy, bronchoconstriction, anxiety disorders, depression, rhinitis, fibromyalgia, irritable bowel syndrome, stroke, traumatic brain injury, PTSD, Alzheimer's disease, autism, and others. Applicants have discovered that a two-minute stimulation has effects that may last up to 8 hours or longer depending on the type and severity of indication.

Broadly speaking, applicant has determined that there are three components to the effects of nVNS on the brain. The strongest effect occurs during the two minute stimulation and results in significant changes in brain function that can be clearly seen as acute changes in autonomic function (e.g. measured using pupillometry, heart rate variability, galvanic skin response, or evoked potential) and activation and inhibition of various brain regions as shown in fMRI imaging studies. The second effect, of moderate intensity, lasts for 15 to 180 minutes after stimulation. Animal studies have shown changes in neurotransmitter levels in various parts of the brain that persist for several hours. The third effect, of mild intensity, lasts up to 8 hours and is responsible for the long lasting alleviation of symptoms seen clinically and, for example, in animal models of migraine headache.

Thus, depending on the medical indication, whether it is a chronic or acute treatment, and the natural history of the disease, different treatment protocols may be used. In particular, applicant has discovered that it is not necessary to "continuously stimulate" the vagus nerve (or to in order to provide clinically efficacious benefits to patients with certain disorders. The term "continuously stimulate" as defined herein means stimulation that follows a certain On/Off pattern continuously 24 hours/day. For example, existing implantable vagal nerve stimulators "continuously stimulate" the vagus nerve with a pattern of 30 seconds ON/5 minutes OFF (or the like) for 24 hours/day and seven days/week. Applicant has determined that this continuous stimulation is not necessary to provide the desired clinical benefit for many disorders. For example, in the treatment of acute migraine attacks, the treatment paradigm may comprise two minutes of stimulation at the onset of pain, followed by another two minute stimulation 15 minutes later. For epilepsy, three 2 minute stimulations three times per day appear to be optimal. Sometimes, multiple consecutive, two minute stimulations are required. Thus, the initial treatment protocol corresponds to what may be optimum for the population of patients at large for a given condition. However, the treatment may then be modified on an individualized basis, depending on the response of each particular patient.

The present description contemplates three types of interventions involving stimulation of a vagus nerve: prophylactic, acute and compensatory (rehabilitative). Among these, the acute treatment involves the fewest administrations of vagus nerve stimulations, which begin upon the appearance of symptoms. It is intended primarily to enlist and engage the autonomic nervous system to inhibit excitatory neurotransmissions that accompany the symptoms. The prophylactic treatment resembles the acute treatment in the sense that it is administered as though acute symptoms had just occurred (even though they have not) and is repeated at regular intervals, as though the symptoms were reoccurring (even though they are not). The rehabilitative or compensatory treatments, on the other hand, seek to promote long-term adjustments in the central nervous system, compensating for deficiencies that arose as the result of the patient's disease by making new neural circuits.

A vagus nerve stimulation treatment according to the present description is conducted for continuous period of thirty seconds to five minutes, preferably about 90 seconds to about three minutes and more preferably about two minutes (each defined as a single dose). After a dose has been completed, the therapy is stopped for a period of time (depending on the treatment as described below). For prophylactic treatments, such as a treatment to avert a stroke or transient ischemic attack, the therapy preferably comprises multiple doses/day over a period of time that may last from one week to a number of years. In certain embodiments, the treatment will comprise multiple doses at predetermined times during the day and/or at predetermined intervals throughout the day. In exemplary embodiments, the treatment comprises one of the following: (1) 3 doses/day at predetermined intervals or times; (2) two doses, either consecutively, or separated by 5 min at predetermined intervals or times, preferably two or three times/day; (3) 3 doses, either consecutively or separated by 5 min again at predetermined intervals or times, such as 2 or 3 times/day; or (4) 1-3 doses, either consecutively or separated by 5 min, 4-6 times per day. Initiation of a treatment may begin when an imminent stroke or TIA is forecasted, or in a risk-factor reduction program it may be performed throughout the day beginning after the patient arises in the morning.

In an exemplary embodiment, each treatment session comprises 1-3 doses administered to the patient either consecutively or separated by 5 minutes. The treatment sessions are administered every 15, 30, 60 or 120 minutes during the day such that the patient could receive 2 doses every hour throughout a 24 hour day.

For certain disorders, the time of day can be more important than the time interval between treatments. For example, the locus coreless has periods of time during a 24 hour day wherein it has inactive periods and active periods. Typically, the inactive periods can occur in the late afternoon or in the middle of the night when the patient is asleep. It is during the inactive periods that the levels of inhibitory neurotransmitters in the brain that are generated by the locus coreless are reduced. This may have an impact on certain disorders. For example, patients suffering from migraines or cluster headaches often receive these headaches after an inactive period of the locus coreless. For these types of disorders, the prophylactic treatment is optimal during the inactive periods such that the amounts of inhibitory neurotransmitters in the brain can remain at a higher enough level to mitigate or abort an acute attack of the disorder.

In these embodiments, the prophylatic treatment may comprise multiple doses/day timed for periods of inactivity of the locus coreless. In one embodiment, a treatment according to the present description comprises one or more doses administered 2-3 times per day or 2-3 "treatment sessions" per day. The treatment sessions preferably occur during the late afternoon or late evening, in the middle of the night and again in the morning when the patient wakes up. In an exemplary embodiment, each treatment session comprises 1-4 doses, preferably 2-3 doses, with each dose lasting for about 90 seconds to about three minutes.

For other disorders, the intervals between treatment sessions may be the most important as applicant has determined that stimulation of the vagus nerve can have a prolonged effect on the inhibitor neurotransmitters levels in the brain, e.g., at least one hour, up to 3 hours and sometimes up to 8 hours. In one embodiment, a treatment according to the present description comprises one or more doses (i.e., treatment sessions) administered at intervals during a 24 hour period. In a preferred embodiment, there are 1-5 such treatment sessions, preferably 2-4 treatment sessions. Each treatment session preferably comprises 1-3 doses, each lasting between about 60 seconds to about three minutes, preferably about 90 seconds to about 150 seconds, more preferably about 2 minutes.

For an acute treatment, such as treatment of acute stroke, the therapy according to the present description may comprise one or more embodiments: (1) 1 dose at the onset of symptoms; (2) 1 dose at the onset of symptoms, followed by another dose at 5-15 min; or (3) 1 dose every 15 minutes to 1 hour at the onset of symptoms until the acute attack has been mitigated or aborted. In these embodiments, each dose preferably last between about 60 seconds to about three minutes, preferably about 90 seconds to about 150 seconds, more preferably about 2 minutes.

For long term treatment of an acute insult such as one that occurs during the rehabilitation of a stroke patient, the therapy may consist of: (1) 3 treatments/day; (2) 2 treatments, either consecutively or separated by 5 min, 3x/day; (3) 3 treatments, either consecutively or separated by 5 min, 2x/day; (4) 2 or 3 treatments, either consecutively or separated by 5 min, up to 10x/day; or (5) 1, 2 or 3 treatments, either consecutively or separated by 5 min, every 15, 30, 60 or 120 min.

For all of the treatments listed above, one may alternate treatment between left and right sides, or in the case of stroke or migraine that occur in particular brain hemispheres, one may treat ipsilateral or contralateral to the stroke-hemisphere or headache side, respectively. Or for a single treatment, one may treat one minute on one side followed by one minute on the opposite side. Variations of these treatment paradigms may be chosen on a patient-by-patient basis. However, it is understood that parameters of the stimulation protocol may be varied in response to heterogeneity in the symptoms of patients. Different stimulation parameters may also be selected as the course of the patient's condition changes. In preferred embodiments, the disclosed methods and devices do not produce clinically significant side effects, such as agitation or anxiety, or changes in heart rate or blood pressure.

The prophylactic treatments may be most effective when the patient is in a prodromal, high-risk bistable state. In that state, the patient is simultaneously able to remain normal or exhibit symptoms, and the selection between normal and symptomatic states depends on the amplification of fluctuations by physiological feedback networks. For example, a thrombus may exist in either a gel or fluid phase, with the feedback amplification of fluctuations driving the change of phase and/or the volume of the gel phase. Thus, a thrombus may form or not, depending on the nonlinear dynamics exhibited by the network of enzymes involved in clot formation, as influenced by blood flow and inflammation that may be modulated by vagus nerve stimulation [PANTELEEV M A, Balandina A N, Lipets E N, Ovanesov M V, Ataullakhanov F I. Task-oriented modular decomposition of biological networks: trigger mechanism in blood coagulation. Biophys J 98(9,2010):1751-1761; Alexey M SHIBEKO, Ekaterina S Lobanova, Mikhail A Panteleev and Fazoil I Ataullakhanov. Blood flow controls coagulation onset via the positive feedback of factor VII activation by factor Xa. BMC Syst Biol 2010; 4(2010):5, pp. 1-12]. Consequently, the mechanisms of vagus nerve stimulation treatment during prophylaxis for a stroke are generally different than what occurs during an acute treatment, when the stimulation inhibits excitatory neurotransmission that follows the onset of ischemia that is already caused by the thrombus. Nevertheless, the prophylactic treatment may also inhibit excitatory neurotransmission so as to limit the excitation that would eventually occur upon formation of a thrombus, and the acute treatment may prevent the formation of another thrombus.

The circuits involved in such inhibition are illustrated in FIG. 1A. Excitatory nerves within the dorsal vagal complex generally use glutamate as their neurotransmitter. To inhibit neurotransmission within the dorsal vagal complex, the present description makes use of the bidirectional connections that the nucleus of the solitary tract (NTS) has with structures that produce inhibitory neurotransmitters, or it makes use of connections that the NTS has with the hypothalamus, which in turn projects to structures that produce inhibitory neurotransmitters. The inhibition is produced as the result of the stimulation waveforms that are described below. Thus, acting in opposition to glutamate-mediated activation by the NTS of the area postrema and dorsal motor nucleus are: GABA, and/or serotonin, and/or norepinephrine from the periaqueductal gray, raphe nucei, and locus coeruleus, respectively. FIG. 1A shows how those excitatory and inhibitory influences combine to modulate the output of the dorsal motor nucleus. Similar influences combine within the NTS itself, and the combined inhibitory influences on the NTS and dorsal motor nucleus produce a general inhibitory effect.

The activation of inhibitory circuits in the periaqueductal gray, raphe nucei, and locus coeruleus by the hypothalamus or NTS may also cause circuits connecting each of these structures to modulate one another. Thus, the periaqueductal gray communicates with the raphe nuclei and with the locus coeruleus, and the locus coeruleus communicates with the raphe nuclei, as shown in FIG. 1A [PUDOVKINA O L, Cremers T I, Westerink B H. The interaction between the locus coeruleus and dorsal raphe nucleus studied with dual-probe microdialysis. Eur J Pharmacol 7(2002); 445(1-2):37-42.; REICHLING D B, Basbaum A I. Collateralization of periaqueductal gray neurons to forebrain or diencephalon and to the medullary nucleus raphe magnus in the rat. Neuroscience 42(1,1991):183-200; BEHBEHANI MM. The role of acetylcholine in the function of the nucleus raphe magnus and in the interaction of this nucleus with the periaqueductal gray. Brain Res 252(2,1982):299-307]. The periaqueductal gray, raphe nucei, and locus coeruleus also project to many other sites within the brain, including those that would be excited during ischemia. Therefore, in this aspect of the description, vagus nerve stimulation during acute stroke or transient ischemic attack has a general neuroprotective, inhibitory effect via its activation of the periaqueductal gray, raphe nucei, and locus coeruleus.

In particular, the vagus nerve stimulation may be neuroprotective to a part of the brain known as the insula (also known as the insularly cortex, insular cortex, or insular lobe) and its connections with the anterior cingulate cortex (ACC). Neural circuits leading from the vagus nerve to the insula and ACC are shown in FIG. 1A. Protection of the insula is particularly important for stroke patients, because damage to the insula is known to cause symptoms that are typical in stroke patients, involving motor control, hand and eye motor movement, motor learning, swallowing, speech articulation, the capacity for long and complex spoken sentences, sensation, and autonomic functions [ANDERSON TJ, Jenkins I H, Brooks D J, Hawken M B, Frackowiak R S, Kennard C. Cortical control of saccades and fixation in man. A PET study. Brain 117(5,1994):1073-1084; FINK GR, Frackowiak R S, Pietrzyk U, Passingham R E (April 1997). Multiple nonprimary motor areas in the human cortex. J. Neurophysiol 77 (4,1997): 2164-2174; SOROS P, Inamoto Y, Martin R E. Functional brain imaging of swallowing: an activation likelihood estimation meta-analysis. Hum Brain Mapp 30(8,2009):2426-2439; DRONKERS NF. A new brain region for coordinating speech articulation. Nature 384 (6605,1996): 159-161; ACKERMANN H, Riecker A. The contribution of the insula to motor aspects of speech production: a review and a hypothesis. Brain Lang 89 (2,2004): 320-328; BOROVSKY A, Saygin A P, Bates E, Dronkers N. Lesion correlates of conversational speech production deficits. Neuropsychologia 45 (11,2007): 2525-2533; OPPENHEIMER SM, Kedem G, Martin W M. Left-insular cortex lesions perturb cardiac autonomic tone in humans. Clin Auton Res; 6(3,1996):131-140; CRITCHLEY HD. Neural mechanisms of autonomic, affective, and cognitive integration. J. Comp. Neurol. 493 (1,2005): 154-166].

FIG. 1C illustrates one example of the present description for treating a patient suffering from stroke, illustrating exemplary connections between components of the SMN. Components shown there are: cerebellum (Cereb), primary motor cortex (M1), prefrontal cortex (PFC), lateral premotor cortex (PMC), supplementary motor area (SMA), superior parietal cortex (SPC) and thalamus (Thai). As also shown there, the components are paired within the brain, and the components in the left half of the figure represent the ones in the brain hemisphere that are affected by the stroke. FIG. 1D shows increases and decreases in excitatory and inhibitory interactions among these components, relative to connections in the SMN prior to the stroke. As in FIG. 1C, components in the left half of the figure are the ones in the brain hemisphere that are affected by the stroke [REHME AK, Grefkes C. Cerebral network disorders after stroke: evidence from imaging-based connectivity analyses of active and resting brain states in humans. J Physiol 591(Pt 1, 2013):17-31; INMAN CS, James G A, Hamann S, Rajendra J K, Pagnoni G, Butler A J. Altered resting-state effective connectivity of fronto-parietal motor control systems on the primary motor network following stroke. Neuroimage 59(1, 2012):227-237].

It is understood that additional SMA components are involved in specialized muscle movements. For example, the components most involved in the loss and recovery of speech following a stroke are the supplementary motor area (SMA, see FIGS. 1C and 1D) and its interaction with the right Broca-homologue (not shown) [SAUR D, Lange R, Baumgaertner A, Schraknepper V, Willmes K, Rijntjes M, Weiller C. Dynamics of language reorganization after stroke. Brain 129(2006):1371-1384].

Description of preferred embodiments of magnetic and electrode-based nerve stimulating/modulating devices Devices of the description that are used to stimulate a vagus nerve will now be described. Either a magnetic stimulation device or an electrode-based device may be used for that purpose. FIG. 2A is a schematic diagram of Applicant's magnetic nerve stimulating/modulating device 301 for delivering impulses of energy to nerves for the treatment of medical conditions. As shown, device 301 may include an impulse generator 310; a power source 320 coupled to the impulse generator 310; a control unit 330 in communication with the impulse generator 310 and coupled to the power source 320; and a magnetic stimulator coil 341 coupled via wires to impulse generator coil 310. The stimulator coil 341 is toroidal in shape, due to its winding around a toroid of core material.

Although the magnetic stimulator coil 341 is shown in FIG. 2A to be a single coil, in practice the coil may also comprise two or more distinct coils, each of which is connected in series or in parallel to the impulse generator 310. Thus, the coil 341 that is shown in FIG. 2A represents all the magnetic stimulator coils of the device collectively. In a preferred embodiment that is discussed below, coil 341 actually contains two coils that may be connected either in series or in parallel to the impulse generator 310.

The item labeled in FIG. 2A as 351 is a volume, surrounding the coil 341, that is filled with electrically conducting medium. As shown, the medium not only encloses the magnetic stimulator coil, but is also deformable such that it is form-fitting when applied to the surface of the body. Thus, the sinuousness or curvature shown at the outer surface of the electrically conducting medium 351 corresponds also to sinuousness or curvature on the surface of the body, against which the conducting medium 351 is applied, so as to make the medium and body surface contiguous. As time-varying electrical current is passed through the coil 341, a magnetic field is produced, but because the coil winding is toroidal, the magnetic field is spatially restricted to the interior of the toroid. An electric field and eddy currents are also produced. The electric field extends beyond the toroidal space and into the patient's body, causing electrical currents and stimulation within the patient. The volume 351 is electrically connected to the patient at a target skin surface in order to significantly reduce the current passed through the coil 341 that is needed to accomplish stimulation of the patient's nerve or tissue. In a preferred embodiment of the magnetic stimulator that is discussed below, the conducting medium with which the coil 341 is in contact need not completely surround the toroid.

The design of the magnetic stimulator 301, which is also adapted herein for use with surface electrodes, makes it possible to shape the electric field that is used to selectively stimulate a relatively deep nerve such as a vagus nerve in the patient's neck. Furthermore, the design produces significantly less pain or discomfort (if any) to a patient, at the site of stimulation on the skin, than stimulator devices that are currently known in the art. Conversely, for a given amount of pain or discomfort on the part of the patient (e.g., the threshold at which such discomfort or pain begins), the design achieves a greater depth of penetration of the stimulus under the skin.

An alternate embodiment of the present description is shown in FIG. 2B, which is a schematic diagram of an electrode-based nerve stimulating/modulating device 302 for delivering impulses of energy to nerves for the treatment of medical conditions. As shown, device 302 may include an impulse generator 310; a power source 320 coupled to the impulse generator 310; a control unit 330 in communication with the impulse generator 310 and coupled to the power source 320; and electrodes 340 coupled via wires 345 to impulse generator 310. In a preferred embodiment, the same impulse generator 310, power source 320, and control unit 330 may be used for either the magnetic stimulator 301 or the electrode-based stimulator 302, allowing the user to change parameter settings depending on whether coils 341 or the electrodes 340 are attached.

Although a pair of electrodes 340 is shown in FIG. 2B, in practice the electrodes may also comprise three or more distinct electrode elements, each of which is connected in series or in parallel to the impulse generator 310. Thus, the electrodes 340 that are shown in FIG. 2B represent all electrodes of the device collectively.

The item labeled in FIG. 2B as 350 is a volume, contiguous with an electrode 340, that is filled with electrically conducting medium. As described below in connection with particular embodiments of the description, conducting medium in which the electrode 340 is embedded need not completely surround an electrode. As also described below in connection with a preferred embodiment, the volume 350 is electrically connected to the patient at a target skin surface in order to shape the current density passed through an electrode 340 that is needed to accomplish stimulation of the patient's nerve or tissue. The electrical connection to the patient's skin surface is through an interface 351. In one embodiment, the interface is made of an electrically insulating (dielectric) material, such as a thin sheet of Mylar. In that case, electrical coupling of the stimulator to the patient is capacitive. In other embodiments, the interface comprises electrically conducting material, such as the electrically conducting medium 350 itself, or an electrically conducting or permeable membrane. In that case, electrical coupling of the stimulator to the patient is ohmic. As shown, the interface may be deformable such that it is form-fitting when applied to the surface of the body. Thus, the sinuousness or curvature shown at the outer surface of the interface 351 corresponds also to sinuousness or curvature on the surface of the body, against which the interface 351 is applied, so as to make the interface and body surface contiguous.

The control unit 330 controls the impulse generator 310 to generate a signal for each of the device's coils or electrodes. The signals are selected to be suitable for amelioration of a particular medical condition, when the signals are applied non-invasively to a target nerve or tissue via the coil 341 or electrodes 340. It is noted that nerve stimulating/modulating device 301 or 302 may be referred to by its function as a pulse generator. Patent application publications US2005/0075701 and US2005/0075702, both to SHAFER, contain descriptions of pulse generators that may be applicable to the present description. By way of example, a pulse generator is also commercially available, such as Agilent 33522A Function/Arbitrary Waveform Generator, Agilent Technologies, Inc., 5301 Stevens Creek Blvd Santa Clara CA 95051.

The control unit 330 may also comprise a general purpose computer, comprising one or more CPU, computer memories for the storage of executable computer programs (including the system's operating system) and the storage and retrieval of data, disk storage devices, communication devices (such as serial and USB ports) for accepting external signals from the system's keyboard, computer mouse, and touchscreen, as well as any externally supplied physiological signals (see FIG. 8), analog-to-digital converters for digitizing externally supplied analog signals (see FIG. 8), communication devices for the transmission and receipt of data to and from external devices such as printers and modems that comprise part of the system, hardware for generating the display of information on monitors that comprise part of the system, and busses to interconnect the above-mentioned components. Thus, the user may operate the system by typing instructions for the control unit 330 at a device such as a keyboard and view the results on a device such as the system's computer monitor, or direct the results to a printer, modem, and/or storage disk. Control of the system may be based upon feedback measured from externally supplied physiological or environmental signals. Alternatively, the control unit 330 may have a compact and simple structure, for example, wherein the user may operate the system using only an on/off switch and power control wheel or knob.

Parameters for the nerve or tissue stimulation include power level, frequency and train duration (or pulse number). The stimulation characteristics of each pulse, such as depth of penetration, strength and selectivity, depend on the rise time and peak electrical energy transferred to the electrodes or coils, as well as the spatial distribution of the electric field that is produced by the electrodes or coils. The rise time and peak energy are governed by the electrical characteristics of the stimulator and electrodes or coils, as well as by the anatomy of the region of current flow within the patient. In one embodiment of the description, pulse parameters are set in such as way as to account for the detailed anatomy surrounding the nerve that is being stimulated [Bartosz SAWICKI, Robert Szmurło, Przemystaw Płonecki, Jacek Starzyński, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. Pulses may be monophasic, biphasic or polyphasic. Embodiments of the description include those that are fixed frequency, where each pulse in a train has the same inter-stimulus interval, and those that have modulated frequency, where the intervals between each pulse in a train can be varied.

Figure 2C:
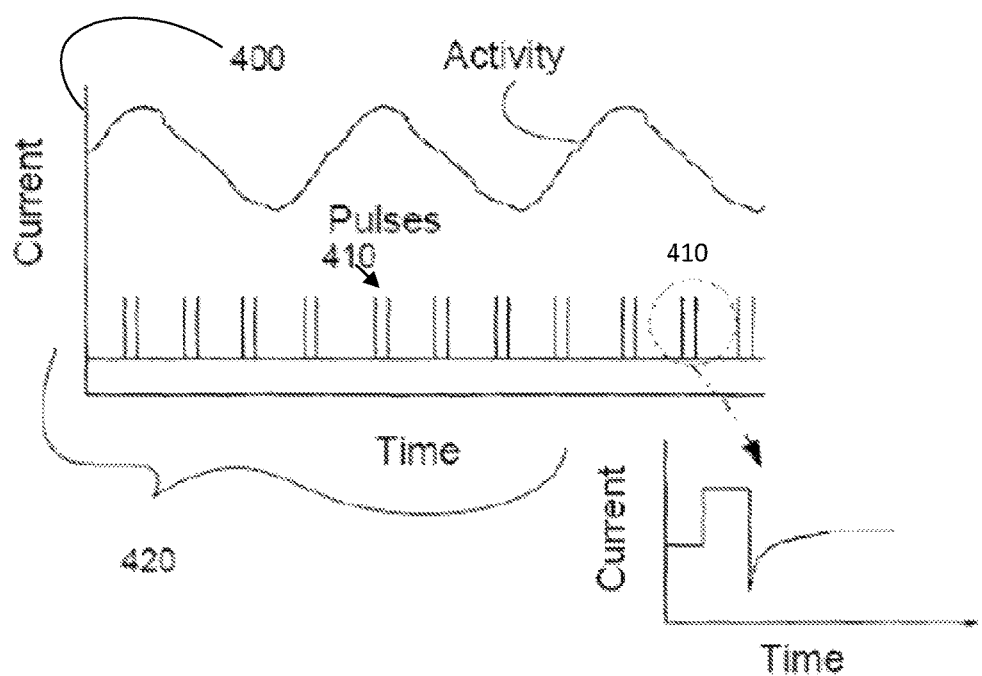
FIG. 2C illustrates an exemplary electrical voltage/current profile according to the present description.

FIG. 2C illustrates an exemplary electrical voltage/current profile for a stimulating, blocking and/or modulating impulse applied to a portion or portions of selected nerves in accordance with an embodiment of the present description. For the preferred embodiment, the voltage and current refer to those that are non-invasively produced within the patient by the stimulator coils or electrodes. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the coil 341 or electrodes 340 that deliver the stimulating, blocking and/or modulating impulse 410 to the nerve. Nerve stimulating/modulating device 301 or 302 may be externally powered and/or recharged or may have its own power source 320. The parameters of the modulation signal 400, such as the frequency, amplitude, duty cycle, pulse width, pulse shape, etc., are preferably programmable. An external communication device may modify the pulse generator programming to improve treatment.

In addition, or as an alternative to the devices to implement the modulation unit for producing the electrical voltage/current profile of the stimulating, blocking and/or modulating impulse to the electrodes or coils, the device disclosed in patent publication No. US2005/0216062 may be employed. That patent publication discloses a multifunctional electrical stimulation (ES) system adapted to yield output signals for effecting electromagnetic or other forms of electrical stimulation for a broad spectrum of different biological and biomedical applications, which produce an electric field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated, as well as the outputs of various sensors which sense prevailing conditions prevailing in this substance, whereby the user of the system can manually adjust the signal, or have it automatically adjusted by feedback, to provide an electrical stimulation signal of whatever type the user wishes, who can then observe the effect of this signal on a substance being treated.

The stimulating and/or modulating impulse signal 410 preferably has a frequency, an amplitude, a duty cycle, a pulse width, a pulse shape, etc. selected to influence the therapeutic result, namely, stimulating and/or modulating some or all of the transmission of the selected nerve. For example, the frequency may be about 1 Hz or greater, such as between about 15 Hz to about 100 Hz, preferably between about 15-50 Hz and more preferably between about 15-35 Hz. In an exemplary embodiment, the frequency is about 25 Hz. The modulation signal may have a pulse width selected to influence the therapeutic result, such as about 1 microseconds to about 1000 microseconds, preferably about 100-400 microseconds and more preferably about 200-400 microseconds. For example, the electric field induced or produced by the device within tissue in the vicinity of a nerve may be about 5 to about 600 V/m, preferably less than about 100 V/m, and even more preferably less than about 30 V/m. The gradient of the electric field may be greater than about 2 V/m/mm. More generally, the stimulation device produces an electric field in the vicinity of the nerve that is sufficient to cause the nerve to depolarize and reach a threshold for action potential propagation, which is about 8 V/m at 1000 Hz. The modulation signal may have a peak voltage amplitude selected to influence the therapeutic result, such as about 0.2 volts or greater, such as about 0.2 volts to about 40 volts, preferably between about 1-20 volts and more preferably between about 2-12 volts.

An objective of the disclosed stimulators is to provide both nerve fiber selectivity and spatial selectivity. Spatial selectivity may be achieved in part through the design of the electrode or coil configuration, and nerve fiber selectivity may be achieved in part through the design of the stimulus waveform, but designs for the two types of selectivity are intertwined. This is because, for example, a waveform may selectively stimulate only one of two nerves whether they lie close to one another or not, obviating the need to focus the stimulating signal onto only one of the nerves [GRILL W and Mortimer J T. Stimulus waveforms for selective neural stimulation. IEEE Eng. Med. Biol. 14 (1995): 375-385]. These methods complement others that are used to achieve selective nerve stimulation, such as the use of local anesthetic, application of pressure, inducement of ischemia, cooling, use of ultrasound, graded increases in stimulus intensity, exploiting the absolute refractory period of axons, and the application of stimulus blocks [John E. SWETT and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-295].

To date, the selection of stimulation waveform parameters for nerve stimulation has been highly empirical, in which the parameters are varied about some initially successful set of parameters, in an effort to find an improved set of parameters for each patient. A more efficient approach to selecting stimulation parameters might be to select a stimulation waveform that mimics electrical activity in the anatomical regions that one is attempting stimulate indirectly, in an effort to entrain the naturally occurring electrical waveform, as suggested in patent number U.S. Pat. No. 6,234,953, entitled Electrotherapy device using low frequency magnetic pulses, to THOMAS et al. and application number US20090299435, entitled Systems and methods for enhancing or affecting neural stimulation efficiency and/or efficacy, to GLINER et al. One may also vary stimulation parameters iteratively, in search of an optimal setting [U.S. Pat. No. 7,869,885, entitled Threshold optimization for tissue stimulation therapy, to BEGNAUD et al]. However, some stimulation waveforms, such as those described herein, are discovered by trial and error, and then deliberately improved upon.

Invasive nerve stimulation typically uses square wave pulse signals. However, Applicant found that square waveforms are not ideal for non-invasive stimulation as they produce excessive pain. Prepulses and similar waveform modifications have been suggested as methods to improve selectivity of nerve stimulation waveforms, but Applicant did not find them ideal [Aleksandra VUCKOVIC, Marco Tosato and Johannes J Struijk. A comparative study of three techniques for diameter selective fiber activation in the vagal nerve: anodal block, depolarizing prepulses and slowly rising pulses. J. Neural Eng. 5 (2008): 275-286; Aleksandra VUCKOVIC, Nico J. M. Rijkhoff, and Johannes J. Struijk. Different Pulse Shapes to Obtain Small Fiber Selective Activation by Anodal Blocking—A Simulation Study. IEEE Transactions on Biomedical Engineering 51(5, 2004):698-706; Kristian HENNINGS. Selective Electrical Stimulation of Peripheral Nerve Fibers: Accommodation Based Methods. Ph.D. Thesis, Center for Sensory-Motor Interaction, Aalborg University, Aalborg, Denmark, 2004].

Figure 2D:
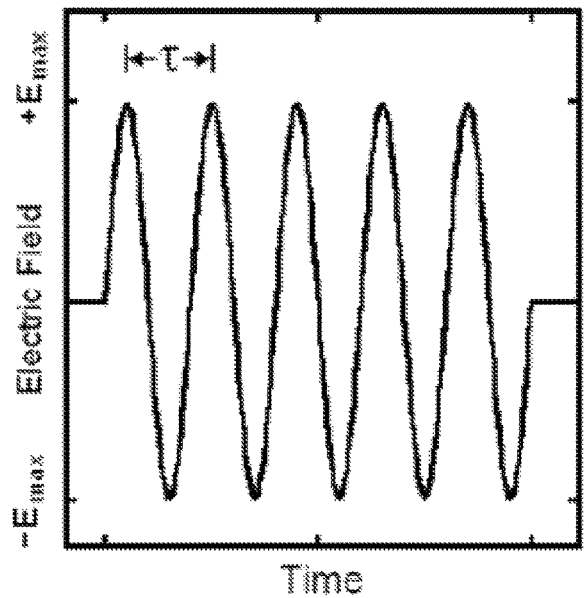
FIG. 2D illustrates an exemplary waveform for stimulating and/or modulating impulses that are applied to a nerve.
Figure 2E:
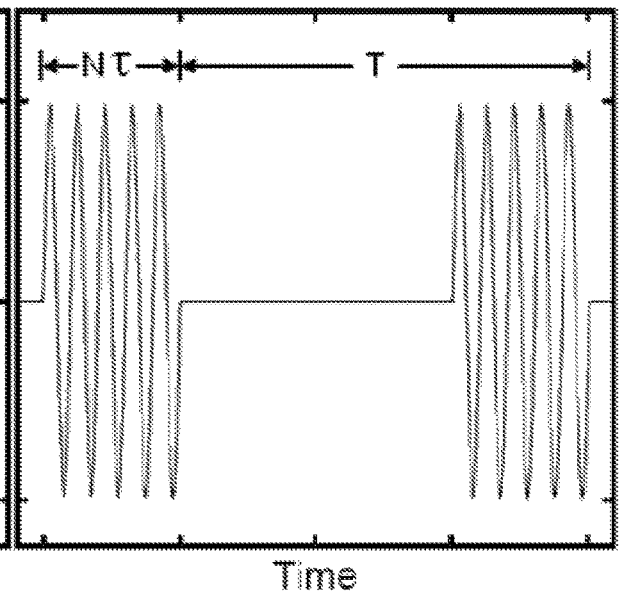
FIG. 2E illustrates another exemplary waveform for stimulating and/or modulating impulses applied to a nerve.

Applicant also found that stimulation waveforms consisting of bursts of square pulses are not ideal for non-invasive stimulation [M. I. JOHNSON, C. H. Ashton, D. R. Bousfield and J. W. Thompson. Analgesic effects of different pulse patterns of transcutaneous electrical nerve stimulation on cold-induced pain in normal subjects. Journal of Psychosomatic Research 35 (2/3, 1991):313-321; U.S. Pat. No. 7,734,340, entitled Stimulation design for neuromodulation, to De Ridder]. However, bursts of sinusoidal pulses are a preferred stimulation waveform, as shown in FIGS. 2D and 2E. As seen there, individual sinusoidal pulses have a period of, and a burst consists of N such pulses. This is followed by a period with no signal (the inter-burst period). The pattern of a burst followed by silent inter-burst period repeats itself with a period of T. For example, the sinusoidal period may be between about 50-1000 microseconds (equivalent to about 1-20 KHz), preferably between about 100-400 microseconds (equivalent to about 2.5-10 KHz), more preferably about 133-400 microseconds (equivalent to about 2.5-7.5 KHZ) and even more preferably about 200 microseconds (equivalent to about 5 KHz); the number of pulses per burst may be N=1-20, preferably about 2-10 and more preferably about 5; and the whole pattern of burst followed by silent inter-burst period may have a period T comparable to about 10-100 Hz, preferably about 15-50 Hz, more preferably about 25-35 Hz and even more preferably about 25 Hz (a much smaller value of T is shown in FIG. 2E to make the bursts discernable). When these exemplary values are used for T and, the waveform contains significant Fourier components at higher frequencies (½00 microseconds=5000/sec), as compared with those contained in transcutaneous nerve stimulation waveforms, as currently practiced.

Applicant is unaware of such a waveform having been used with vagus nerve stimulation, but a similar waveform has been used to stimulate muscle as a means of increasing muscle strength in elite athletes. However, for the muscle strengthening application, the currents used (200 mA) may be very painful and two orders of magnitude larger than what are disclosed herein. Furthermore, the signal used for muscle strengthening may be other than sinusoidal (e.g., triangular), and the parameters, N, and T may also be dissimilar from the values exemplified above [A. DELITTO, M. Brown, M. J. Strube, S. J. Rose, and R. C. Lehman. Electrical stimulation of the quadriceps femoris in an elite weight lifter: a single subject experiment. Int J Sports Med 10(1989):187-191; Alex R WARD, Nataliya Shkuratova. Russian Electrical Stimulation: The Early Experiments. Physical Therapy 82 (10,2002): 1019-1030; Yocheved LAUFER and Michal Elboim. Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88 (10,2008):1167-1176; Alex R WARD. Electrical Stimulation Using Kilohertz-Frequency Alternating Current. Physical Therapy 89 (2,2009):181-190; J. PETROFSKY, M. Laymon, M. Prowse, S. Gunda, and J. Batt. The transfer of current through skin and muscle during electrical stimulation with sine, square, Russian and interferential waveforms. Journal of Medical Engineering and Technology 33 (2,2009): 170-181; U.S. Pat. No. 4,177,819, entitled Muscle stimulating apparatus, to KOFSKY et al]. Burst stimulation has also been disclosed in connection with implantable pulse generators, but wherein the bursting is characteristic of the neuronal firing pattern itself [U.S. Pat. No. 7,734,340 to DE RIDDER, entitled Stimulation design for neuromodulation; application US20110184486 to DE RIDDER, entitled Combination of tonic and burst stimulations to treat neurological disorders]. By way of example, the electric field shown in FIGS. 2D and 2E may have an $E_{max}$ value of 17 V/m, which is sufficient to stimulate the nerve but is significantly lower than the threshold needed to stimulate surrounding muscle.

High frequency electrical stimulation is also known in the treatment of back pain at the spine [Patent application US20120197369, entitled Selective high frequency spinal cord modulation for inhibiting pain with reduced side effects and associated systems and methods, to ALATARIS et al.; Adrian A L KAISY, Iris Smet, and Jean-Pierre Van Buyten. Analgeia of axial low back pain with novel spinal neuromodulation. Poster presentation #202 at the 2011 meeting of The American Academy of Pain Medicine, held in National Harbor, MD, Mar. 24-27, 2011].

Those methods involve high-frequency modulation in the range of from about 1.5 KHz to about 50 KHz, which is applied to the patient's spinal cord region. However, such methods are different from the present description because, for example, they is invasive; they do not involve a bursting waveform, as in the present description; they necessarily involve A-delta and C nerve fibers and the pain that those fibers produce, whereas the present description does not; they may involve a conduction block applied at the dorsal root level, whereas the present description may stimulate action potentials without blocking of such action potentials; and/or they involve an increased ability of high frequency modulation to penetrate through the cerebral spinal fluid, which is not relevant to the present description. In fact, a likely explanation for the reduced back pain that is produced by their use of frequencies from 10 to 50 KHz is that the applied electrical stimulus at those frequencies causes permanent damage to the pain-causing nerves, whereas the present description involves only reversible effects [LEE RC, Zhang D, Hannig J. Biophysical injury mechanisms in electrical shock trauma. Annu Rev Biomed Eng 2(2000): 477-509].

Consider now which nerve fibers may be stimulated by the non-invasive vagus nerve stimulation. The waveform disclosed in FIG. 2 contains significant Fourier components at high frequencies (e.g., ½00 microseconds=5000/sec), even if the waveform also has components at lower frequencies (e.g., 25/sec). Transcutaneously, A-beta, A-delta, and C fibers are typically excited at 2000 Hz, 250 Hz, and 5 Hz, respectively, i.e., the 2000 Hz stimulus is described as being specific for measuring the response of A-beta fibers, the 250 Hz for A-delta fibers, and the 5 Hz for type C fibers [George D. BAQUIS et al. TECHNOLOGY REVIEW: THE NEUROMETER CURRENT PERCEPTION THRESHOLD (CPT). Muscle Nerve 22 (Supplement 8, 1999): S247-S259]. Therefore, the high frequency component of the noninvasive stimulation waveform will preferentially stimulate the A-alpha and A-beta fibers, and the C fibers will be largely unstimulated.

However, the threshold for activation of fiber types also depends on the amplitude of the stimulation, and for a given stimulation frequency, the threshold increases as the fiber size decreases. The threshold for generating an action potential in nerve fibers that are impaled with electrodes is traditionally described by Lapicque or Weiss equations, which describe how together the width and amplitude of stimulus pulses determine the threshold, along with parameters that characterize the fiber (the chronaxy and rheobase). For nerve fibers that are stimulated by electric fields that are applied externally to the fiber, as is the case here, characterizing the threshold as a function of pulse amplitude and frequency is more complicated, which ordinarily involves the numerical solution of model differential equations or a case-by-case experimental evaluation [David BOINAGROV, Jim Loudin and Daniel Palanker. Strength-Duration Relationship for Extracellular Neural Stimulation: Numerical and Analytical Models. J Neurophysiol 104(2010):2236-2248].

For example, REILLY describes a model (the spatially extended nonlinear nodal model or SENN model) that may be used to calculate minimum stimulus thresholds for nerve fibers having different diameters [J. Patrick REILLY. Electrical models for neural excitation studies. Johns Hopkins APL Technical Digest 9(1, 1988): 44-59]. According to REILLY's analysis, the minimum threshold for excitation of myelinated A fibers is 6.2 V/m for a 20 µm diameter fiber, 12.3 V/m for a 10 µm fiber, and 24.6 V/m for a 5 µm diameter fiber, assuming a pulse width that is within the contemplated range of the present description (1 ms). It is understood that these thresholds may differ slightly from those produced by the waveform of the present description as illustrated by REILLY's figures, for example, because the present description prefers to use sinusoidal rather than square pulses. Thresholds for B and C fibers are respectively 2 to 3 and 10 to 100 times greater than those for A fibers [Mark A. CASTORO, Paul B. Yoo, Juan G. Hincapie, Jason J. Hamann, Stephen B. Ruble, Patrick D. Wolf, Warren M. Grill. Excitation properties of the right cervical vagus nerve in adult dogs. Experimental Neurology 227 (2011): 62-68]. If we assume an average A fiber threshold of 15 V/m, then B fibers would have thresholds of 30 to 45 V/m and C fibers would have thresholds of 150 to 1500 V/m. The present description produces electric fields at the vagus nerve in the range of about 6 to about 100 V/m, which is therefore generally sufficient to excite all myelinated A and B fibers, but not the unmyelinated C fibers. In contrast, invasive vagus nerve stimulators that have been used for the treatment of epilepsy have been reported to excite C fibers in some patients [EVANS MS, Verma-Ahuja S, Naritoku D K, Espinosa J A. Intraoperative human vagus nerve compound action potentials. Acta Neurol Scand 110(2004): 232-238].

It is understood that although devices of the present description may stimulate A and B nerve fibers, in practice they may also be used so as not to stimulate the largest A fibers (A-delta) and B fibers. In particular, if the stimulator amplitude has been increased to the point at which unwanted side effects begin to occur, the operator of the device may simply reduce the amplitude to avoid those effects. For example, vagal efferent fibers responsible for bronchoconstriction have been observed to have conduction velocities in the range of those of B fibers. In those experiments, bronchoconstriction was only produced when B fibers were activated, and became maximal before C fibers had been recruited [R. M. McALLEN and K. M. Spyer. Two types of vagal preganglionic motoneurones projecting to the heart and lungs. J. Physiol. 282(1978): 353-364]. Because proper stimulation with the disclosed devices does not result in the side-effect of bronchoconstriction, evidently the bronchoconstrictive B-fibers are possibly not being activated when the amplitude is properly set. Also, the absence of bradycardia or prolongation of PR interval suggests that cardiac efferent B-fibers are not stimulated. Similarly, A-delta afferents may behave physiologically like C fibers. Because stimulation with the disclosed devices does not produce nociceptive effects that would be produced by jugular A-delta fibers or C fibers, evidently the A-delta fibers may not be stimulated when the amplitude is properly set.

To summarize the foregoing discussion, the delivery of an impulse of energy sufficient to stimulate and/or modulate transmission of signals of vagus nerve fibers will result in the inhibition of excitatory neurotramsmitters and to a more normal activity within higher centers of the brain, many of which are components of resting state networks. The most likely mechanisms do not involve the stimulation of C fibers; and the stimulation of afferent nerve fibers activates neural pathways causes the release of norepinephrine, and/or serotonin and/or GABA.

Figure 8:
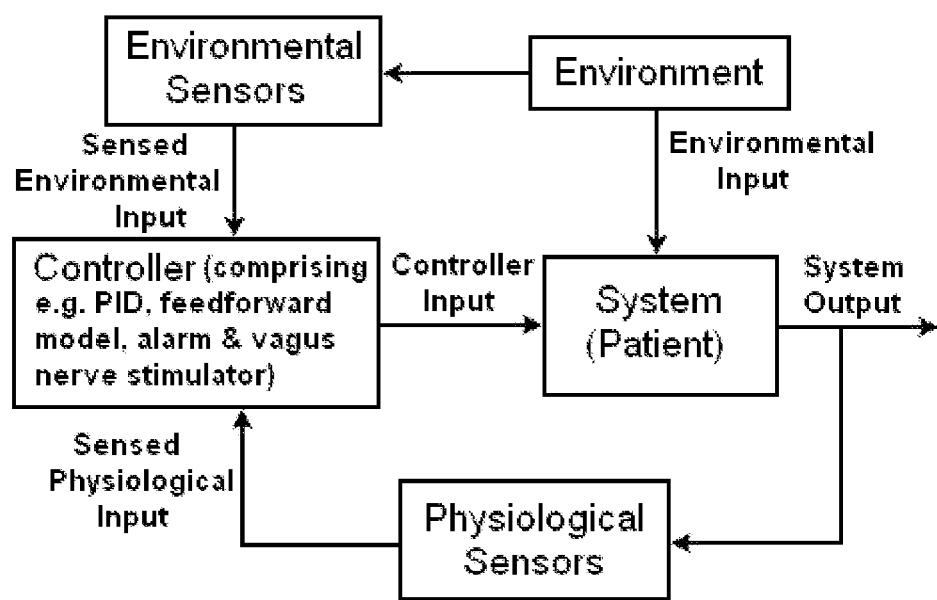
FIG. 8 illustrates connections between the controller and controlled system according to the present description, their input and output signals, and external signals from the environment.

The use of feedback to generate the modulation signal 400 may result in a signal that is not periodic, particularly if the feedback is produced from sensors that measure naturally occurring, time-varying aperiodic physiological signals from the patient (see FIG. 8). In fact, the absence of significant fluctuation in naturally occurring physiological signals from a patient is ordinarily considered to be an indication that the patient is in ill health. This is because a pathological control system that regulates the patient's physiological variables may have become trapped around only one of two or more possible steady states and is therefore unable to respond normally to external and internal stresses. Accordingly, even if feedback is not used to generate the modulation signal 400, it may be useful to artificially modulate the signal in an aperiodic fashion, in such a way as to simulate fluctuations that would occur naturally in a healthy individual. Thus, the noisy modulation of the stimulation signal may cause a pathological physiological control system to be reset or undergo a non-linear phase transition, through a mechanism known as stochastic resonance [B. SUKI, A. Alencar, M. K. Sujeer, K. R. Lutchen, J. J. Collins, J. S. Andrade, E. P. Ingenito, S. Zapperi, H. E. Stanley, Life-support system benefits from noise, Nature 393 (1998) 127-128; W Alan C MUTCH, M Ruth Graham, Linda G Girling and John F Brewster. Fractal ventilation enhances respiratory sinus arrhythmia. Respiratory Research 2005, 6:41, pp. 1-9].

So, in one embodiment of the present description, the modulation signal 400, with or without feedback, will stimulate the selected nerve fibers in such a way that one or more of the stimulation parameters (power, frequency, and others mentioned herein) are varied by sampling a statistical distribution having a mean corresponding to a selected, or to a most recent running-averaged value of the parameter, and then setting the value of the parameter to the randomly sampled value. The sampled statistical distributions will comprise Gaussian and 1/f, obtained from recorded naturally occurring random time series or by calculated formula. Parameter values will be so changed periodically, or at time intervals that are themselves selected randomly by sampling another statistical distribution, having a selected mean and coefficient of variation, where the sampled distributions comprise Gaussian and exponential, obtained from recorded naturally occurring random time series or by calculated formula.

In another embodiment, devices in accordance with the present description are provided in a "pacemaker" type form, in which electrical impulses 410 are generated to a selected region of the nerve by a stimulator device on an intermittent basis, to create in the patient a lower reactivity of the nerve.

Preferred Embodiments of the Magnetic Stimulator

A preferred embodiment of magnetic stimulator coil 341 comprises a toroidal winding around a core consisting of high-permeability material (e.g., Supermendur), embedded in an electrically conducting medium. Toroidal coils with high permeability cores have been theoretically shown to greatly reduce the currents required for transcranial (TMS) and other forms of magnetic stimulation, but only if the toroids are embedded in a conducting medium and placed against tissue with no air interface [Rafael CARBUNARU and Dominique M. Durand. Toroidal coil models for transcutaneous magnetic stimulation of nerves. IEEE Transactions on Biomedical Engineering 48 (4, 2001): 434-441; Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999, (UMI Microform Number: 9940153, UMI Company, Ann Arbor MI)].

Although Carbunaru and Durand demonstrated that it is possible to electrically stimulate a patient transcutaneously with such a device, they made no attempt to develop the device in such a way as to generally shape the electric field that is to stimulate the nerve. In particular, the electric fields that may be produced by their device are limited to those that are radially symmetric at any given depth of stimulation into the patient (i.e, two variables, z and rho, are used to specify location of the field, not x, y, and z). This is a significant limitation, and it results in a deficiency that was noted in FIG. 6 of their publication: "at large depths of stimulation, the threshold current [in the device's coil] for long axons is larger than the saturation current of the coil. Stimulation of those axons is only possible at low threshold points such as bending sites or tissue conductivity inhomogeneities". Thus, for their device, varying the parameters that they considered, in order to increase the electric field or its gradient in the vicinity of a nerve, may come at the expense of limiting the field's physiological effectiveness, such that the spatial extent of the field of stimulation may be insufficient to modulate the target nerve's function. Yet, such long axons are precisely what we may wish to stimulate in therapeutic interventions, such as the ones disclosed herein.

Accordingly, it is an objective of the present description to shape an elongated electric field of effect that can be oriented parallel to such a long nerve. The term "shape an electric field" as used herein means to create an electric field or its gradient that is generally not radially symmetric at a given depth of stimulation in the patient, especially a field that is characterized as being elongated or finger-like, and especially also a field in which the magnitude of the field in some direction may exhibit more than one spatial maximum (i.e. may be bimodal or multimodal) such that the tissue between the maxima may contain an area across which induced current flow is restricted. Shaping of the electric field refers both to the circumscribing of regions within which there is a significant electric field and to configuring the directions of the electric field within those regions. The shaping of the electric field is described in terms of the corresponding field equations in commonly assigned application US20110125203 (application Ser. No. 12/964,050), entitled Magnetic stimulation devices and methods of therapy, to SIMON et al., which is hereby incorporated by reference.

Thus, the present description differs from the device disclosed by CARBUNARU and Durand by deliberately shaping an electric field that is used to transcutaneously stimulate the patient. Whereas the toroid in the CARBUNARU and Durand publication was immersed in a homogeneous conducting half-space, this is not necessarily the case for our description. Although our description will generally have some continuously conducting path between the device's coil and the patient's skin, the conducting medium need not totally immerse the coil, and there may be insulating voids within the conducting medium. For example, if the device contains two toroids, conducting material may connect each of the toroids individually to the patient's skin, but there may be an insulating gap (from air or some other insulator) between the surfaces at which conducting material connected to the individual toroids contact the patient. Furthermore, the area of the conducting material that contacts the skin may be made variable, by using an aperture adjusting mechanism such as an iris diaphragm. As another example, if the coil is wound around core material that is laminated, with the core in contact with the device's electrically conducting material, then the lamination may be extended into the conducting material in such a way as to direct the induced electrical current between the laminations and towards the surface of the patient's skin. As another example, the conducting material may pass through apertures in an insulated mesh before contacting the patient's skin, creating thereby an array of electric field maxima.

In the dissertation cited above, Carbunaru—FAIERSTEIN made no attempt to use conducting material other than agar in a KCl solution, and he made no attempt to devise a device that could be conveniently and safely applied to a patient's skin, at an arbitrary angle without the conducting material spilling out of its container. It is therefore an objective of the present description to disclose conducting material that can be used not only to adapt the conductivity of the conducting material and select boundary conditions, thereby shaping the electric fields and currents as described above, but also to create devices that can be applied practically to any surface of the body. The volume of the container containing electrically conducting medium is labeled in FIG. 2A as 351. Use of the container of conducting medium 351 allows one to generate (induce) electric fields in tissue (and electric field gradients and electric currents) that are equivalent to those generated using current magnetic stimulation devices, but with about 0.001 percent to about 0.1 percent of the current conventionally applied to a magnetic stimulation coil. This allows for minimal heating of the coil(s) and deeper tissue stimulation. However, application of the conducting medium to the surface of the patient is difficult to perform in practice because the tissue contours (head, arms, legs, neck, etc.) are not planar. To solve this problem, in the preferred embodiment of the present description, the toroidal coil is embedded in a structure which is filled with a conducting medium having approximately the same conductivity as muscle tissue, as now described.

In one embodiment of the description, the container contains holes so that the conducting material (e.g., a conducting gel) can make physical contact with the patient's skin through the holes. For example, the conducting medium 351 may comprise a chamber surrounding the coil, filled with a conductive gel that has the approximate viscosity and mechanical consistency of gel deodorant (e.g., Right Guard Clear Gel from Dial Corporation, 15501 N. Dial Boulevard, Scottsdale AZ 85260, one composition of which comprises aluminum chlorohydrate, sorbitol, propylene glycol, polydimethylsiloxanes Silicon oil, cyclomethicone, ethanol/SD Alcohol 40, dimethicone copolyol, aluminum zirconium tetrachlorohydrex gly, and water). The gel, which is less viscous than conventional electrode gel, is maintained in the chamber with a mesh of openings at the end where the device is to contact the patient's skin. The gel does not leak out, and it can be dispensed with a simple screw driven piston.

In another embodiment, the container itself is made of a conducting elastomer (e.g., dry carbon-filled silicone elastomer), and electrical contact with the patient is through the elastomer itself, possibly through an additional outside coating of conducting material. In some embodiments of the description, the conducting medium may be a balloon filled with a conducting gel or conducting powders, or the balloon may be constructed extensively from deformable conducting elastomers. The balloon conforms to the skin surface, removing any air, thus allowing for high impedance matching and conduction of large electric fields in to the tissue. A device such as that disclosed in U.S. Pat. No. 7,591,776, entitled Magnetic stimulators and stimulating coils, to PHILLIPS et al. may conform the coil itself to the contours of the body, but in the preferred embodiment, such a curved coil is also enclosed by a container that is filled with a conducting medium that deforms to be contiguous with the skin.

Agar can also be used as part of the conducting medium, but it is not preferred, because agar degrades in time, is not ideal to use against skin, and presents difficulties with cleaning the patient and stimulator coil. Use of agar in a 4M KCl solution as a conducting medium was mentioned in the above-cited dissertation: Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999, page 117 (UMI Microform Number: 9940153, UMI Company, Ann Arbor MI). However, that publication makes no mention or suggestion of placing the agar in a conducting elastomeric balloon, or other deformable container so as to allow the conducting medium to conform to the generally non-planar contours of a patient's skin having an arbitrary orientation. In fact, that publication describes the coil as being submerged in a container filled with an electrically conducting solution. If the coil and container were placed on a body surface that was oriented in the vertical direction, then the conducting solution would spill out, making it impossible to stimulate the body surface in that orientation. In contrast, the present description is able to stimulate body surfaces having arbitrary orientation.

That dissertation also makes no mention of a dispensing method whereby the agar would be made contiguous with the patient's skin. A layer of electrolytic gel is said to have been applied between the skin and coil, but the configuration was not described clearly in the publication. In particular, no mention is made of the electrolytic gel being in contact with the agar.

Rather than using agar as the conducting medium, the coil can instead be embedded in a conducting solution such as 1-10% NaCl, contacting an electrically conducting interface to the human tissue. Such an interface is used as it allows current to flow from the coil into the tissue and supports the medium-surrounded toroid so that it can be completely sealed. Thus, the interface is material, interposed between the conducting medium and patient's skin, that allows the conducting medium (e.g., saline solution) to slowly leak through it, allowing current to flow to the skin. Several interfaces are disclosed as follows.

One interface comprises conducting material that is hydrophilic, such as Tecophlic from The Lubrizol Corporation, 29400 Lakeland Boulevard, Wickliffe, Ohio 44092. It absorbs from 10-100% of its weight in water, making it highly electrically conductive, while allowing only minimal bulk fluid flow.

Another material that may be used as an interface is a hydrogel, such as that used on standard EEG, EKG and TENS electrodes [Rylie A GREEN, Sungchul Baek, Laura A Poole-Warren and Penny J Martens. Conducting polymer-hydrogels for medical electrode applications. Sci. Technol. Adv. Mater. 11 (2010) 014107 (13 pp)]. For example it may be the following hypoallergenic, bacteriostatic electrode gel: SIGNAGEL Electrode Gel from Parker Laboratories, Inc., 286 Eldridge Rd., Fairfield NJ 07004.

A third type of interface may be made from a very thin material with a high dielectric constant, such as those used to make capacitors. For example, Mylar can be made in submicron thicknesses and has a dielectric constant of about 3. Thus, at stimulation frequencies of several kilohertz or greater, the Mylar will capacitively couple the signal through it because it will have an impedance comparable to that of the skin itself. Thus, it will isolate the toroid and the solution it is embedded in from the tissue, yet allow current to pass.

The preferred embodiment of the magnetic stimulator coil 341 in FIG. 2A reduces the volume of conducting material that must surround a toroidal coil, by using two toroids, side-by-side, and passing electrical current through the two toroidal coils in opposite directions. In this configuration, the induced current will flow from the lumen of one toroid, through the tissue and back through the lumen of the other, completing the circuit within the toroids' conducting medium. Thus, minimal space for the conducting medium is required around the outside of the toroids at positions near from the gap between the pair of coils. An additional advantage of using two toroids in this configuration is that this design will greatly increase the magnitude of the electric field gradient between them, which is crucial for exciting long, straight axons such as the vagus nerve and certain other peripheral nerves.

This preferred embodiment of the magnetic stimulation device is shown in FIG. 3. FIGS. 3A and 3B respectively provide top and bottom views of the outer surface of the toroidal magnetic stimulator 30. FIGS. 3C and 3D respectively provide top and bottom views of the toroidal magnetic stimulator 30, after sectioning along its long axis to reveal the inside of the stimulator.

FIGS. 3A-3D all show a mesh 31 with openings that permit a conducting gel to pass from the inside of the stimulator to the surface of the patient's skin at the location of nerve or tissue stimulation. Thus, the mesh with openings 31 is the part of the stimulator that is applied to the skin of the patient.

Figure 3A:
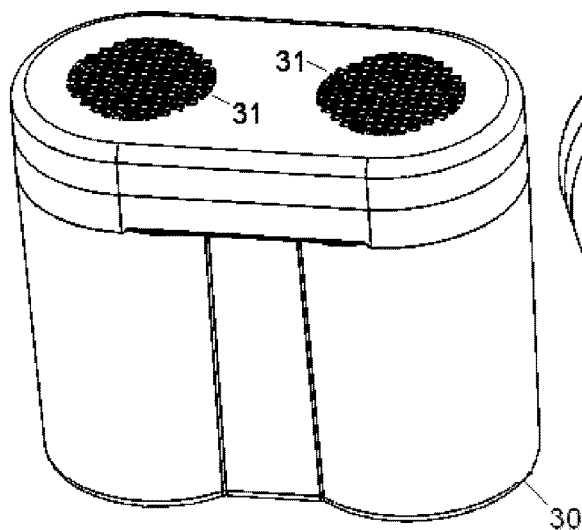
FIG. 3A is a perspective view of the top of a dual-toroid magnetic stimulator coil according to an embodiment of the present description.
Figure 3B:
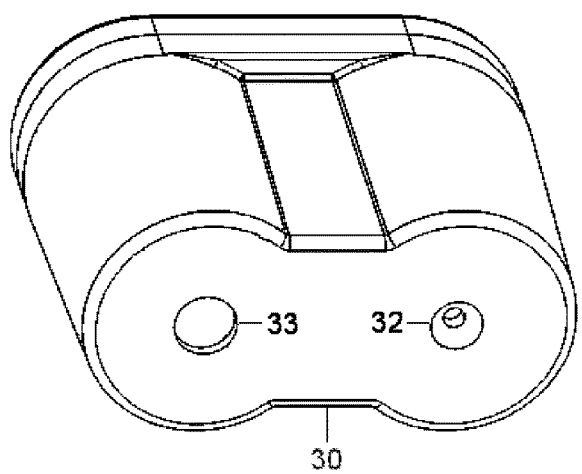
FIG. 3B is a perspective view of the bottom of the magnetic stimulator coil of FIG. 3A.
Figure 3C:
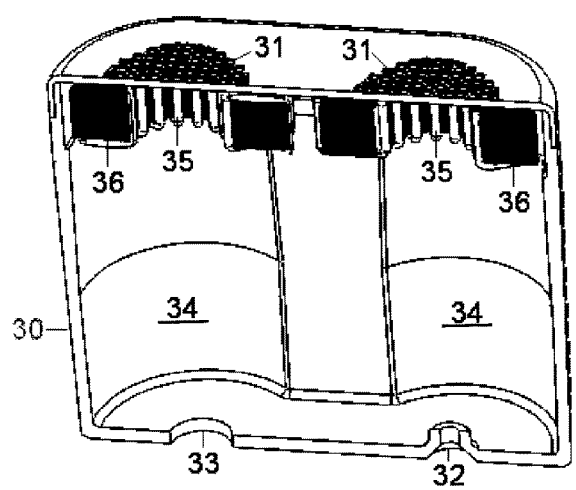
FIG. 3C is a cut-a-way view of the magnetic stimulator coil of FIG. 3A.
Figure 3D:
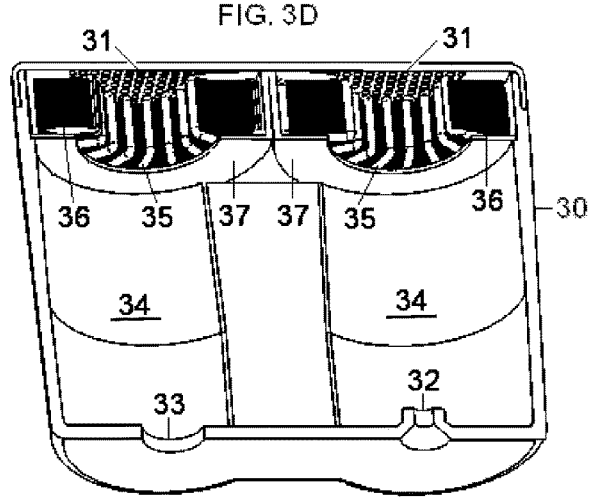
FIG. 3D is another cut-a-way view of the magnetic stimulator coil of FIG. 3A.

FIGS. 3B-3D show openings at the opposite end of the stimulator 30. One of the openings is an electronics port 32 through which wires pass from the stimulator coil(s) to the impulse generator (310 in FIG. 2A). The second opening is a conducting gel port 33 through which conducting gel may be introduced into the stimulator 30 and through which a screw-driven piston arm may be introduced to dispense conducting gel through the mesh 31. The gel itself will be contained within cylindrical-shaped but interconnected conducting medium chambers 34 that are shown in FIGS. 3C and 3D. The depth of the conducting medium chambers 34, which is approximately the height of the long axis of the stimulator, affects the magnitude of the electric fields and currents that are induced by the device [Rafael CARBUNARU and Dominique M. Durand. Toroidal coil models for transcutaneous magnetic stimulation of nerves. IEEE Transactions on Biomedical Engineering. 48 (4, 2001): 434-441].

FIGS. 3C and 3D also show the coils of wire 35 that are wound around toroidal cores 36, consisting of high-permeability material (e.g., Supermendur). Lead wires (not shown) for the coils 35 pass from the stimulator coil(s) to the impulse generator (310 in FIG. 1) via the electronics port 32. Different circuit configurations are contemplated. If separate lead wires for each of the coils 35 connect to the impulse generator (i.e., parallel connection), and if the pair of coils are wound with the same handedness around the cores, then the design is for current to pass in opposite directions through the two coils. On the other hand, if the coils are wound with opposite handedness around the cores, then the lead wires for the coils may be connected in series to the impulse generator, or if they are connected to the impulse generator in parallel, then the design is for current to pass in the same direction through both coils.

As seen in FIGS. 3C and 3D, the coils 35 and cores 36 around which they are wound are mounted as close as practical to the corresponding mesh 31 with openings through which conducting gel passes to the surface of the patient's skin. As seen in FIG. 3D, each coil and the core around which it is wound is mounted in its own housing 37, the function of which is to provide mechanical support to the coil and core, as well as to electrically insulate a coil from its neighboring coil. With this design, induced current will flow from the lumen of one toroid, through the tissue and back through the lumen of the other, completing the circuit within the toroids' conducting medium.

Different diameter toroidal coils and windings may be preferred for different applications. For a generic application, the outer diameter of the core may be typically 1 to 5 cm, with an inner diameter typically 0.5 to 0.75 of the outer diameter. The coil's winding around the core may be typically 3 to 250 in number, depending on the core diameter and depending on the desired coil inductance.

Signal generators for magnetic stimulators have been described for commercial systems [Chris HOVEY and Reza Jalinous, THE GUIDE TO MAGNETIC STIMULATION, The Magstim Company Ltd, Spring Gardens, Whitland, Carmarthenshire, SA34 0HR, United Kingdom, 2006], as well as for custom designs for a control unit 330, impulse generator 310 and power source 320 [Eric BASHAM, Zhi Yang, Natalia Tchemodanov, and Wentai Liu. Magnetic Stimulation of Neural Tissue: Techniques and System Design. pp 293-352, In: Implantable Neural Prostheses 1, Devices and Applications, D. Zhou and E. Greenbaum, eds., New York: Springer (2009); U.S. Pat. No. 7,744,523, entitled Drive circuit for magnetic stimulation, to Charles M. Epstein; U.S. Pat. No. 5,718,662, entitled Apparatus for the magnetic stimulation of cells or tissue, to Reza Jalinous; U.S. Pat. No. 5,766,124, entitled Magnetic stimulator for neuro-muscular tissue, to Poison]. Conventional magnetic nerve stimulators use a high current impulse generator that may produce discharge currents of 5,000 amps or more, which is passed through the stimulator coil, and which thereby produces a magnetic pulse. Typically, a transformer charges a capacitor in the impulse generator 310, which also contains circuit elements that limit the effect of undesirable electrical transients. Charging of the capacitor is under the control of a control unit 330, which accepts information such as the capacitor voltage, power and other parameters set by the user, as well as from various safety interlocks within the equipment that ensure proper operation, and the capacitor is then discharged through the coil via an electronic switch (e.g., a controlled rectifier) when the user wishes to apply the stimulus.

Greater flexibility is obtained by adding to the impulse generator a bank of capacitors that can be discharged at different times. Thus, higher impulse rates may be achieved by discharging capacitors in the bank sequentially, such that recharging of capacitors is performed while other capacitors in the bank are being discharged. Furthermore, by discharging some capacitors while the discharge of other capacitors is in progress, by discharging the capacitors through resistors having variable resistance, and by controlling the polarity of the discharge, the control unit may synthesize pulse shapes that approximate an arbitrary function.

The design and methods of use of impulse generators, control units, and stimulator coils for magnetic stimulators are informed by the designs and methods of use of impulse generators, control units, and electrodes (with leads) for comparable completely electrical nerve stimulators, but design and methods of use of the magnetic stimulators must take into account many special considerations, making it generally not straightforward to transfer knowledge of completely electrical stimulation methods to magnetic stimulation methods. Such considerations include determining the anatomical location of the stimulation and determining the appropriate pulse configuration [OLNEY RK, So Y T, Goodin D S, Aminoff M J. A comparison of magnetic and electric stimulation of peripheral nerves. Muscle Nerve 1990:13:957-963; J. NILSSON, M. Panizza, B. J. Roth et al. Determining the site of stimulation during magnetic stimulation of the peripheral nerve, Electroencephalographs and clinical neurophysiology 85(1992): 253-264; Nafia AL-MUTAWALY, Hubert de Bruin, and Gary Hasey. The effects of pulse configuration on magnetic stimulation. Journal of Clinical Neurophysiology 20(5):361-370, 2003].

Furthermore, a potential practical disadvantage of using magnetic stimulator coils is that they may overheat when used over an extended period of time. Use of the above-mentioned toroidal coil and container of electrically conducting medium addresses this potential disadvantage. However, because of the poor coupling between the stimulating coils and the nerve tissue, large currents are nevertheless required to reach threshold electric fields. At high repetition rates, these currents can heat the coils to unacceptable levels in seconds to minutes depending on the power levels and pulse durations and rates. Two approaches to overcome heating are to cool the coils with flowing water or air or to increase the magnetic fields using ferrite cores (thus allowing smaller currents). For some applications where relatively long treatment times at high stimulation frequencies may be required, neither of these two approaches are adequate. Water-cooled coils overheat in a few minutes. Ferrite core coils heat more slowly due to the lower currents and heat capacity of the ferrite core, but also cool off more slowly and do not allow for water-cooling since the ferrite core takes up the volume where the cooling water would flow.

A solution to this problem is to use a fluid which contains ferromagnetic particles in suspension like a ferrofluid, or magnetorheological fluid as the cooling material. Ferrofluids are colloidal mixtures composed of nanoscale ferromagnetic, or ferrimagnetic, particles suspended in a carrier fluid, usually an organic solvent or water. The ferromagnetic nanoparticles are coated with a surfactant to prevent their agglomeration (due to van der Waals forces and magnetic forces). Ferrofluids have a higher heat capacity than water and will thus act as better coolants. In addition, the fluid will act as a ferrite core to increase the magnetic field strength. Also, since ferrofluids are paramagnetic, they obey Curie's law, and thus become less magnetic at higher temperatures. The strong magnetic field created by the magnetic stimulator coil will attract cold ferrofluid more than hot ferrofluid thus forcing the heated ferrofluid away from the coil. Thus, cooling may not require pumping of the ferrofluid through the coil, but only a simple convective system for cooling. This is an efficient cooling method which may require no additional energy input [U.S. Pat. No. 7,396,326 and published applications US2008/0114199, US2008/0177128, and US2008/0224808, all entitled Ferrofluid cooling and acoustical noise reduction in magnetic stimulators, respectively to Ghiron et al., Riehl et al., Riehl et al. and Ghiron et al.].

Magnetorheological fluids are similar to ferrofluids but contain larger magnetic particles which have multiple magnetic domains rather than the single domains of ferrofluids. [U.S. Pat. No. 6,743,371, Magneto sensitive fluid composition and a process for preparation thereof, to John et al.]. They can have a significantly higher magnetic permeability than ferrofluids and a higher volume fraction of iron to carrier. Combinations of magnetorheological and ferrofluids may also be used [M T LOPEZ-LOPEZ, P Kuzhir, S Lacis, G Bossis, F Gonzalez-Caballero and J D G Duran. Magnetorheology for suspensions of solid particles dispersed in ferrofluids. J. Phys.: Condens. Matter 18 (2006) S2803-S2813; Ladislau VEKAS. Ferrofluids and Magnetorheological Fluids. Advances in Science and Technology Vol. 54 (2008) pp 127-136.].

Commercially available magnetic stimulators include circular, parabolic, figure-of-eight (butterfly), and custom designs that are available commercially [Chris HOVEY and Reza Jalinous, THE GUIDE TO MAGNETIC STIMULATION, The Magstim Company Ltd, Spring Gardens, Whitland, Carmarthenshire, SA34 0HR, United Kingdom, 2006]. Additional embodiments of the magnetic stimulator coil 341 have been described [U.S. Pat. No. 6,179,770, entitled Coil assemblies for magnetic stimulators, to Stephen Mould; Kent DAVEY. Magnetic Stimulation Coil and Circuit Design. IEEE Transactions on Biomedical Engineering, Vol. 47 (No. 11, November 2000): 1493-1499]. Many of the problems that are associated with such conventional magnetic stimulators, e.g., the complexity of the impulse-generator circuitry and the problem with overheating, are largely avoided by the toroidal design shown in FIG. 3.

Thus, use of the container of conducting medium 351 allows one to generate (induce) electric fields in tissue (and electric field gradients and electric currents) that are equivalent to those generated using current magnetic stimulation devices, but with about 0.001 percent to about 0.1 percent of the current conventionally applied to a magnetic stimulation coil. Therefore, with the present description, it is possible to generate waveforms shown in FIG. 2 with relatively simple, low-power circuits that are powered by batteries. The circuits may be enclosed within a box 38 as shown in FIG. 3E, or the circuits may be attached to the stimulator itself (FIG. 3A-3D) to be used as a hand-held device. In either case, control over the unit may be made using only an on/off switch and power knob. The only other component that may be needed might be a cover 39 to keep the conducting fluid from leaking or drying out between uses. The currents passing through the coils of the magnetic stimulator will saturate its core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses, as described in connection with FIGS. 2D and 2E, shaping an elongated electrical field of effect.

Preferred Embodiments of the Electrode-Based Stimulator

In another embodiment of the description, electrodes applied to the surface of the neck, or to some other surface of the body, are used to non-invasively deliver electrical energy to a nerve, instead of delivering the energy to the nerve via a magnetic coil. The vagus nerve has been stimulated previously non-invasively using electrodes applied via leads to the surface of the skin. It has also been stimulated non-electrically through the use of mechanical vibration [HUSTON J M, Gallowitsch-Puerta M, Ochani M, Ochani K, Yuan R, Rosas-Ballina M et al (2007). Transcutaneous vagus nerve stimulation reduces serum high mobility group box 1 levels and improves survival in murine sepsis. Crit Care Med35: 2762-2768; GEORGE MS, Aston-Jones G. Noninvasive techniques for probing neurocircuitry and treating illness: vagus nerve stimulation (VNS), transcranial magnetic stimulation (TMS) and transcranial direct current stimulation (tDCS). Neuropsychopharmacology 35(1, 2010):301-316]. However, no such reported uses of noninvasive vagus nerve stimulation were directed to the treatment of stroke or transient ischemic attack patients. U.S. Pat. No. 7,340,299, entitled Methods of indirectly stimulating the vagus nerve to achieve controlled asystole, to John D. PUSKAS, discloses the stimulation of the vagus nerve using electrodes placed on the neck of the patient, but that patent is unrelated to the treatment of stroke or transient ischemic attacks. Non-invasive electrical stimulation of the vagus nerve has also been described in Japanese patent application JP2009233024A with a filing date of Mar. 26, 2008, entitled Vagus Nerve Stimulation System, to Fukui YOSHIHOTO, in which a body surface electrode is applied to the neck to stimulate the vagus nerve electrically. However, that application pertains to the control of heart rate and is unrelated to the treatment of stroke or transient ischemic attacks. In patent publication US20080208266, entitled System and method for treating nausea and vomiting by vagus nerve stimulation, to LESSER et al., electrodes are used to stimulate the vagus nerve in the neck to reduce nausea and vomiting, but this too is unrelated to the treatment of stroke or transient ischemic attacks.

Patent application US2010/0057154, entitled Device and method for the transdermal stimulation of a nerve of the human body, to DIETRICH et al., discloses a non-invasive transcutaneous/transdermal method for stimulating the vagus nerve, at an anatomical location where the vagus nerve has paths in the skin of the external auditory canal. Their non-invasive method involves performing electrical stimulation at that location, using surface stimulators that are similar to those used for peripheral nerve and muscle stimulation for treatment of pain (transdermal electrical nerve stimulation), muscle training (electrical muscle stimulation) and electroacupuncture of defined meridian points. The method used in that application is similar to the ones used in U.S. Pat. No. 4,319,584, entitled Electrical pulse acupressure system, to McCALL, for electroacupuncture; U.S. Pat. No. 5,514,175 entitled Auricular electrical stimulator, to KIM et al., for the treatment of pain; and U.S. Pat. No. 4,966,164, entitled Combined sound generating device and electrical acupuncture device and method for using the same, to COLSEN et al., for combined sound/electroacupuncture. A related application is US2006/0122675, entitled Stimulator for auricular branch of vagus nerve, to LIBBUS et al. Similarly, U.S. Pat. No. 7,386,347, entitled Electric stimulator for alpha-wave derivation, to CHUNG et al., described electrical stimulation of the vagus nerve at the ear. Patent application US2008/0288016, entitled Systems and Methods for Stimulating Neural Targets, to AMURTHUR et al., also discloses electrical stimulation of the vagus nerve at the ear. U.S. Pat. No. 4,865,048, entitled Method and apparatus for drug free neurostimulation, to ECKERSON, teaches electrical stimulation of a branch of the vagus nerve behind the ear on the mastoid processes, in order to treat symptoms of drug withdrawal. KRAUS et al described similar methods of stimulation at the ear [KRAUS T, HosI K, Kiess O, Schanze A, Kornhuber J, Forster C (2007). BOLD fMRI deactivation of limbic and temporal brain structures and mood enhancing effect by transcutaneous vagus nerve stimulation. J Neural Transm 114: 1485-1493]. However, none of the disclosures in these patents or patent applications for electrical stimulation of the vagus nerve at the ear are used to treat stroke or transient ischemic attacks.

Embodiments of the present description may differ with regard to the number of electrodes that are used, the distance between electrodes, and whether disk or ring electrodes are used. In preferred embodiments of the method, one selects the electrode configuration for individual patients, in such a way as to optimally focus electric fields and currents onto the selected nerve, without generating excessive currents on the surface of the skin. This tradeoff between focality and surface currents is described by DATTA et al. [Abhishek DATTA, Maged Elwassif, Fortunato Battaglia and Marom Bikson. Transcranial current stimulation focality using disc and ring electrode configurations: FEM analysis. J. Neural Eng. 5 (2008): 163-174]. Although DATTA et al. are addressing the selection of electrode configuration specifically for transcranial current stimulation, the principles that they describe are applicable to peripheral nerves as well [RATTAY F. Analysis of models for extracellular fiber stimulation. IEEE Trans. Biomed. Eng. 36 (1989): 676-682].

Considering that the nerve stimulating device 301 in FIG. 2A and the nerve stimulating device 302 in FIG. 2B both control the shape of electrical impulses, their functions are analogous, except that one stimulates nerves via a pulse of a magnetic field, and the other stimulates nerves via an electrical pulse applied through surface electrodes. Accordingly, general features recited for the nerve stimulating device 301 apply as well to the latter stimulating device 302 and will not be repeated here. The preferred parameters for each nerve stimulating device are those that produce the desired therapeutic effects.

A preferred embodiment of an electrode-based stimulator is shown in FIG. 4A. A cross-sectional view of the stimulator along its long axis is shown in FIG. 4B. As shown, the stimulator (730) comprises two heads (731) and a body (732) that joins them. Each head (731) contains a stimulating electrode. The body of the stimulator (732) contains the electronic components and battery (not shown) that are used to generate the signals that drive the electrodes, which are located behind the insulating board (733) that is shown in FIG. 4B. However, in other embodiments of the description, the electronic components that generate the signals that are applied to the electrodes may be separate, but connected to the electrode head (731) using wires. Furthermore, other embodiments of the description may contain a single such head or ore than two heads.

Heads of the stimulator (731) are applied to a surface of the patient's body, during which time the stimulator may be held in place by straps or frames or collars, or the stimulator may be held against the patient's body by hand. In either case, the level of stimulation power may be adjusted with a wheel (734) that also serves as an on/off switch. A light (735) is illuminated when power is being supplied to the stimulator. An optional cap may be provided to cover each of the stimulator heads (731), to protect the device when not in use, to avoid accidental stimulation, and to prevent material within the head from leaking or drying. Thus, in this embodiment of the description, mechanical and electronic components of the stimulator (impulse generator, control unit, and power source) are compact, portable, and simple to operate.

Figure 4C:
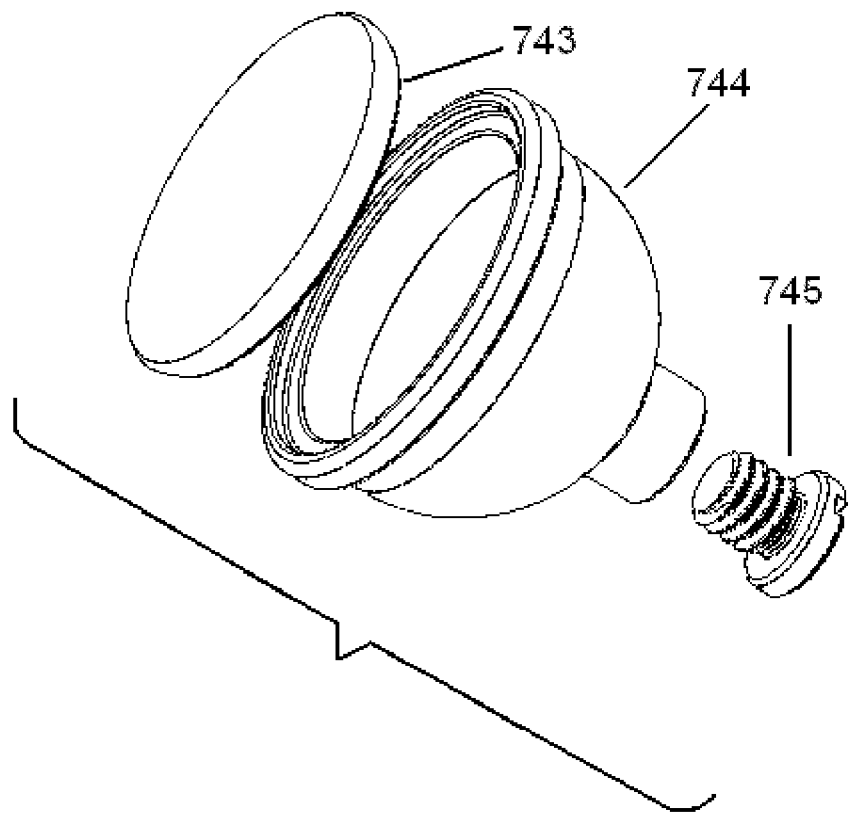
FIG. 4C is an exploded view of one of the electrode assemblies of the dual-electrode stimulator of FIG. 4A.
Figure 4D:
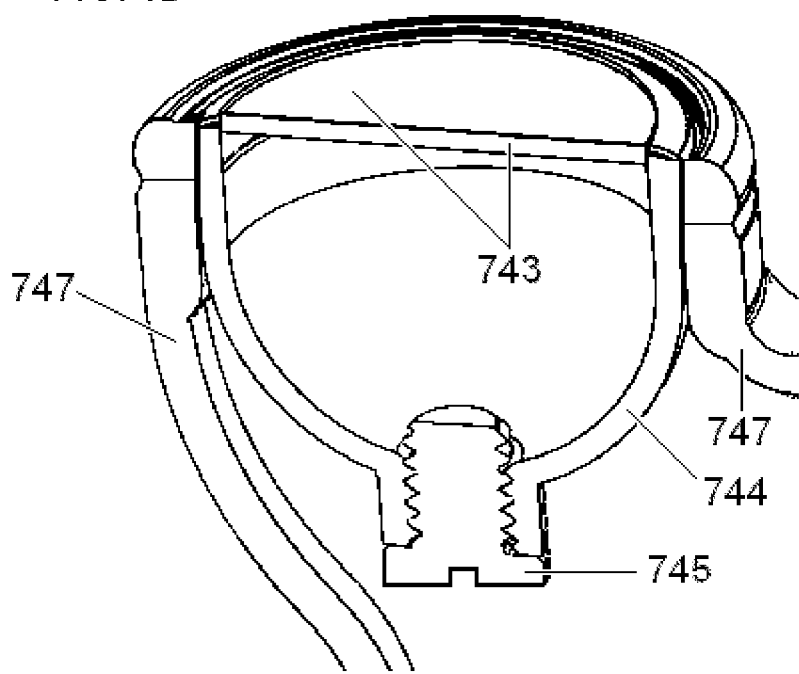
FIG. 4D is a cut-a-way view of the electrode assembly of FIG. 4C.

Details of one embodiment of the stimulator head are shown in FIGS. 4C and 4D. The electrode head may be assembled from a disc without fenestration (743), or alternatively from a snap-on cap that serves as a tambour for a dielectric or conducting membrane, or alternatively the head may have a solid fenestrated head-cup. The electrode may also be a screw (745). The preferred embodiment of the disc (743) is a solid, ordinarily uniformly conducting disc (e.g., metal such as stainless steel), which is possibly flexible in some embodiments. An alternate embodiment of the disc is a non-conducting (e.g., plastic) aperture screen that permits electrical current to pass through its apertures, e.g., through an array of apertures (fenestration). The electrode (745, also 340 in FIG. 2B) seen in each stimulator head may have the shape of a screw that is flattened on its tip. Pointing of the tip would make the electrode more of a point source, such that the equations for the electrical potential may have a solution corresponding more closely to a far-field approximation. Rounding of the electrode surface or making the surface with another shape will likewise affect the boundary conditions that determine the electric field. Completed assembly of the stimulator head is shown in FIG. 4D, which also shows how the head is attached to the body of the stimulator (747).

If a membrane is used, it ordinarily serves as the interface shown as 351 in FIG. 2B. For example, the membrane may be made of a dielectric (non-conducting) material, such as a thin sheet of Mylar (biaxially-oriented polyethylene terephthalate, also known as BoPET). In other embodiments, it may be made of conducting material, such as a sheet of Tecophlic material from Lubrizol Corporation, 29400 Lakeland Boulevard, Wickliffe, Ohio 44092. In one embodiment, apertures of the disc may be open, or they may be plugged with conducting material, for example, KM10T hydrogel from Katecho Inc., 4020 Gannett Ave., Des Moines IA 50321. If the apertures are so-plugged, and the membrane is made of conducting material, the membrane becomes optional, and the plug serves as the interface 351 shown in FIG. 2B.

The head-cup (744) is filled with conducting material (350 in FIG. 2B), for example, SIGNAGEL Electrode Gel from Parker Laboratories, Inc., 286 Eldridge Rd., Fairfield NJ 07004. The head-cup (744) and body of the stimulator are made of a non-conducting material, such as acrylonitrile butadiene styrene. The depth of the head-cup from its top surface to the electrode may be between one and six centimeters. The head-cup may have a different curvature than what is shown in FIG. 4, or it may be tubular or conical or have some other inner surface geometry that will affect the Neumann boundary conditions that determine the electric field strength.

If an outer membrane is used and is made of conducting materials, and the disc (743) in FIG. 4C is made of solid conducting materials such as stainless steel, then the membrane becomes optional, in which case the disc may serve as the interface 351 shown in FIG. 2B. Thus, an embodiment without the membrane is shown in FIGS. 4C and 4D. This version of the device comprises a solid (but possibly flexible in some embodiments) conducting disc that cannot absorb fluid, the non-conducting stimulator head (744) into or onto which the disc is placed, and the electrode (745), which is also a screw. It is understood that the disc (743) may have an anisotropic material or electrical structure, for example, wherein a disc of stainless steel has a grain, such that the grain of the disc should be rotated about its location on the stimulator head, in order to achieve optimal electrical stimulation of the patient. As seen in FIG. 4D, these items are assembled to become a sealed stimulator head that is attached to the body of the stimulator (747). The disc (743) may screw into the stimulator head (744), it may be attached to the head with adhesive, or it may be attached by other methods that are known in the art. The chamber of the stimulator head-cup is filled with a conducting gel, fluid, or paste, and because the disc (743) and electrode (745) are tightly sealed against the stimulator head-cup (744), the conducting material within the stimulator head cannot leak out. In addition, this feature allows the user to easily clean the outer surface of the device (e.g., with isopropyl alcohol or similar disinfectant), avoiding potential contamination during subsequent uses of the device.

In some embodiments, the interface comprises a fluid permeable material that allows for passage of current through the permeable portions of the material. In these embodiments, a conductive medium (such as a gel) is preferably situated between the electrode(s) and the permeable interface. The conductive medium provides a conductive pathway for electrons to pass through the permeable interface to the outer surface of the interface and to the patient's skin.

In other embodiments of the present description, the interface (351 in FIG. 2B) is made from a very thin material with a high dielectric constant, such as material used to make capacitors. For example, it may be Mylar having a submicron thickness (preferably in the range about 0.5 to about 1.5 microns) having a dielectric constant of about 3. Because one side of Mylar is slick, and the other side is microscopically rough, the present description contemplates two different configurations: one in which the slick side is oriented towards the patient's skin, and the other in which the rough side is so-oriented. Thus, at stimulation Fourier frequencies of several kilohertz or greater, the dielectric interface will capacitively couple the signal through itself, because it will have an impedance comparable to that of the skin. Thus, the dielectric interface will isolate the stimulator's electrode from the tissue, yet allow current to pass. In one embodiment of the present description, non-invasive electrical stimulation of a nerve is accomplished essentially substantially capacitively, which reduces the amount of ohmic stimulation, thereby reducing the sensation the patient feels on the tissue surface. This would correspond to a situation, for example, in which at least 30%, preferably at least 50%, of the energy stimulating the nerve comes from capacitive coupling through the stimulator interface, rather than from ohmic coupling. In other words, a substantial portion (e.g., 50%) of the voltage drop is across the dielectric interface, while the remaining portion is through the tissue.

In certain exemplary embodiments, the interface and/or its underlying mechanical support comprise materials that will also provide a substantial or complete seal of the interior of the device. This inhibits any leakage of conducting material, such as gel, from the interior of the device and also inhibits any fluids from entering the device. In addition, this feature allows the user to easily clean the surface of the dielectric material (e.g., with isopropyl alcohol or similar disinfectant), avoiding potential contamination during subsequent uses of the device. One such material is a thin sheet of Mylar, supported by a stainless steel disc, as described above.

The selection of the material for the dielectric constant involves at least two important variables: (1) the thickness of the interface; and (2) the dielectric constant of the material. The thinner the interface and/or the higher the dielectric constant of the material, the lower the voltage drop across the dielectric interface (and thus the lower the driving voltage required). For example, with Mylar, the thickness could be about 0.5 to about 5 microns (preferably about 1 micron) with a dielectric constant of about 3. For a piezoelectric material like barium titanate or PZT (lead zirconate titanate), the thickness could be about 100-400 microns (preferably about 200 microns or about 0.2 mm) because the dielectric constant is >1000.

One of the novelties of the embodiment that is a non-invasive capacitive stimulator (hereinafter referred to more generally as a capacitive electrode) arises in that it uses a low voltage (generally less than 100 volt) power source, which is made possible by the use of a suitable stimulation waveform, such as the waveform that is disclosed herein (FIG. 2). In addition, the capacitive electrode allows for the use of an interface that provides a more adequate seal of the interior of the device. The capacitive electrode may be used by applying a small amount of conductive material (e.g., conductive gel as described above) to its outer surface. In some embodiments, it may also be used by contacting dry skin, thereby avoiding the inconvenience of applying an electrode gel, paste, or other electrolytic material to the patient's skin and avoiding the problems associated with the drying of electrode pastes and gels. Such a dry electrode would be particularly suitable for use with a patient who exhibits dermatitis after the electrode gel is placed in contact with the skin [Ralph J. COSKEY. Contact dermatitis caused by ECG electrode jelly. Arch Dermatol 113(1977): 839-840]. The capacitive electrode may also be used to contact skin that has been wetted (e.g., with tap water or a more conventional electrolyte material) to make the electrode-skin contact (here the dielectric constant) more uniform [A L ALEXELONESCU, G Barbero, F C M Freire, and R Merletti. Effect of composition on the dielectric properties of hydrogels for biomedical applications. Physiol. Meas. 31 (2010) S169-S182].

As described below, capacitive biomedical electrodes are known in the art, but when used to stimulate a nerve noninvasively, a high voltage power supply is currently used to perform the stimulation. Otherwise, prior use of capacitive biomedical electrodes has been limited to invasive, implanted applications; to non-invasive applications that involve monitoring or recording of a signal, but not stimulation of tissue; to non-invasive applications that involve the stimulation of something other than a nerve (e.g., tumor); or as the dispersive electrode in electrosurgery.

Evidence of a long-felt but unsolved need, and evidence of failure of others to solve the problem that is solved by the this embodiment of the present description (low-voltage, non-invasive capacitive stimulation of a nerve), is provided by KELLER and Kuhn, who review the previous high-voltage capacitive stimulating electrode of GEDDES et al and write that "Capacitive stimulation would be a preferred way of activating muscle nerves and fibers, when the inherent danger of high voltage breakdowns of the dielectric material can be eliminated. Goal of future research could be the development of improved and ultra-thin dielectric foils, such that the high stimulation voltage can be lowered." [L. A. GEDDES, M. Hinds, and K. S. Foster. Stimulation with capacitor electrodes. Medical and Biological Engineering and Computing 25(1987): 359-360; Thierry KELLER and Andreas Kuhn. Electrodes for transcutaneous (surface) electrical stimulation. Journal of Automatic Control, University of Belgrade 18(2, 2008):35-45, on page 39]. It is understood that in the United States, according to the 2005 National Electrical Code, high voltage is any voltage over 600 volts. U.S. Pat. No. 3,077,884, entitled Electro-physiotherapy apparatus, to BARTROW et al, U.S. Pat. No. 4,144,893, entitled Neuromuscular therapy device, to HICKEY and U.S. Pat. No. 7,933,648, entitled High voltage transcutaneous electrical stimulation device and method, to TANRI-SEVER, also describe high voltage capacitive stimulation electrodes. U.S. Pat. No. 7,904,180, entitled Capacitive medical electrode, to JUOLA et al, describes a capacitive electrode that includes transcutaneous nerve stimulation as one intended application, but that patent does not describe stimulation voltages or stimulation waveforms and frequencies that are to be used for the transcutaneous stimulation. U.S. Pat. No. 7,715,921, entitled Electrodes for applying an electric field in-vivo over an extended period of time, to PALTI, and U.S. Pat. No. 7,805,201, entitled Treating a tumor or the like with an electric field, to PALTI, also describe capacitive stimulation electrodes, but they are intended for the treatment of tumors, do not disclose uses involving nerves, and teach stimulation frequencies in the range of 50 kHz to about 500 kHz.

This embodiment of the present description uses a different method to lower the high stimulation voltage than developing ultra-thin dielectric foils, namely, to use a suitable stimulation waveform, such as the waveform that is disclosed herein (FIG. 2). That waveform has significant Fourier components at higher frequencies than waveforms used for transcutaneous nerve stimulation as currently practiced. Thus, one of ordinary skill in the art would not have combined the claimed elements, because transcutaneous nerve stimulation is performed with waveforms having significant Fourier components only at lower frequencies, and noninvasive capacitive nerve stimulation is performed at higher voltages. In fact, the elements in combination do not merely perform the function that each element performs separately. The dielectric material alone may be placed in contact with the skin in order to perform pasteless or dry stimulation, with a more uniform current density than is associated with ohmic stimulation, albeit with high stimulation voltages [L. A. GEDDES, M. Hinds, and K. S. Foster. Stimulation with capacitor electrodes. Medical and Biological Engineering and Computing 25(1987): 359-360; Yong-min K I M, H. Gunter Zieber, and Frank A. Yang. Uniformity of current density under stimulating electrodes. Critical Reviews in Biomedical Engineering 17(1990, 6): 585-619]. With regard to the waveform element, a waveform that has significant Fourier components at higher frequencies than waveforms currently used for transcutaneous nerve stimulation may be used to selectively stimulate a deep nerve and avoid stimulating other nerves, as disclosed herein for both noncapacitive and capacitive electrodes. But it is the combination of the two elements (dielectric interface and waveform) that makes it possible to stimulate a nerve capacitively without using the high stimulation voltage as is currently practiced.

Another embodiment of the electrode-based stimulator is shown in FIG. 5, showing a device in which electrically conducting material is dispensed from the device to the patient's skin. In this embodiment, the interface (351 in FIG. 2B) is the conducting material itself. FIGS. 5A and 5B respectively provide top and bottom views of the outer surface of the electrical stimulator 50. FIG. 5C provides a bottom view of the stimulator 50, after sectioning along its long axis to reveal the inside of the stimulator.

Figure 5A:
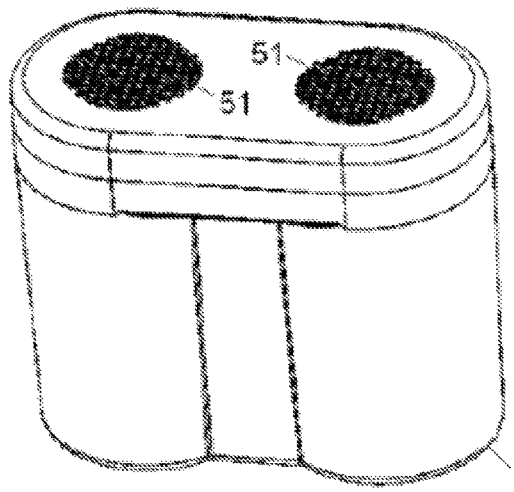
FIG. 5A is perspective view of the top of an alternative embodiment of the dual-electrode stimulator of FIG. 4A.
Figure 5B:
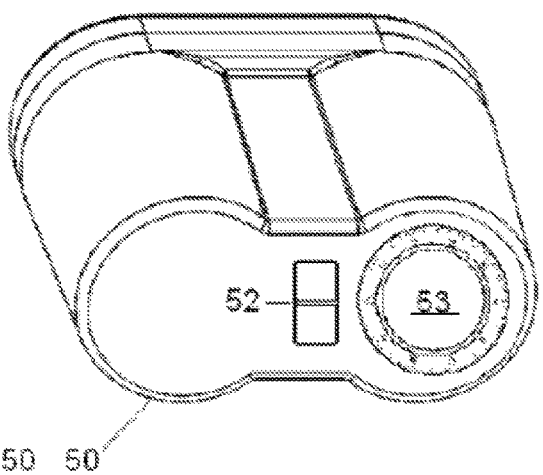
FIG. 5B is a perspective view of the bottom of the dual-electrode stimulator of FIG. 5A.
Figure 5C:
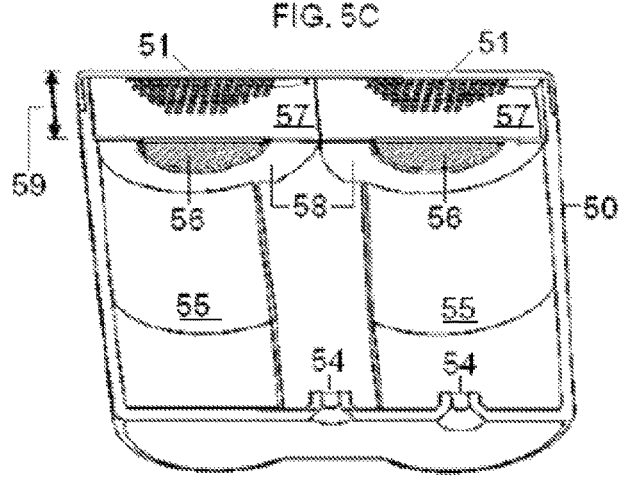
FIG. 5C is a cut-a-way view of the dual-electrode stimulator of FIG. 5A.

FIGS. 5A and 5C show a mesh 51 with openings that permit a conducting gel to pass from inside of the stimulator to the surface of the patient's skin at the position of nerve or tissue stimulation. Thus, the mesh with openings 51 is the part of the stimulator that is applied to the skin of the patient, through which conducting material may be dispensed. In any given stimulator, the distance between the two mesh openings 51 in FIG. 5A is constant, but it is understood that different stimulators may be built with different inter-mesh distances, in order to accommodate the anatomy and physiology of individual patients. Alternatively, the inter-mesh distance may be made variable as in the eyepieces of a pair of binoculars. A covering cap (not shown) is also provided to fit snugly over the top of the stimulator housing and the mesh openings 51, in order to keep the housing's conducting medium from leaking or drying when the device is not in use.

FIGS. 5B and 5C show the bottom of the self-contained stimulator 50. An on/off switch 52 is attached through a port 54, and a power-level controller 53 is attached through another port 54. The switch is connected to a battery power source (320 in FIG. 2B), and the power-level controller is attached to the control unit (330 in FIG. 2B) of the device. The power source battery and power-level controller, as well as the impulse generator (310 in FIG. 2B) are located (but not shown) in the rear compartment 55 of the housing of the stimulator 50.

Individual wires (not shown) connect the impulse generator (310 in FIG. 2B) to the stimulator's electrodes 56. The two electrodes 56 are shown here to be elliptical metal discs situated between the head compartment 57 and rear compartment 55 of the stimulator 50. A partition 58 separates each of the two head compartments 57 from one another and from the single rear compartment 55. Each partition 58 also holds its corresponding electrode in place. However, each electrode 56 may be removed to add electrically conducting gel (350 in FIG. 2B) to each head compartment 57. An optional non-conducting variable-aperture iris diaphragm may be placed in front of each of the electrodes within the head compartment 57, in order to vary the effective surface area of each of the electrodes. Each partition 58 may also slide towards the head of the device in order to dispense conducting gel through the mesh apertures 51. The position of each partition 58 therefore determines the distance 59 between its electrode 56 and mesh openings 51, which is variable in order to obtain the optimally uniform current density through the mesh openings 51. The outside housing of the stimulator 50, as well as each head compartment 57 housing and its partition 58, are made of electrically insulating material, such as acrylonitrile butadiene styrene, so that the two head compartments are electrically insulated from one another. Although the embodiment in FIG. 5 is shown to be a non-capacitive stimulator, it is understood that it may be converted into a capacitive stimulator by replacing the mesh openings 51 with a dielectric material, such as a sheet of Mylar, or by covering the mesh openings 51 with a sheet of such dielectric material.

In preferred embodiments of the electrode-based stimulator shown in FIG. 2B, electrodes are made of a metal, such as stainless steel, platinum, or a platinum-iridium alloy. However, in other embodiments, the electrodes may have many other sizes and shapes, and they may be made of other materials [Thierry KELLER and Andreas Kuhn. Electrodes for transcutaneous (surface) electrical stimulation. Journal of Automatic Control, University of Belgrade, 18(2, 2008): 35-45; G. M. LYONS, G. E. Leane, M. Clarke-Moloney, J. V. O'Brien, P. A. Grace. An investigation of the effect of electrode size and electrode location on comfort during stimulation of the gastrocnemius muscle. Medical Engineering & Physics 26 (2004) 873-878; Bonnie J. FORRESTER and Jerrold S. Petrofsky. Effect of Electrode Size, Shape, and Placement During Electrical Stimulation. The Journal of Applied Research 4, (2, 2004): 346-354; Gad ALON, Gideon Kantor and Henry S. Ho. Effects of Electrode Size on Basic Excitatory Responses and on Selected Stimulus Parameters. Journal of Orthopaedic and Sports Physical Therapy. 20(1, 1994):29-35].

For example, the stimulator's conducting materials may be nonmagnetic, and the stimulator may be connected to the impulse generator by long nonmagnetic wires (345 in FIG. 2B), so that the stimulator may be used in the vicinity of a strong magnetic field, possibly with added magnetic shielding. As another example, there may be more than two electrodes; the electrodes may comprise multiple concentric rings; and the electrodes may be disc-shaped or have a non-planar geometry. They may be made of other metals or resistive materials such as silicon-rubber impregnated with carbon that have different conductive properties [Stuart F. COGAN. Neural Stimulation and Recording Electrodes. Annu. Rev. Biomed. Eng. 2008. 10:275-309; Michael F. NOLAN. Conductive differences in electrodes used with transcutaneous electrical nerve stimulation devices. Physical Therapy 71(1991):746-751].

Although the electrode may consist of arrays of conducting material, the embodiments shown in FIGS. 4 and 5 avoid the complexity and expense of array or grid electrodes [Ana POPOVIC-BIJELIC, Goran Bijelic, Nikola Jorgovanovic, Dubravka Bojanic, Mirjana B. Popovic, and Dejan B. Popovic. Multi-Field Surface Electrode for Selective Electrical Stimulation. Artificial Organs 29 (6,2005):448-452; Dejan B. POPOVIC and Mirjana B. Popovic. Automatic determination of the optimal shape of a surface electrode: Selective stimulation. Journal of Neuroscience Methods 178 (2009) 174-181; Thierry KELLER, Marc Lawrence, Andreas Kuhn, and Manfred Morari. New Multi-Channel Transcutaneous Electrical Stimulation Technology for Rehabilitation. Proceedings of the 28th IEEE EMBS Annual International Conference New York City, USA, Aug. 30-Sep. 3, 2006 (WeC14.5): 194-197]. This is because the designs shown in FIGS. 4 and 5 provide a uniform surface current density, which would otherwise be a potential advantage of electrode arrays, and which is a trait that is not shared by most electrode designs [Kenneth R. BRENNEN. The Characterization of Transcutaneous Stimulating Electrodes. IEEE Transactions on Biomedical Engineering BME-23 (4, 1976): 337-340; Andrei PATRICIU, Ken Yoshida, Johannes J. Struijk, Tim P. DeMonte, Michael L. G. Joy, and Hans Stodkilde-Jorgensen. Current Density Imaging and Electrically Induced Skin Burns Under Surface Electrodes. IEEE Transactions on Biomedical Engineering 52 (12,2005): 2024-2031; R. H. GEUZE. Two methods for homogeneous field defibrillation and stimulation. Med. and Biol. Eng. and Comput. 21(1983), 518-520; J. PETROFSKY, E. Schwab, M. Cuneo, J. George, J. Kim, A. Almalty, D. Lawson, E. Johnson and W. Remigo. Current distribution under electrodes in relation to stimulation current and skin blood flow: are modern electrodes really providing the current distribution during stimulation we believe they are? Journal of Medical Engineering and Technology 30 (6,2006): 368-381; Russell G. MAUS, Erin M. McDonald, and R. Mark Wightman. Imaging of Nonuniform Current Density at Microelectrodes by Electrogenerated Chemiluminescence. Anal. Chem. 71(1999): 4944-4950]. In fact, patients found the design shown in FIGS. 4 and 5 to be less painful in a direct comparison with a commercially available grid-pattern electrode [UltraStim grid-pattern electrode, Axelggard Manufacturing Company, 520 Industrial Way, Fallbrook CA, 2011]. The embodiment of the electrode that uses capacitive coupling is particularly suited to the generation of uniform stimulation currents [Yongmin K I M, H. Gunter Zieber, and Frank A. Yang. Uniformity of current density under stimulating electrodes. Critical Reviews in Biomedical Engineering 17(1990, 6): 585-619].

The electrode-based stimulator designs shown in FIGS. 4 and 5 situate the electrode remotely from the surface of the skin within a chamber, with conducting material placed in the chamber between the skin and electrode. Such a chamber design had been used prior to the availability of flexible, flat, disposable electrodes [U.S. Pat. No. 3,659,614, entitled Adjustable headband carrying electrodes for electrically stimulating the facial and mandibular nerves, to Jankelson; U.S. Pat. No. 3,590,810, entitled Biomedical body electode, to Kopecky; U.S. Pat. No. 3,279,468, entitled Electrotherapeutic facial mask apparatus, to Le Vine; U.S. Pat. No. 6,757,556, entitled Electrode sensor, to Gopinathan et al; U.S. Pat. No. 4,383,529, entitled Iontophoretic electrode device, method and gel insert, to Webster; U.S. Pat. No. 4,220,159, entitled Electrode, to Francis et al. U.S. Pat. Nos. 3,862,633, 4,182,346, and 3,973,557, entitled Electrode, to Allison et al; U.S. Pat. No. 4,215,696, entitled Biomedical electrode with pressurized skin contact, to Bremer et al; and U.S. Pat. No. 4,166,457, entitled Fluid self-sealing bioelectrode, to Jacobsen et al.] The stimulator designs shown in FIGS. 4 and 5 are also self-contained units, housing the electrodes, signal electronics, and power supply. Portable stimulators are also known in the art, for example, U.S. Pat. No. 7,171,266, entitled Electro-acupuncture device with stimulation electrode assembly, to Gruzdowich. One of the novelties of the designs shown in FIGS. 4 and 5 is that the stimulator, along with a correspondingly suitable stimulation waveform, shapes the electric field, producing a selective physiological response by stimulating that nerve, but avoiding substantial stimulation of nerves and tissue other than the target nerve, particularly avoiding the stimulation of nerves that produce pain. The shaping of the electric field is described in terms of the corresponding field equations in commonly assigned application US20110230938 (application Ser. No. 13/075,746) entitled Devices and methods for non-invasive electrical stimulation and their use for vagal nerve stimulation on the neck of a patient, to SIMON et al., which is hereby incorporated by reference.

In one embodiment, the magnetic stimulator coil 341 in FIG. 2A has a body that is similar to the electrode-based stimulator shown in FIG. 5C. To compare the electrode-based stimulator with the magnetic stimulator, refer to FIG. 5D, which shows the magnetic stimulator 530 sectioned along its long axis to reveal its inner structure. As described below, it reduces the volume of conducting material that must surround a toroidal coil, by using two toroids, side-by-side, and passing electrical current through the two toroidal coils in opposite directions. In this configuration, the induced electrical current will flow from the lumen of one toroid, through the tissue and back through the lumen of the other, completing the circuit within the toroids' conducting medium. Thus, minimal space for the conducting medium is required around the outside of the toroids at positions near from the gap between the pair of coils. An additional advantage of using two toroids in this configuration is that this design will greatly increase the magnitude of the electric field gradient between them, which is crucial for exciting long, straight axons such as the vagus nerve and certain peripheral nerves.

Figure 5D:
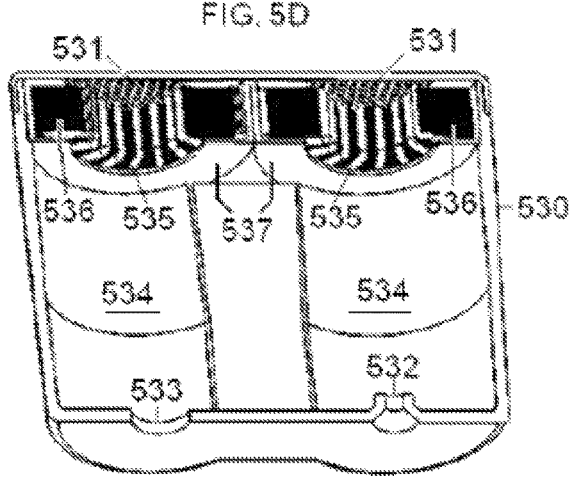
FIG. 5D is another cut-a-way view of the dual-electrode stimulator of FIG. 5.

As seen in FIG. 5D, a mesh 531 has openings that permit a conducting gel (within 351 in FIG. 2A) to pass from the inside of the stimulator to the surface of the patient's skin at the location of nerve or tissue stimulation. Thus, the mesh with openings 531 is the part of the magnetic stimulator that is applied to the skin of the patient.

FIG. 5D also shows openings at the opposite end of the magnetic stimulator 530. One of the openings is an electronics port 532 through which wires pass from the stimulator coil(s) to the impulse generator (310 in FIG. 2A). The second opening is a conducting gel port 533 through which conducting gel (351 in FIG. 2A) may be introduced into the magnetic stimulator 530 and through which a screw-driven piston arm may be introduced to dispense conducting gel through the mesh 531. The gel itself is contained within cylindrical-shaped but interconnected conducting medium chambers 534 that are shown in FIG. 5D. The depth of the conducting medium chambers 534, which is approximately the height of the long axis of the stimulator, affects the magnitude of the electric fields and currents that are induced by the magnetic stimulator device [Rafael CARBUNARU and Dominique M. Durand. Toroidal coil models for transcutaneous magnetic stimulation of nerves. IEEE Transactions on Biomedical Engineering. 48 (4,2001): 434-441].

FIG. 5D also show the coils of wire 535 that are wound around toroidal cores 536, consisting of high-permeability material (e.g., Supermendur). Lead wires (not shown) for the coils 535 pass from the stimulator coil(s) to the impulse generator (310 in FIG. 2A) via the electronics port 532. Different circuit configurations are contemplated. If separate lead wires for each of the coils 535 connect to the impulse generator (i.e., parallel connection), and if the pair of coils are wound with the same handedness around the cores, then the design is for current to pass in opposite directions through the two coils. On the other hand, if the coils are wound with opposite handedness around the cores, then the lead wires for the coils may be connected in series to the impulse generator, or if they are connected to the impulse generator in parallel, then the design is for current to pass in the same direction through both coils.

As also seen in FIG. 5D, the coils 535 and cores 536 around which they are wound are mounted as close as practical to the corresponding mesh 531 with openings through which conducting gel passes to the surface of the patient's skin. As shown, each coil and the core around which it is wound is mounted in its own housing 537, the function of which is to provide mechanical support to the coil and core, as well as to electrically insulate a coil from its neighboring coil. With this design, induced current will flow from the lumen of one toroid, through the tissue and back through the lumen of the other, completing the circuit within the toroids' conducting medium. A difference between the structure of the electrode-based stimulator shown in FIG. 5C and the magnetic stimulator shown in FIG. 5D is that the conducting gel is maintained within the chambers 57 of the electrode-based stimulator, which is generally closed on the back side of the chamber because of the presence of the electrode 56; but in the magnetic stimulator, the hole of each toroidal core and winding is open, permitting the conducting gel to enter the interconnected chambers 534.

Application of the Stimulators to the Neck of the Patient

Selected nerve fibers are stimulated in different embodiments of methods that make use of the disclosed electrical stimulation devices, including stimulation of the vagus nerve at a location in the patient's neck. At that location, the vagus nerve is situated within the carotid sheath, near the carotid artery and the interior jugular vein. The carotid sheath is located at the lateral boundary of the retopharyngeal space on each side of the neck and deep to the sternocleidomastoid muscle. The left vagus nerve is sometimes selected for stimulation because stimulation of the right vagus nerve may produce undesired effects on the heart, but depending on the application, the right vagus nerve or both right and left vagus nerves may be stimulated instead.

The three major structures within the carotid sheath are the common carotid artery, the internal jugular vein and the vagus nerve. The carotid artery lies medial to the internal jugular vein, and the vagus nerve is situated posteriorly between the two vessels. Typically, the location of the carotid sheath or interior jugular vein in a patient (and therefore the location of the vagus nerve) will be ascertained in any manner known in the art, e.g., by feel or ultrasound imaging. Proceeding from the skin of the neck above the sternocleidomastoid muscle to the vagus nerve, a line may pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein might be preferred for non-invasive stimulation of the vagus nerve. The magnetic stimulator coil may be centered on such a point, at the level of about the fifth to sixth cervical vertebra.

Figure 6B:
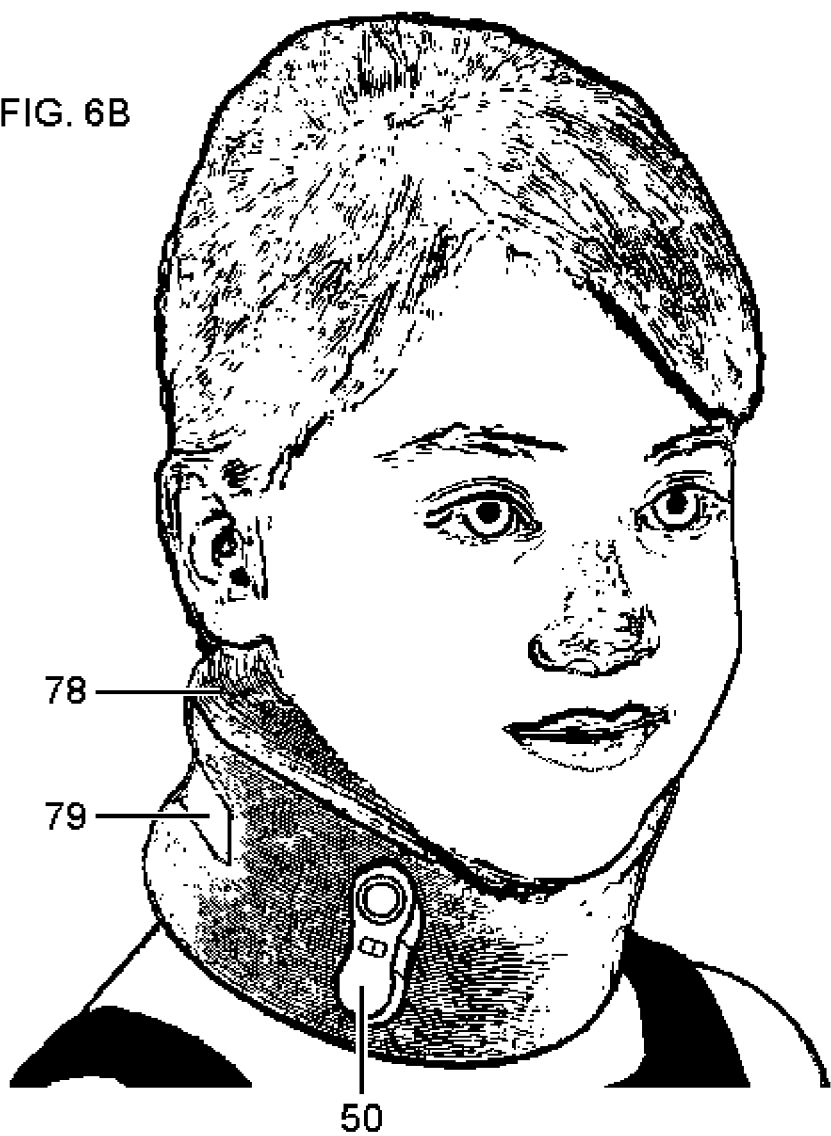
FIG. 6B illustrates the approximate position for stimulation of a child.

FIG. 6 illustrates use of the devices shown in FIGS. 3, 4 and 5 to stimulate the vagus nerve at that location in the neck, in which the stimulator device 50 or 530 in FIG. 5 is shown to be applied to the target location on the patient's neck as described above. For reference, FIG. 6A shows the locations of the following vertebrae: first cervical vertebra 71, the fifth cervical vertebra 75, the sixth cervical vertebra 76, and the seventh cervical vertebra 77. FIG. 6B shows the stimulator 50 applied to the neck of a child, which is partially immobilized with a foam cervical collar 78 that is similar to ones used for neck injuries and neck pain. The collar is tightened with a strap 79, and the stimulator is inserted through a hole in the collar to reach the child's neck surface. As shown, the stimulator is turned on and off with a switch that is located on the stimulator, and the amplitude of stimulation may be adjusted with a control knob that is also located on the stimulator. In other models, the stimulator may be turned on and off remotely, using a wireless controller that may be used to adjust all of the stimulation parameters of the controller (on/off, stimulation amplitude, frequency, etc.).

Figure 7:
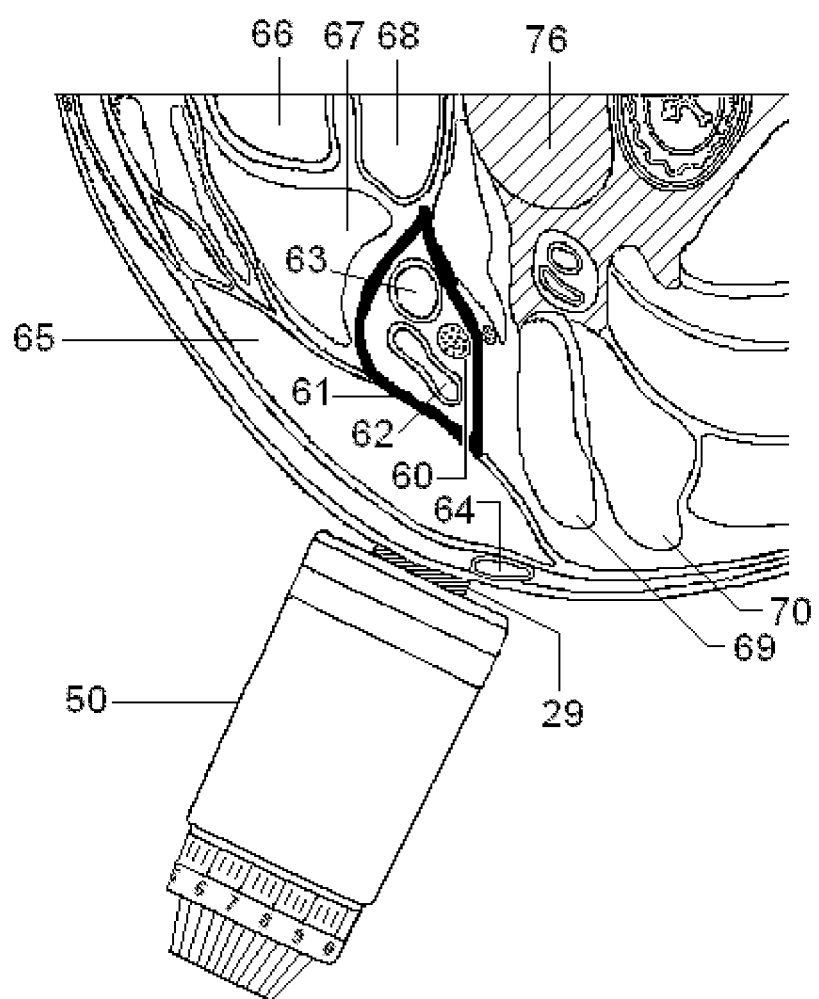
FIG. 7 illustrates the housing of the stimulator according one embodiment of the present description, when positioned to stimulate a vagus nerve in the patient's neck, wherein the stimulator is applied to the surface of the neck in the vicinity of the identified anatomical structures.

FIG. 7 provides a more detailed view of use of the electrical stimulator, when positioned to stimulate the vagus nerve at the neck location that is indicated in FIG. 6. As shown, the stimulator 50 in FIG. 5 touches the neck indirectly, by making electrical contact through conducting gel 29 (or other conducting material) which may be is dispensed through mesh openings (identified as 51 in FIG. 5) of the stimulator or applied as an electrode gel or paste. The layer of conducting gel 29 in FIG. 7 is shown to connect the device to the patient's skin, but it is understood that the actual location of the gel layer(s) may be generally determined by the location of mesh 51 shown in FIG. 5. Furthermore, it is understood that for other embodiments of the description, the conductive head of the device may not necessitate the use of additional conductive material being applied to the skin.

The vagus nerve 60 is identified in FIG. 7, along with the carotid sheath 61 that is identified there in bold peripheral outline. The carotid sheath encloses not only the vagus nerve, but also the internal jugular vein 62 and the common carotid artery 63. Features that may be identified near the surface of the neck include the external jugular vein 64 and the sternocleidomastoid muscle 65. Additional organs in the vicinity of the vagus nerve include the trachea 66, thyroid gland 67, esophagus 68, scalenus anterior muscle 69, and scalenus medius muscle 70. The sixth cervical vertebra 76 is also shown in FIG. 7, with bony structure indicated by hatching marks.

Methods of treating a patient comprise stimulating the vagus nerve as indicated in FIGS. 6 and 7, using the electrical stimulation devices that are disclosed herein. Stimulation may be performed on the left or right vagus nerve or on both of them simulataneously or alternately. The position and angular orientation of the device are adjusted about that location until the patient perceives stimulation when current is passed through the stimulator electrodes. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position. The stimulator signal may have a frequency and other parameters that are selected to produce a therapeutic result in the patient. Stimulation parameters for each patient are adjusted on an individualized basis. Ordinarily, the amplitude of the stimulation signal is set to the maximum that is comfortable for the patient, and then the other stimulation parameters are adjusted.

The stimulation is then performed with a sinusoidal burst waveform like that shown in FIG. 2. The pattern of a burst followed by silent inter-burst period repeats itself with a period of T. For example, the sinusoidal period tau may be 200 microseconds; the number of pulses per burst may be N=5; and the whole pattern of burst followed by silent inter-burst period may have a period of T=40000 microseconds, which is comparable to 25 Hz stimulation. More generally, there may be 1 to 20 pulses per burst, preferably five pulses. Each pulse within a burst has a duration of about 1 to about 1000 microseconds (i.e., about 1 to about 10 KHz), preferably about 200 microseconds (about 5 KHz). A burst followed by a silent inter-burst interval repeats at 1 to 5000 bursts per second (bps), preferably at 5-50 bps, and even more preferably 10-25 bps stimulation (10-25 Hz). The preferred shape of each pulse is a full sinusoidal wave, although triangular or other shapes may be used as well.

A vagus nerve stimulation treatment according to the present description is conducted for continuous period of thirty seconds to five minutes, preferably about 90 seconds to about three minutes and more preferably about two minutes (each defined as a single dose). After a dose has been completed, the therapy is stopped for a period of time (depending on the treatment as described below). For prophylactic treatments, such as a treatment to reduce or eliminate the severity, duration and/or number of migraines suffered by a patient, the therapy preferably comprises multiple doses/day over a period of time that may last from one week to a number of years. In certain embodiments, the treatment will comprise multiple doses at predetermined times during the day and/or at predetermined intervals throughout the day. In exemplary embodiments, the treatment comprises one of the following: (1) 3 doses/day at predetermined intervals or times; (2) two doses, either consecutively, or separated by 5 min at predetermined intervals or times, preferably two or three times/day; (3) 3 doses, either consecutively or separated by 5 min again at predetermined intervals or times, such as 2 or 3 times/day; or (4) 1-3 doses, either consecutively or separated by 5 min, 4-6 times per day. Initiation of a treatment may begin when an imminent attack (e.g., headache, seizure, etc) is forecasted, or in a risk-factor reduction program it may be performed throughout the day beginning after the patient arises in the morning.

For certain disorders, the time of day can be more important than the time interval between treatments. For example, the locus coreless has periods of time during a 24 hour day wherein it has inactive periods and active periods. Typically, the inactive periods can occur in the late afternoon or in the middle of the night when the patient is asleep. It is during the inactive periods that the levels of inhibitory neurotransmitters in the brain that are generated by the locus coreless are reduced. This may have an impact on certain disorders. For example, patients suffering from migraines or cluster headaches often receive these headaches after an inactive period of the locus coreless. For these types of disorders, the prophylactic treatment is optimal during the inactive periods such that the amounts of inhibitory neurotransmitters in the brain can remain at a higher enough level to mitigate or abort an acute attack of the disorder.

In these embodiments, the prophylatic treatment may comprise multiple doses/day timed for periods of inactivity of the locus coreless. In one embodiment, a treatment according to the present description comprises one or more doses administered 2-3 times per day or 2-3 "treatment sessions" per day. The treatment sessions preferably occur during the late afternoon or late evening, in the middle of the night and again in the morning when the patient wakes up. In an exemplary embodiment, each treatment session comprises 1-4 doses, preferably 2-3 doses, with each dose lasting for about 90 seconds to about three minutes.

For other disorders, the intervals between treatment sessions may be the most important as applicant has determined that stimulation of the vagus nerve can have a prolonged effect on the inhibitor neurotransmitters levels in the brain, e.g., at least one hour, up to 3 hours and sometimes up to 8 hours. In one embodiment, a treatment according to the present description comprises one or more doses (i.e., treatment sessions) administered at intervals during a 24 hour period. In a preferred embodiment, there are 1-5 such treatment sessions, preferably 2-4 treatment sessions. Each treatment session preferably comprises 1-3 doses, each lasting between about 60 seconds to about three minutes, preferably about 90 seconds to about 150 seconds, more preferably about 2 minutes.

For an acute treatment, such as treatment of acute stroke, the therapy according to the present description may comprise one or more embodiments: (1) 1 dose at the onset of symptoms; (2) 1 dose at the onset of symptoms, followed by another dose at 5-15 min; or (3) 1 dose every 15 minutes to 1 hour at the onset of symptoms until the acute attack has been mitigated or aborted. In these embodiments, each dose preferably last between about 60 seconds to about three minutes, preferably about 90 seconds to about 150 seconds, more preferably about 2 minutes.

For long term treatment of an acute insult such as one that occurs during the rehabilitation of a stroke patient, the therapy may consist of: (1) 3 treatments/day; (2) 2 treatments, either consecutively or separated by 5 min, 3×/day; (3) 3 treatments, either consecutively or separated by 5 min, 2×/day; (4) 2 or 3 treatments, either consecutively or separated by 5 min, up to 10×/day; or (5) 1, 2 or 3 treatments, either consecutively or separated by 5 min, every 15, 30, 60 or 120 min.

For all of the treatments listed above, one may alternate treatment between left and right sides, or in the case of stroke or migraine that occur in particular brain hemispheres, one may treat ipsilateral or contralateral to the stroke-hemisphere or headache side, respectively. Or for a single treatment, one may treat one minute on one side followed by one minute on the opposite side. Variations of these treatment paradigms may be chosen on a patient-by-patient basis. However, it is understood that parameters of the stimulation protocol may be varied in response to heterogeneity in the symptoms of patients. Different stimulation parameters may also be selected as the course of the patient's condition changes. In preferred embodiments, the disclosed methods and devices do not produce clinically significant side effects, such as agitation or anxiety, or changes in heart rate or blood pressure.

The prophylactic treatments may be most effective when the patient is in a prodromal, high-risk bistable state. In that state, the patient is simultaneously able to remain normal or exhibit symptoms, and the selection between normal and symptomatic states depends on the amplification of fluctuations by physiological feedback networks. For example, a thrombus may exist in either a gel or fluid phase, with the feedback amplification of fluctuations driving the change of phase and/or the volume of the gel phase. Thus, a thrombus may form or not, depending on the nonlinear dynamics exhibited by the network of enzymes involved in clot formation, as influenced by blood flow and inflammation that may be modulated by vagus nerve stimulation [PANTELEEV M A, Balandina A N, Lipets E N, Ovanesov M V, Ataullakhanov F I. Task-oriented modular decomposition of biological networks: trigger mechanism in blood coagulation. Biophys J 98(9, 2010):1751-1761; Alexey M SHIBEKO, Ekaterina S Lobanova, Mikhail A Panteleev and Fazoil I Ataullakhanov. Blood flow controls coagulation onset via the positive feedback of factor VII activation by factor Xa. BMC Syst Biol 2010; 4(2010):5, pp. 1-12]. Consequently, the mechanisms of vagus nerve stimulation treatment during prophylaxis for a stroke are generally different than what occurs during an acute treatment, when the stimulation inhibits excitatory neurotransmission that follows the onset of ischemia that is already caused by the thrombus. Nevertheless, the prophylactic treatment may also inhibit excitatory neurotransmission so as to limit the excitation that would eventually occur upon formation of a thrombus, and the acute treatment may prevent the formation of another thrombus.

The circuits involved in such inhibition are illustrated in FIG. 1A. Excitatory nerves within the dorsal vagal complex generally use glutamate as their neurotransmitter. To inhibit neurotransmission within the dorsal vagal complex, the present description makes use of the bidirectional connections that the nucleus of the solitary tract (NTS) has with structures that produce inhibitory neurotransmitters, or it makes use of connections that the NTS has with the hypothalamus, which in turn projects The general stimulation schedules described above, or an individualized protocol fashioned for each patient, are designed or justified using concepts that are analogous to the selection of drug treatment protocols. For drugs, pharmacological dose-response experiments measure the cumulative effect of a bolus of the drug on the physiological parameter that is to be controlled as a function of time (e.g., blood pressure). After administration of the drug, the effective concentration of the drug decreases, typically with an exponentially decaying half-life, but sometimes with a complex decay pattern, and the effect of the drug on the physiological parameter also eventually decreases. The situation is similar with vagus nerve stimulation. The effectiveness of vagus nerve stimulation on a physiological parameter may also be considered quantitatively (e.g., EEG-derived index of cerebral ischemia, see: FERREE TC, Hwa R C. Electrophysiological measures of acute cerebral ischaemia. Phys Med Biol 50(17, 2005):3927-3939). The effectiveness is a function of the stimulation voltage, the duration of the stimulation, and if stimulation has ceased, the time since cessation of the last stimulation. Accordingly, the numerical value of an "Accumulated Vagus Nerve Stimulation" with a particular waveform may be denoted as $S(t)$ and may for present purposes be represented as one that increases at a rate proportional to the stimulation voltage V and decays with a time constant $TAU_P$, such that after prolonged stimulation, the accumulated stimulation effectiveness will saturate at a value equal to the product of V and $TAU_P$. Thus, if $T_P$ is the duration of a stimulus pulse, then for time $t<T_P$, $S(t)=V_P[1-\exp(-t/TAU_P)]+S_0 \exp(-t/TAU_P)$. For $t>T_P$, $S(t)=S(T_P)\exp(-[t-T_P]/TAU_P)$, where the time t is measured from the start of a pulse, $S_0$ is the value of S when $t=0$, and the stimulation voltage V may be expressed in units of the volts needed to first elicit a response on the part of the patient. Because each patient may have a different value of $TAU_P$, the stimulus protocol needed to maintain the physiological value above or below a certain pre-determined value may likewise vary from patient to patient. If the decay of the nerve stimulation effect is complex, a model more complicated than simple exponential decay should be used, analogous to more complex models used in pharmacokinetics and pharmacodymanics.

In other embodiments of the description, pairing of vagus nerve stimulation may be with a additional sensory stimulation. The paired sensory stimulation may be bright light, sound, tactile stimulation, or electrical stimulation of the tongue to simulate odor/taste, e.g., pulsating with the same frequency as the vagus nerve electrical stimulation. The rationale for paired sensory stimulation is the same as simultaneous, paired stimulation of both left and right vagus nerves, namely, that the pair of signals interacting with one another in the brain may result in the formation of larger and more coherent neural ensembles than the neural ensembles associated with the individual signals, thereby enhancing the therapeutic effect.

For example, the hypothalamus is well known to be responsive to the presence of bright light, so exposing the patient to bright light that is fluctuating with the same stimulation frequency as the vagus nerve (or a multiple of that frequency) may be performed in an attempt to enhance the role of the hypothalamus in producing the desired therapeutic effect. Such paired stimulation does not necessarily rely upon neuronal plasticity and is in that sense different from other reports of paired stimulation [Navzer D. ENGINEER, Jonathan R. Riley, Jonathan D. Seale, Will A.

Vrana, Jai A. Shetake, Sindhu P. Sudanagunta, Michael S. Borland and Michael P. Kilgard. Reversing pathological neural activity using targeted plasticity. Nature 470(7332, 2011):101-104; PORTER B A, Khodaparast N, Fayyaz T, Cheung R J, Ahmed S S, Vrana W A, Rennaker R L 2nd, Kilgard M P. Repeatedly pairing vagus nerve stimulation with a movement reorganizes primary motor cortex. Cereb Cortex 22(10, 2012):2365-2374].

Selection of stimulation parameters to preferentially stimulate particular regions of the brain may be done empirically, wherein a set of stimulation parameters are chosen, and the responsive region of the brain is measured using fMRI or a related imaging method [CHAE JH, Nahas Z, Lomarev M, Denslow S, Lorberbaum J P, Bohning D E, George M S. A review of functional neuroimaging studies of vagus nerve stimulation (VNS). J Psychiatr Res. 37(6, 2003):443-455; CONWAY C R, Sheline Y I, Chibnall J T, George M S, Fletcher J W, Mintun M A. Cerebral blood flow changes during vagus nerve stimulation for depression. Psychiatry Res. 146(2, 2006):179-84]. Thus, by performing the imaging with different sets of stimulation parameters, a database may be constructed, such that the inverse problem of selecting parameters to match a particular brain region may be solved by consulting the database.

Stimulation waveforms may also be constructed by superimposing or mixing the burst waveform shown in FIG. 2, in which each component of the mixture may have a different period T, effectively mixing different burst-per-second waveforms. The relative amplitude of each component of the mixture may be chosen to have a weight according to correlations in different bands in an EEG for a particular resting state network. Thus, MANTINI et al performed simultaneous fMRI and EEG measurements and found that each resting state network has a particular EEG signature [see FIG. 3 in: MANTINI D, Perrucci M G, Del Gratta C, Romani G L, Corbetta M. Electrophysiological signatures of resting state networks in the human brain. Proc Natl Acad Sci USA 104(32,2007):13170-13175]. They reported relative correlations in each of the following bands, for each resting state network that was measured: delta (1-4 Hz), theta (4-8 Hz), alpha (8-13 Hz), beta (13-30 Hz), and gamma (30-50 Hz) rhythms. For recently-identified resting state networks, measurement of the corresponding signature EEG networks will have to be performed.

According to the present embodiment of the description, multiple signals shown in FIG. 2 are constructed, with periods T that correspond to a location near the midpoint of each of the EEG bands (e.g., using the MINATI data, T equals approximately 0.4 sec, 0.1667 sec, 0.095 sec, 0.0465 sec, and 0.025 sec, respectively). A more comprehensive mixture could also be made by mixing more than one signal for each band. These signals are then mixed, with relative amplitudes corresponding to the weights measured for any particular resting state network, and the mixture is used to stimulate the vagus nerve of the patient. Phases between the mixed signals are adjusted to optimize the fMRI signal for the resting state network that is being stimulated, thereby producing entrainment with the resting state network. Stimulation of a network may activate or deactivate a network, depending on the detailed configuration of adrenergic receptors within the network and their roles in enhancing or depressing neural activity within the network, as well as subsequent network-to-network interactions. It is understood that variations of this method may be used when different combined fMRI-EEG procedures are employed and where the same resting state may have different EEG signatures, depending on the circumstances [WU C W, Gu H, Lu H, Stein E A, Chen J H, Yang Y. Frequency specificity of functional connectivity in brain networks. Neuroimage 42(3, 2008):1047-1055; LAUFS H. Endogenous brain oscillations and related networks detected by surface EEG-combined fMRI. Hum Brain Mapp 29(7, 2008):762-769; MUSSO F, Brinkmeyer J, Mobascher A, Warbrick T, Winterer G. Spontaneous brain activity and EEG microstates. A novel EEG/fMRI analysis approach to explore resting-state networks. Neuroimage 52(4, 2010):1149-1161; ESPOSITO F, Aragri A, Piccoli T, Tedeschi G, Goebel R, Di Salle F. Distributed analysis of simultaneous EEG-fMRI time-series: modeling and interpretation issues. Magn Reson Imaging 27(8, 2009):1120-1130; FREYER F, Becker R, Anami K, Curio G, Villringer A, Ritter P. Ultrahigh-frequency EEG during fMRI: pushing the limits of imaging-artifact correction. Neuroimage 48(1, 2009):94-108]. Once the network is entrained, one may also attempt to change the signature EEG pattern of a network, by slowly changing the frequency content of the stimulation & EEG pattern of the network to which the stimulator is initially entrained. An objective in this case would be to modify the frequency content of the resting state signature EEG.

The individualized selection of parameters for the nerve stimulation protocol may based on trial and error in order to obtain a beneficial response without the sensation of skin pain or muscle twitches. Ordinarily, the amplitude of the stimulation signal is set to the maximum that is comfortable for the patient, and then the other stimulation parameters are adjusted. Alternatively, the selection of parameter values may involve tuning as understood in control theory, and as described below. It is understood that parameters may also be varied randomly in order to simulate normal physiological variability, thereby possibly inducing a beneficial response in the patient [Buchman T G. Nonlinear dynamics, complex systems, and the pathobiology of critical illness. Curr Opin Crit Care 10(5, 2004):378-82].

Use of Control Theory Methods to Improve Treatment of Individual Patients

The vagus nerve stimulation may employ methods of control theory (e.g., feedback) in an attempt to compensate for motion of the stimulator relative to the vagus nerve; to avoid potentially dangerous situations such as excessive heart rate; and to maintain measured EEG bands (e.g., delta, theta, alpha, beta) within predetermined ranges, in attempt to preferentially activate particular resting state networks. Thus, with these methods, the parameters of the vagus nerve stimulation may be changed automatically, depending on physiological measurements that are made, in attempt to maintain the values of the physiological signals within predetermined ranges.

Measurement of the patient's EEG is preferably performed as part of one disclosed method for selecting the parameters of vagus nerve stimulation, as described in the previous section. The EEG also provides dynamic physiological data concerning the onset and course of an acute stroke [JORDAN K G. Emergency EEG and continuous EEG monitoring in acute ischemic stroke. J Clin Neurophysiol 21(5, 2004):341-352; FERREE T C, Hwa R C. Electrophysiological measures of acute cerebral ischaemia. Phys Med Biol 50(17, 2005):3927-3939].

It is understood that the effects of vagus nerve stimulation on surface EEG waveforms may be difficult to detect [Michael BEWERNITZ, Georges Ghacibeh, Onur Seref, Panos M. Pardalos, Chang-Chia Liu, and Basim Uthman. Quantification of the impact of vagus nerve stimulation parameters on electroencephalographic measures. AIP Conf. Proc. DATA MINING, SYSTEMS ANALYSIS AND OPTIMI- ZATION IN BIOMEDICINE; Nov. 5, 2007, Volume 953, pp. 206-219], but they may exist nevertheless [KOO B. EEG changes with vagus nerve stimulation. J Clin Neurophysiol. 18(5, 2001):434-41; KUBA R, Guzaninová M, Brázdil M, Novák Z, Chrastina J, Rektor I. Effect of vagal nerve stimulation on interictal epileptiform discharges: a scalp EEG study. Epilepsia. 43(10, 2002):1181-8; RIZZO P, Beelke M, De Carli F, Canovaro P, Nobili L, Robert A, Fornaro P, Tanganelli P, Regesta G, Ferrillo F. Modifications of sleep EEG induced by chronic vagus nerve stimulation in patients affected by refractory epilepsy. Clin Neurophysiol. 115(3, 2004):658-64].

When stimulating the vagus nerve, motion variability may often be attributable to the patient's breathing, which involves contraction and associated change in geometry of the sternocleidomastoid muscle that is situated close to the vagus nerve (identified as 65 in FIG. 7). Modulation of the stimulator amplitude to compensate for this variability may be accomplished by measuring the patient's respiratory phase, or more directly by measuring movement of the stimulator, then using controllers (e.g., PID controllers) that are known in the art of control theory, as now described.

FIG. 8 is a control theory representation of the disclosed vagus nerve stimulation methods. As shown there, the patient, or the relevant physiological component of the patient, is considered to be the "System" that is to be controlled. The "System" (patient) receives input from the "Environment." For example, the environment would include ambient temperature, light, and sound. If the "System" is defined to be only a particular physiological component of the patient, the "Environment" may also be considered to include physiological systems of the patient that are not included in the "System". Thus, if some physiological component can influence the behavior of another physiological component of the patient, but not vice versa, the former component could be part of the environment and the latter could be part of the system. On the other hand, if it is intended to control the former component to influence the latter component, then both components should be considered part of the "System."

The System also receives input from the "Controller", which in this case may comprise the vagus nerve stimulation device, as well as electronic components that may be used to select or set parameters for the stimulation protocol (amplitude, frequency, pulse width, burst number, etc.) or alert the patient as to the need to use or adjust the stimulator (i.e., an alarm). For example, the controller may include the control unit 330 in FIG. 2. Feedback in the schema shown in FIG. 8 is possible because physiological measurements of the System are made using sensors. Thus, the values of variables of the system that could be measured define the system's state ("the System Output"). As a practical matter, only some of those measurements are actually made, and they represent the "Sensed Physiological Input" to the Controller.

The preferred sensors will include ones ordinarily used for ambulatory monitoring. For example, the sensors may comprise those used in conventional Holter and bedside monitoring applications, for monitoring heart rate and variability, ECG, respiration depth and rate, core temperature, hydration, blood pressure, brain function, oxygenation, skin impedance, and skin temperature. The sensors may be embedded in garments or placed in sports wristwatches, as currently used in programs that monitor the physiological status of soldiers [G. A. SHAW, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington MA. 1 Nov. 2004, pp. 1-141]. The ECG sensors should be adapted to the automatic extraction and analysis of particular features of the ECG, for example, indices of P-wave morphology, as well as heart rate variability indices of parasympathetic and sympathetic tone. Measurement of respiration using noninvasive inductive plethysmography, mercury in silastic strain gauges or impedance pneumography is particularly advised, in order to account for the effects of respiration on the heart. A noninvasive accelerometer may also be included among the ambulatory sensors, in order to identify motion artifacts. An event marker may also be included in order for the patient to mark relevant circumstances and sensations.

For brain monitoring, the sensors may comprise ambulatory EEG sensors [CASSON A, Yates D, Smith S, Duncan J, Rodriguez-Villegas E. Wearable electroencephalography. What is it, why is it needed, and what does it entail? IEEE Eng Med Biol Mag. 29(3, 2010):44-56] or optical topography systems for mapping prefrontal cortex activation [Atsumori H, Kiguchi M, Obata A, Sato H, Katura T, Funane T, Maki A. Development of wearable optical topography system for mapping the prefrontal cortex activation. Rev Sci Instrum. 2009 April; 80(4):043704]. Signal processing methods, comprising not only the application of conventional linear filters to the raw EEG data, but also the nearly real-time extraction of non-linear signal features from the data, may be considered to be a part of the EEG monitoring [D. Puthankattil SUBHA, Paul K. Joseph, Rajendra Acharya U, and Choo Min Lim. EEG signal analysis: A survey. J Med Syst 34(2010):195-212]. In the present application, the features would include EEG bands (e.g., delta, theta, alpha, beta).

Detection of the phase of respiration may be performed non-invasively by adhering a thermistor or thermocouple probe to the patient's cheek so as to position the probe at the nasal orifice. Strain gauge signals from belts strapped around the chest, as well as inductive plethysmography and impedance pneumography, are also used traditionally to non-invasively generate a signal that rises and falls as a function of the phase of respiration. Respiratory phase may also be inferred from movement of the sternocleidomastoid muscle that also causes movement of the vagus nerve stimulator during breathing, measured using accelerometers attached to the vagus nerve stimulator, as described below. After digitizing such signals, the phase of respiration may be determined using software such as "puka", which is part of PhysioToolkit, a large published library of open source software and user manuals that are used to process and display a wide range of physiological signals [GOLDBERGER A L, Amaral L A N, Glass L, Hausdorff J M, Ivanov P Ch, Mark R G, Mietus J E, Moody G B, Peng C K, Stanley H E. PhysioBank, PhysioToolkit, and PhysioNet: Components of a New Research Resource for Complex Physiologic Signals. Circulation 101(23, 2000):e215-e220] available from PhysioNet, M.I.T. Room E25-505A, 77 Massachusetts Avenue, Cambridge, MA 02139]. In one embodiment of the present description, the control unit 330 contains an analog-to-digital converter to receive such analog respiratory signals, and software for the analysis of the digitized respiratory waveform resides within the control unit 330. That software extracts turning points within the respiratory waveform, such as end-expiration and end-inspiration, and forecasts future turning-points, based upon the frequency with which waveforms from previous breaths match a partial waveform for the current breath. The control unit 330 then controls the impulse generator 310, for example, to stimulate the selected nerve only during a selected phase of respiration, such as all of inspiration or only the first second of inspiration, or only the expected middle half of inspiration.

It may be therapeutically advantageous to program the control unit 330 to control the impulse generator 310 in such a way as to temporally modulate stimulation by the magnetic stimulator coils or electrodes, depending on the phase of the patient's respiration. In patent application JP2008/081479A, entitled Vagus nerve stimulation system, to YOSHIHOTO, a system is also described for keeping the heart rate within safe limits. When the heart rate is too high, that system stimulates a patient's vagus nerve, and when the heart rate is too low, that system tries to achieve stabilization of the heart rate by stimulating the heart itself, rather than use different parameters to stimulate the vagus nerve. In that disclosure, vagal stimulation uses an electrode, which is described as either a surface electrode applied to the body surface or an electrode introduced to the vicinity of the vagus nerve via a hypodermic needle. That disclosure is unrelated to stroke or transient ischemic attack problems that are addressed here, but it does consider stimulation during particular phases of the respiratory cycle, for the following reason. Because the vagus nerve is near the phrenic nerve, Yoshihoto indicates that the phrenic nerve will sometimes be electrically stimulated along with the vagus nerve. The present applicants have not experienced this problem, so the problem may be one of a misplaced electrode. In any case, the phrenic nerve controls muscular movement of the diaphragm, so consequently, stimulation of the phrenic nerve causes the patient to hiccup or experience irregular movement of the diaphragm, or otherwise experience discomfort. To minimize the effects of irregular diaphragm movement, Yoshihoto's system is designed to stimulate the phrenic nerve (and possibly co-stimulate the vagus nerve) only during the inspiration phase of the respiratory cycle and not during expiration. Furthermore, the system is designed to gradually increase and then decrease the magnitude of the electrical stimulation during inspiration (notably amplitude and stimulus rate) so as to make stimulation of the phrenic nerve and diaphragm gradual.

The present description also discloses stimulation of the vagus nerve as a function of respiratory phase, but the rationale for such stimulation is different from Yoshihoto's method.

In some embodiments of the description, overheating of the magnetic stimulator coil may also be minimized by optionally restricting the magnetic stimulation to particular phases of the respiratory cycle, allowing the coil to cool during the other phases of the respiratory cycle. Alternatively, greater peak power may be achieved per respiratory cycle by concentrating all the energy of the magnetic pulses into selected phases of the respiratory cycle.

Furthermore, as an option in the present description, parameters of the stimulation may be modulated by the control unit 330 to control the impulse generator 310 in such a way as to temporally modulate stimulation by the magnetic stimulator coil or electrodes, so as to achieve and maintain the heart rate within safe or desired limits. In that case, the parameters of the stimulation are individually raised or lowered in increments (power, frequency, etc.), and the effect as an increased, unchanged, or decreased heart rate is stored in the memory of the control unit 330. When the heart rate changes to a value outside the specified range, the control unit 330 automatically resets the parameters to values that had been recorded to produce a heart rate within that range, or if no heart rate within that range has yet been achieved, it increases or decreases parameter values in the direction that previously acquired data indicate would change the heart rate in the direction towards a heart rate in the desired range. Similarly, the arterial blood pressure is also recorded non-invasively in an embodiment of the description, and as described above, the control unit 330 extracts the systolic, diastolic, and mean arterial blood pressure from the blood pressure waveform. The control unit 330 will then control the impulse generator 310 in such a way as to temporally modulate nerve stimulation by the magnetic stimulator coil or electrodes, in such a way as to achieve and maintain the blood pressure within predetermined safe or desired limits, by the same method that was indicated above for the heart rate. Thus, even if one does not intend to treat problems associated with stroke, embodiments of the description described above may be used to achieve and maintain the heart rate and blood pressure within desired ranges.

Let the measured output variables of the system in FIG. 8 be denoted by $y_i$ (i=1 to Q); let the desired (reference or setpoint) values of $y_i$ be denoted by $r_i$ and let the controller's input to the system consist of variables $u_j$ (j=1 to P). The objective is for a controller to select the input $u_j$ in such a way that the output variables (or a subset of them) closely follows the reference signals $r_i$, i.e., the control error $e_i=r_i-y_i$ is small, even if there is environmental input or noise to the system. Consider the error function $e_i=r_i-y_i$ to be the sensed physiological input to the controller in FIG. 8 (i.e., the reference signals are integral to the controller, which subtracts the measured system values from them to construct the control error signal). The controller will also receive a set of measured environmental signals $v_k$ (k=1 to R), which also act upon the system as shown in FIG. 8.

The functional form of the system's input u(t) is constrained to be as shown in FIGS. 2D and 2E. Ordinarily, a parameter that needs adjusting is the one associated with the amplitude of the signal shown in FIG. 2. As a first example of the use of feedback to control the system, consider the problem of adjusting the input u(t) from the vagus nerve stimulator (i.e., output from the controller) in order to compensate for motion artifacts.

Nerve activation is generally a function of the second spatial derivative of the extracellular potential along the nerve's axon, which would be changing as the position of the stimulator varies relative to the axon [F. RATTAY. The basic mechanism for the electrical stimulation of the nervous system. Neuroscience 89 (2, 1999):335-346]. Such motion artifact can be due to movement by the patient (e.g., neck movement) or movement within the patient (e.g. sternocleidomastoid muscle contraction associated with respiration), or it can be due to movement of the stimulator relative to the body (slippage or drift). Thus, one expects that because of such undesired or unavoidable motion, there will usually be some error (e=r−y) in the intended (r) versus actual (y) nerve stimulation amplitude that needs continuous adjustment.

Accelerometers can be used to detect all these types of movement, using for example, Model LSM330DL from STMicroelectronics, 750 Canyon Dr #300 Coppell, TX 75019. One or more accelerometer is attached to the patient's neck, and one or more accelerometer is attached to the head of the stimulator in the vicinity of where the stimulator contacts the patient. Because the temporally integrated outputs of the accelerometers provide a measurement of the current position of each accelerometer, the combined accelerometer outputs make it possible to measure any movement of the stimulator relative to the underlying tissue.

The location of the vagus nerve underlying the stimulator may be determined preliminarily by placing an ultrasound probe at the location where the center of the stimulator will be placed [KNAPPERTZ V A, Tegeler C H, Hardin S J, McKinney W M. Vagus nerve imaging with ultrasound: anatomic and in vivo validation. Otolaryngol Head Neck Surg 118(1, 1998):82-5]. The ultrasound probe is configured to have the same shape as the stimulator, including the attachment of one or more accelerometer. As part of the preliminary protocol, the patient with accelerometers attached is then instructed or helped to perform neck movements, breathe deeply so as to contract the sternocleidomastoid muscle, and generally simulate possible motion that may accompany prolonged stimulation with the stimulator. This would include possible slippage or movement of the stimulator relative to an initial position on the patient's neck. While these movements are being performed, the accelerometers are acquiring position information, and the corresponding location of the vagus nerve is determined from the ultrasound image. With these preliminary data, it is then possible to infer the location of the vagus nerve relative to the stimulator, given only the accelerometer data during a stimulation session, by interpolating between the previously acquired vagus nerve position data as a function of accelerometer position data.

For any given position of the stimulator relative to the vagus nerve, it is also possible to infer the amplitude of the electric field that it produces in the vicinity of the vagus nerve. This is done by calculation or by measuring the electric field that is produced by the stimulator as a function of depth and position within a phantom that simulates the relevant bodily tissue [Francis Marion MOORE. Electrical Stimulation for pain suppression: mathematical and physical models. Thesis, School of Engineering, Cornell University, 2007; Bartosz SAWICKI, Robert Szmurło, Przemysław Płonecki, Jacek Starzyiski, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. Thus, in order to compensate for movement, the controller may increase or decrease the amplitude of the output from the stimulator (u) in proportion to the inferred deviation of the amplitude of the electric field in the vicinity of the vagus nerve, relative to its desired value.

For present purposes, no distinction is made between a system output variable and a variable representing the state of the system. Then, a state-space representation, or model, of the system consists of a set of first order differential equations of the form d $y_i/dt = F_i(t, \{y_i\}, \{u_i\}, \{v_k\})$; $\{r_i\}$), where t is time and where in general, the rate of change of each variable $y_i$ is a function ($F_i$) of many other output variables as well as the input and environmental signals.

Classical control theory is concerned with situations in which the functional form of $F_i$ is as a linear combination of the state and input variables, but in which coefficients of the linear terms are not necessarily known in advance. In this linear case, the differential equations may be solved with linear transform (e.g., Laplace transform) methods, which convert the differential equations into algebraic equations for straightforward solution. Thus, for example, a single-input single-output system (dropping the subscripts on variables) may have input from a controller of the form:

$$u(t) = K_p e(t) + K_i \int_0^t e(\tau)d\tau + K_d \frac{de}{dt}$$

where the parameters for the controller are the proportional gain ($K_p$), the integral gain ($K_i$) and the derivative gain ($K_d$). This type of controller, which forms a controlling input signal with feedback using the error e=r−y, is known as a PID controller (proportional-integral-derivative).

Optimal selection of the parameters of the controller could be through calculation, if the coefficients of the corresponding state differential equation were known in advance. However, they are ordinarily not known, so selection of the controller parameters (tuning) is accomplished by experiments in which the error e either is or is not used to form the system input (respectively, closed loop or open loop experiments). In an open loop experiment, the input is increased in a step (or random binary sequence of steps), and the system response is measured. In a closed loop experiment, the integral and derivative gains are set to zero, the proportional gain is increased until the system starts to oscillate, and the period of oscillation is measured. Depending on whether the experiment is open or closed loop, the selection of PID parameter values may then be selected according to rules that were described initially by Ziegler and Nichols. There are also many improved versions of tuning rules, including some that can be implemented automatically by the controller [LI, Y., Ang, K. H. and Chong, G. C. Y. Patents, software and hardware for PID control: an overview and analysis of the current art. IEEE Control Systems Magazine, 26 (1,2006): 42-54; Karl Johan Åström & Richard M. Murray. Feedback Systems: An Introduction for Scientists and Engineers. Princeton NJ: Princeton University Press, 2008; Finn HAUGEN. Tuning of PID controllers (Chapter 10) In: Basic Dynamics and Control. 2009. ISBN 978-82-91748-13-9. TechTeach, Enggravhøgda 45, N-3711 Skien, Norway. http://techteach.no., pp. 129-155; Dingyu X U E, YangQuan Chen, Derek P. Atherton. PID controller design (Chapter 6), In: Linear Feedback Control: Analysis and Design with MATLAB. Society for Industrial and Applied Mathematics (SIAM). 3600 Market Street, 6th Floor, Philadelphia, PA (2007), pp. 183-235; Jan JANTZEN, Tuning Of Fuzzy PID Controllers, Technical University of Denmark, report 98-H 871, Sep. 30, 1998].

Commercial versions of PID controllers are available, and they are used in 90% of all control applications. To use such a controller, for example, in an attempt to maintain the EEG gamma band at a particular level relative to the alpha band, one could set the integral and derivative gains to zero, increase the proportional gain (amplitude of the stimulation) until the relative gamma band level starts to oscillate, and then measure the period of oscillation. The PID would then be set to its tuned parameter values.

Although classical control theory works well for linear systems having one or only a few system variables, special methods have been developed for systems in which the system is nonlinear (i.e., the state-space representation contains nonlinear differential equations), or multiple input/output variables. Such methods are important for the present description because the physiological system to be controlled will be generally nonlinear, and there will generally be multiple output physiological signals. It is understood that those methods may also be implemented in the controller shown in FIG. 8 [Torkel GLAD and Lennart Ljung. Control Theory. Multivariable and Nonlinear Methods. New York: Taylor and Francis, 2000; Zdzislaw BUBNICKI. Modern Control Theory. Berlin: Springer, 2005].

The controller shown in FIG. 8 may also make use of feed-forward methods [Coleman BROSILOW, Babu Joseph. Feedforward Control (Chapter 9) In: Techniques of Model-Based Control. Upper Saddle River, N.J.: Prentice Hall PTR, 2002. pp, 221-240]. Thus, the controller in FIG. 8 may be a type of predictive controller, methods for which have been developed in other contexts as well, such as when a model of the system is used to calculate future outputs of the system, with the objective of choosing among possible inputs so as to optimize a criterion that is based on future values of the system's output variables.

Performance of system control can be improved by combining the feedback closed-loop control of a PID controller with feed-forward control, wherein knowledge about the system's future behavior can be fed forward and combined with the PID output to improve the overall system performance. For example, if the sensed environmental input in FIG. 8 is such the environmental input to the system will have a deleterious effect on the system after a delay, the controller may use this information to provide anticipatory control input to the system, so as to avert or mitigate the deleterious effects that would have been sensed only after-the-fact with a feedback-only controller.

A mathematical model of the system is needed in order to perform the predictions of system behavior, e.g., make predictions concerning the patient's future status regarding a stroke or transient ischemic attack. Models that are completely based upon physical first principles (white-box) are rare, especially in the case of physiological systems. Instead, most models that make use of prior structural and mechanistic understanding of the system are so-called grey-box models. If the mechanisms of the systems are not sufficiently understood in order to construct a white or grey box model, a black-box model may be used instead. Such black box models comprise autoregressive models [Tim BOLLERSLEV. Generalized autoregressive conditional heteroscedasticity. Journal of Econometrics 31(1986):307-327], or those that make use of principal components [James H. STOCK, Mark W. Watson. Forecasting with Many Predictors, In: Handbook of Economic Forecasting. Volume 1, G. Elliott, C. W. J. Granger and A. Timmermann, eds (2006) Amsterdam: Elsevier B. V, pp 515-554], Kalman filters [Eric A. WAN and Rudolph van der Merwe. The unscented Kalman filter for nonlinear estimation, In: Proceedings of Symposium 2000 on Adaptive Systems for Signal Processing, Communication and Control (AS-SPCC), IEEE, Lake Louise, Alberta, Canada, October, 2000, pp 153-158], wavelet transforms [O. RENAUD, J.-L. Stark, F. Murtagh. Wavelet-based forecasting of short and long memory time series. Signal Processing 48(1996):51-65], hidden Markov models [Sam ROWEIS and Zoubin Ghahramani. A Unifying Review of Linear Gaussian Models. Neural Computation 11(2, 1999): 305-345], or artificial neural networks [Guoquiang ZHANG, B. Eddy Patuwo, Michael Y. Hu. Forecasting with artificial neural networks: the state of the art. International Journal of Forecasting 14(1998): 35-62].

For the present description, if a black-box model must be used, the preferred model will be one that makes use of support vector machines. A support vector machine (SVM) is an algorithmic approach to the problem of classification within the larger context of supervised learning. A number of classification problems whose solutions in the past have been solved by multi-layer back-propagation neural networks, or more complicated methods, have been found to be more easily solvable by SVMs [Christopher J. C. BURGES. A tutorial on support vector machines for pattern recognition. Data Mining and Knowledge Discovery 2(1998), 121-167; J. A. K. SUYKENS, J. Vandewalle, B. De Moor. Optimal Control by Least Squares Support Vector Machines. Neural Networks 14 (2001):23-35; SAPANKEVYCH, N. and Sankar, R. Time Series Prediction Using Support Vector Machines: A Survey. IEEE Computational Intelligence Magazine 4(2, 2009): 24-38; PRESS, W H; Teukolsky, S A; Vetterling, W T; Flannery, B P (2007). Section 16.5. Support Vector Machines. In: Numerical Recipes: The Art of Scientific Computing (3rd ed.). New York: Cambridge University Press].

Consider now the problem of predicting and possibly averting a stroke or transient ischemic attack. The example assumes that vagus nerve stimulation can be applied as described above, but the stimulation is applied only when the description's feedforward system predicts that a stroke or transient ischemic attack is imminent. Candidates for the disclosed forecasting methods include individuals who have had a recent transient ischemic attack and are likely to suffer a stroke in the next few days [JOHNSTON S C, Rothwell P M, Nguyen-Huynh M N, Giles M F, Elkins J S, Bernstein A L, Sidney S. Validation and refinement of scores to predict very early stroke risk after transient ischaemic attack. Lancet 369(9558, 2007):283-292].

A training set of physiological data will have been acquired that includes whether or not a stroke or transient ischemic attack is in progress. Thus, the binary classification of the patient's state is whether or not a stroke or transient ischemic attack is in progress, and the data used to make the classification consist of acquired physiological data. The training data would preferably be acquired from a single individual, but as a practical matter the training set of data will ordinarily be obtained from a group of individuals who volunteer for ambulatory or hospital physiological monitoring. In general, the more physiological data that are acquired, the better the forecast will be.

Prediction that a stroke or TIA is imminent may be based upon the likely formation of a thrombosis or arterial embolism. In that regard, there exists an ambulatory monitoring device that will monitor for cerebral emboli [MacKINNON A D, Aaslid R, Markus H S. Long-term ambulatory monitoring for cerebral emboli using transcranial Doppler ultrasound. Stroke 35(1, 2004):73-8]. It measures the passage of emboli, typically at the middle cerebral artery, using a transcranial Doppler signal. Whereas some cerebral emboli produce symptoms of a stroke, other emboli do not produce symptoms and may not be recognized by the patient. Therefore, in one embodiment of the description, the detection of an embolus with the device mentioned above is used as input for the forecasting of a TIA or stroke, but the appearance of the embolus in and of itself does not necessarily trigger the forecast of an imminent TIA or stroke. Additional physiological variables are used to make the forecast.

Preferably, the additional physiological variables should include EEG and its derived features, heart rate (electrocardiogram leads), blood pressure (noninvasive tonometer), respiration (e.g., abdominal and thoracic plethysmography), and motion (accelerometer). For the monitoring of drug and medications, systemic metabolism, and changes in coagulation, body chemistry may also be measure noninvasively using transdermal reverse iontophoresis [Leboulanger B, Guy R H, Delgado-Charro M B. Reverse iontophoresis for non-invasive transdermal monitoring. Physiol Meas 25(3, 2004):R35-50]. Preferably, the ambulatory noninvasive measurements would also include skin impedance (electrodermal leads), carbon dioxide (capnometry with nasual cannula), vocalization (microphones), light (light sensor), external and finger temperature (thermometers), etc., as well as parameters of the stimulator device, all evaluated at $\Delta$ time units prior to the time at which binary "stroke or transient ischemic attack in progress" (yes/no) data are acquired. Many values of delta may be considered, from seconds to minutes to hours. In general, as the value of delta increases, the calculated uncertainty of the forecast will also increase. The onset of the stroke or transient ischemic attack may be inferred from the data (e.g., EEG data) and/or from a patient activated event marker upon the appearance of symptoms such as sudden weakness or numbness, and dimming or loss of vision.

The selection of ambulatory noninvasive measurements may be motivated by physiological considerations. For example, the ECG may automatically monitor the presence (or forecast) of atrial fibrillation, ambulatory blood pressure monitors for the presence of acute increases in blood pressure, and body temperature thermometers monitors the presence of infection and inflammation. The status of the autonomic nervous system is likewise monitored through heart rate variability (via the ECG) and skin impedance. The EEG may also provide evidence of the onset and progression of ischemia [FERREE T C, Hwa R C. Electrophysiological measures of acute cerebral ischaemia. Phys Med Biol 50(17, 2005):3927-3939]. However, because the detailed physiological mechanisms of ischemic events are not fully understood, and a black box model is being used to make the forecast, physiological variables with an uncertain relevance to ischemia may also be monitored.

For a patient who is not experiencing a stroke or transient ischemic attack, the SVM is trained to forecast the imminence of a stroke or transient ischemic attack, A time units into the future, and the training set includes the above-mentioned physiological signals. The SVM is also trained to forecast the termination of a transient ischemic attack, A time units into the future, and the training set includes the time-course of features extracted from the above-mentioned physiological signals. After training the SVM, it is implemented as part of the controller. The controller may apply the vagus nerve stimulation as a prophylactic whenever there is a forecast of imminent stroke or transient ischemic attack. The controller may also be programmed to turn off the vagaus nerve stimulation when it forecasts or detects the termination of a transient ischemic attack. It is understood that in any event, the patient should treat any in-progress stroke or transient ischemic attack as a medical emergency and seek immediate emergency medical attention, notwithstanding the use of vagus nerve stimulation as a prophylactic. If the stroke or transient ischemic attack is only forecasted, the patient should immediately seek transportation to the waiting room of the nearest acute stroke treatment center or emergency room and wait at that location to see whether the predicted stroke or transient ischemic attack happens, notwithstanding the use of vagus nerve stimulation as a prophylactic that may have prevented the event.

Although the description herein has been described with reference to particular embodiments, it is to be understood that these embodiments are merely illustrative of the principles and applications of the present description. It is therefore to be understood that numerous modifications may be made to the illustrative embodiments and that other arrangements may be devised without departing from the spirit and scope of the present description as defined by the appended claims.

The invention claimed is:

1. A method of treating a symptom in a user, the method comprising:
   positioning a contact surface of a device in contact with an outer skin surface of a neck of the user;
   applying, via the device, an electrical impulse transcutaneously, via the contact surface, through the outer skin surface of the neck of the user to a nerve within the user according to a treatment paradigm; and
   wherein the treatment paradigm is based at least in part on an application of the electrical impulse as a single dose from about 30 seconds to about 5 minutes and wherein the treatment paradigm comprises a treatment session during a day, wherein the treatment session comprises applying the single dose from 2 to 5 times during the day.

2. The method of claim 1, wherein the single dose is from about 90 seconds to about 150 seconds.

3. The method of claim 1 wherein the device comprises a housing and an energy source, wherein the energy source is located within the housing, wherein the contact surface is coupled to the energy source, and wherein the housing comprises an outer surface that includes the contact surface, wherein the energy source generates the electrical impulse.

4. The method of claim 1, wherein the treatment session comprises applying the single dose 2 to 4 times in one hour.

5. The method of claim 1, wherein the treatment session comprises applying the single dose twice within a 15 minute time period.

6. The method of claim 1, wherein each single dose is applied within 5 minutes of each other.

7. The method of claim 1, wherein the device comprises one or more electrodes.

8. The method of claim 1, wherein the electrical impulse has a frequency from about 1 kHz to about 20 kHz.

9. The method of claim 1, wherein the electrical impulse comprises bursts of pulses, wherein the bursts each have a frequency from about 1 burst per second to about 100 bursts per second.

10. The method of claim 9, wherein each of the bursts contains from 2 to 20 pulses and each of the pulses is from about 100 microseconds to about 1000 microseconds in duration.

11. The method of claim 1, wherein the symptom is one of stress, withdrawal from substances, addiction, depression or lack of sleep.

* * * * *